(12) United States Patent
Mitra et al.

(10) Patent No.: US 12,090,482 B2
(45) Date of Patent: Sep. 17, 2024

(54) SYSTEMS AND METHODS FOR PERFORMING BIOLOGICAL ASSAYS

(71) Applicant: Pfizer Inc., New York, NY (US)

(72) Inventors: Debkishore Mitra, Fremont, CA (US); Frank B. Myers, III, Richmond, CA (US); John Robert Waldeisen, Berkeley, CA (US); Ivan Krastev Dimov, Union City, CA (US)

(73) Assignee: Pfizer Inc., New York, NY (US)

( * ) Notice: Subject to any disclaimer, the term of this patent is extended or adjusted under 35 U.S.C. 154(b) by 335 days.

(21) Appl. No.: 17/342,533

(22) Filed: Jun. 8, 2021

(65) Prior Publication Data

US 2022/0055030 A1    Feb. 24, 2022

Related U.S. Application Data

(63) Continuation of application No. 16/081,793, filed as application No. PCT/US2017/022300 on Mar. 14, 2017, now Pat. No. 11,123,736.

(Continued)

(51) Int. Cl.
| | |
|---|---|
| *B01L 3/00* | (2006.01) |
| *C12Q 1/6844* | (2018.01) |
| *G01N 27/447* | (2006.01) |

(52) U.S. Cl.
CPC .......... *B01L 3/5029* (2013.01); *C12Q 1/6844* (2013.01); *G01N 27/447* (2013.01);
(Continued)

(58) Field of Classification Search
CPC ........... B01L 3/5029; B01L 2300/0627; B01L 2300/0672; B01L 2300/0681; B01L 2300/0832; B01L 2300/0867; B01L 2300/087; B01L 2300/14; B01L 2300/1822; B01L 2300/1827; B01L 2300/1877; B01L 2400/0478; B01L 2400/0487; B01L 2400/0683; B01L 2400/0694; C12Q 1/6844; G01N 27/447
(Continued)

(56) References Cited

U.S. PATENT DOCUMENTS

| | | |
|---|---|---|
| D244,555 S | 5/1977 | Wiedmann |
| 4,310,488 A | 1/1982 | Rahm et al. |

(Continued)

FOREIGN PATENT DOCUMENTS

| | | | |
|---|---|---|---|
| AU | 2003272465 A1 | 4/2004 | |
| CA | 2495252 A1 | 3/2004 | |

(Continued)

OTHER PUBLICATIONS

U.S. Appl. No. 16/359,913, filed Mar. 20, 2019.
(Continued)

*Primary Examiner* — Christine T Mui
(74) *Attorney, Agent, or Firm* — Haley Guiliano LLP

(57) ABSTRACT

Systems and methods for performing biological assays are provided herein. The systems and methods determine one or more characteristics of a nucleic acid amplification sample based on a modified optical property of the sample. The nucleic acid amplification sample is reacted with an optical property modifying reagent in a reaction chamber of within a sample preparation device.

17 Claims, 42 Drawing Sheets

Specification includes a Sequence Listing.

Related U.S. Application Data

(60) Provisional application No. 62/307,867, filed on Mar. 14, 2016.

(52) U.S. Cl.
CPC .............. B01L 2300/0627 (2013.01); B01L 2300/0672 (2013.01); B01L 2300/0681 (2013.01); B01L 2300/0832 (2013.01); B01L 2300/0867 (2013.01); B01L 2300/087 (2013.01); B01L 2300/14 (2013.01); B01L 2300/1822 (2013.01); B01L 2300/1827 (2013.01); B01L 2300/1877 (2013.01); B01L 2400/0478 (2013.01); B01L 2400/0487 (2013.01); B01L 2400/0683 (2013.01); B01L 2400/0694 (2013.01)

(58) Field of Classification Search
USPC .......................................................... 435/4
See application file for complete search history.

(56) References Cited

U.S. PATENT DOCUMENTS

| | | |
|---|---|---|
| 4,379,848 A | 4/1983 | Yeaw |
| 4,624,929 A | 11/1986 | Ullman |
| 4,849,340 A | 7/1989 | Oberhardt |
| 4,859,610 A | 8/1989 | Maggio |
| 4,936,682 A | 6/1990 | Hoyt |
| D334,065 S | 3/1993 | Collister |
| D371,605 S | 7/1996 | Wong et al. |
| 5,580,794 A | 12/1996 | Allen |
| 5,801,062 A | 9/1998 | Sarstedt et al. |
| 5,830,714 A | 11/1998 | Swaminathan et al. |
| 5,837,546 A | 11/1998 | Allen et al. |
| 5,888,826 A | 3/1999 | Ostgaard et al. |
| 5,922,604 A | 7/1999 | Stapleton et al. |
| 5,958,349 A | 9/1999 | Petersen et al. |
| 6,071,394 A | 6/2000 | Cheng et al. |
| 6,074,606 A | 6/2000 | Sayles |
| 6,180,395 B1 | 1/2001 | Skiffington et al. |
| 6,198,107 B1 | 3/2001 | Seville |
| 6,300,142 B1 | 10/2001 | Andrewes et al. |
| 6,336,900 B1 | 1/2002 | Alleckson et al. |
| 6,352,838 B1 | 3/2002 | Krulevitch et al. |
| D456,082 S | 4/2002 | Bouse et al. |
| 6,426,050 B1 | 7/2002 | Pham et al. |
| 6,564,968 B1 | 5/2003 | Terrell et al. |
| 6,565,808 B2 | 5/2003 | Hudak et al. |
| 6,699,384 B1 | 3/2004 | Lin et al. |
| 6,817,256 B2 | 11/2004 | Mehra et al. |
| 6,900,059 B1 | 5/2005 | Shinn et al. |
| D507,351 S | 7/2005 | Birnboim |
| 7,156,809 B2 | 1/2007 | Quy |
| 7,256,035 B1 | 8/2007 | Schnell et al. |
| D559,996 S | 1/2008 | Okamoto et al. |
| D560,812 S | 1/2008 | Powell et al. |
| D561,905 S | 2/2008 | Ramel et al. |
| D567,961 S | 4/2008 | Yajima |
| D574,507 S | 8/2008 | Muir et al. |
| 7,438,852 B2 | 10/2008 | Tung et al. |
| 7,452,667 B2 | 11/2008 | Liew et al. |
| D602,599 S | 10/2009 | Xiaowei |
| D608,885 S | 1/2010 | Sneddon et al. |
| D618,351 S | 6/2010 | Hara |
| 7,794,656 B2 | 9/2010 | Liang et al. |
| 7,850,922 B2 | 12/2010 | Gallagher et al. |
| D631,553 S | 1/2011 | Niedbala et al. |
| D659,848 S | 5/2012 | TerMaat et al. |
| D669,375 S | 10/2012 | Kao et al. |
| D675,335 S | 1/2013 | Feuerabend et al. |
| 8,372,353 B2 | 2/2013 | Lee et al. |
| D683,642 S | 6/2013 | Buesser et al. |
| D686,311 S | 7/2013 | Mori |
| D687,564 S | 8/2013 | Yang et al. |
| 8,719,989 B1 | 5/2014 | Qanaei |
| 9,034,606 B2 | 5/2015 | Tanner et al. |
| 9,074,243 B2 | 7/2015 | Tanner et al. |
| 9,074,249 B2 | 7/2015 | Tanner et al. |
| D736,403 S | 8/2015 | Hudson et al. |
| D743,571 S | 11/2015 | Jackson |
| D748,813 S | 2/2016 | Ishiguro et al. |
| D749,420 S | 2/2016 | Maggio |
| 9,278,321 B2 | 3/2016 | Dale et al. |
| D773,069 S | 11/2016 | Curry |
| 9,546,358 B2 | 1/2017 | Tanner et al. |
| D787,682 S | 5/2017 | Ockham et al. |
| D791,952 S | 7/2017 | Florescu et al. |
| 9,739,743 B2 | 8/2017 | Athanasiou et al. |
| D800,912 S | 10/2017 | Uzri et al. |
| 9,815,061 B2 | 11/2017 | Delattre et al. |
| D808,833 S | 1/2018 | Abbott et al. |
| D820,130 S | 6/2018 | Khattak et al. |
| D821,602 S | 6/2018 | Sever et al. |
| 9,999,889 B2 | 6/2018 | Khattak et al. |
| D825,772 S | 8/2018 | Sever et al. |
| D829,336 S | 9/2018 | Wohlstadter et al. |
| D829,337 S | 9/2018 | Klein et al. |
| 10,093,965 B2 | 10/2018 | Toumazou et al. |
| 10,146,909 B2 | 12/2018 | Dimov et al. |
| D838,379 S | 1/2019 | Trump |
| D840,049 S | 2/2019 | Schulz et al. |
| 10,195,606 B2 | 2/2019 | Khattak et al. |
| 10,253,357 B2 | 4/2019 | Mitra et al. |
| 10,272,434 B2 | 4/2019 | Khattak et al. |
| D854,703 S | 7/2019 | Juhlin et al. |
| D855,212 S | 7/2019 | Komuro |
| 10,343,160 B2 | 7/2019 | Lemoine et al. |
| D859,683 S | 9/2019 | Harding et al. |
| D860,472 S | 9/2019 | Blake et al. |
| D865,212 S | 10/2019 | Kakuda et al. |
| D865,218 S | 10/2019 | Mathers et al. |
| 10,449,538 B1 | 10/2019 | Carrano et al. |
| D867,584 S | 11/2019 | Zercher et al. |
| D869,311 S | 12/2019 | Khattak et al. |
| 10,545,161 B2 | 1/2020 | Khattak et al. |
| D874,677 S | 2/2020 | Stamm et al. |
| D875,963 S | 2/2020 | Gruen |
| 10,549,275 B2 | 2/2020 | Myers, III et al. |
| D879,319 S | 3/2020 | Kakuda et al. |
| D879,320 S | 3/2020 | Kakuda et al. |
| D879,994 S | 3/2020 | Leimkuehler et al. |
| 10,589,267 B2 | 3/2020 | Khattak et al. |
| 10,603,664 B2 | 3/2020 | Khattak et al. |
| D882,110 S | 4/2020 | Klein et al. |
| D883,515 S | 5/2020 | Jenoski et al. |
| D886,901 S | 6/2020 | Hussey et al. |
| D901,232 S | 11/2020 | Seymour |
| 10,843,185 B2 | 11/2020 | Gorin et al. |
| D907,232 S | 1/2021 | Reber et al. |
| D923,797 S | 6/2021 | Parks et al. |
| D928,341 S | 8/2021 | Thimm et al. |
| 11,291,995 B2 | 4/2022 | Mitra et al. |
| 2001/0012612 A1 | 8/2001 | Petersen et al. |
| 2002/0001539 A1 | 1/2002 | DiCesare et al. |
| 2002/0039783 A1 | 4/2002 | McMillan et al. |
| 2002/0042125 A1 | 4/2002 | Petersen et al. |
| 2002/0114738 A1 | 8/2002 | Wyzgol et al. |
| 2002/0191826 A1 | 12/2002 | Benett et al. |
| 2003/0064526 A1 | 4/2003 | Niedbala et al. |
| 2003/0082632 A1 | 5/2003 | Shumate |
| 2003/0123994 A1 | 7/2003 | Weng et al. |
| 2003/0157503 A1 | 8/2003 | McGarry et al. |
| 2004/0018634 A1 | 1/2004 | Hajizadeh et al. |
| 2004/0052689 A1 | 3/2004 | Yao |
| 2004/0118189 A1 | 6/2004 | Karp et al. |
| 2004/0132218 A1 | 7/2004 | Ho |
| 2004/0166569 A1 | 8/2004 | Marziali et al. |
| 2004/0203174 A1 | 10/2004 | Jones et al. |
| 2004/0208792 A1 | 10/2004 | Linton et al. |
| 2004/0209275 A1 | 10/2004 | Liew et al. |
| 2005/0022895 A1 | 2/2005 | Barth et al. |
| 2005/0106066 A1 | 5/2005 | Saltsman et al. |
| 2005/0221281 A1 | 10/2005 | Ho |

(56) References Cited

U.S. PATENT DOCUMENTS

| | | |
|---|---|---|
| 2006/0078929 A1 | 4/2006 | Bickel et al. |
| 2006/0094004 A1 | 5/2006 | Nakajima et al. |
| 2006/0166354 A1 | 7/2006 | Wikswo et al. |
| 2006/0194207 A1 | 8/2006 | Mitani et al. |
| 2006/0245977 A1 | 11/2006 | Bodner |
| 2007/0014695 A1 | 1/2007 | Yue et al. |
| 2007/0092407 A1 | 4/2007 | Xiao et al. |
| 2007/0092975 A1 | 4/2007 | Potyrailo et al. |
| 2007/0166200 A1 | 7/2007 | Zhou et al. |
| 2007/0183934 A1 | 8/2007 | Diercks et al. |
| 2007/0217963 A1 | 9/2007 | Elizarov et al. |
| 2008/0000892 A1 | 1/2008 | Hirano et al. |
| 2008/0038713 A1 | 2/2008 | Gao et al. |
| 2008/0056948 A1 | 3/2008 | Dale et al. |
| 2008/0149840 A1 | 6/2008 | Handique et al. |
| 2008/0204380 A1 | 8/2008 | Shin et al. |
| 2008/0213808 A1 | 9/2008 | Knappe |
| 2008/0233015 A1 | 9/2008 | Turner |
| 2008/0293156 A1 | 11/2008 | Smith |
| 2009/0004732 A1 | 1/2009 | LaBarre et al. |
| 2009/0048115 A1 | 2/2009 | Liew et al. |
| 2009/0071911 A1 | 3/2009 | Folden et al. |
| 2009/0151864 A1 | 6/2009 | Burke et al. |
| 2009/0203973 A1 | 8/2009 | Donoghue et al. |
| 2009/0253130 A1 | 10/2009 | Yoo |
| 2009/0305315 A1 | 12/2009 | Gandola et al. |
| 2009/0308185 A1 | 12/2009 | Wu et al. |
| 2009/0320684 A1 | 12/2009 | Weaver et al. |
| 2010/0015611 A1 | 1/2010 | Webster et al. |
| 2010/0229956 A1 | 9/2010 | Luyendijk |
| 2010/0315644 A1 | 12/2010 | Egan et al. |
| 2010/0323919 A1 | 12/2010 | Chen et al. |
| 2010/0331219 A1 | 12/2010 | Munenaka |
| 2011/0003330 A1 | 1/2011 | Durack |
| 2011/0005932 A1 | 1/2011 | Jovanovich et al. |
| 2011/0124098 A1 | 5/2011 | Rose et al. |
| 2011/0151432 A1 | 6/2011 | Zappia et al. |
| 2011/0172510 A1 | 7/2011 | Chickering, III et al. |
| 2011/0294112 A1 | 12/2011 | Bearinger et al. |
| 2011/0294205 A1 | 12/2011 | Hukari et al. |
| 2012/0040445 A1 | 2/2012 | Bouma et al. |
| 2012/0100624 A1 | 4/2012 | Hara et al. |
| 2012/0105837 A1 | 5/2012 | Ingber |
| 2012/0115248 A1 | 5/2012 | Ansyln et al. |
| 2012/0123686 A1 | 5/2012 | Xiang et al. |
| 2012/0285562 A1 | 11/2012 | Richardson |
| 2013/0003162 A1 | 1/2013 | Leoni et al. |
| 2013/0112296 A1 | 5/2013 | Lee et al. |
| 2013/0130232 A1 | 5/2013 | Weibel et al. |
| 2013/0130267 A1 | 5/2013 | Luedke et al. |
| 2013/0244241 A1 | 9/2013 | Carrera Fabra et al. |
| 2013/0266948 A1 | 10/2013 | Bird et al. |
| 2013/0280725 A1 | 10/2013 | Ismagilov et al. |
| 2013/0295663 A1 | 11/2013 | Weight et al. |
| 2013/0323738 A1 | 12/2013 | Tanner et al. |
| 2013/0323793 A1 | 12/2013 | Tanner et al. |
| 2014/0031248 A1 | 1/2014 | Tanner et al. |
| 2014/0057210 A1 | 2/2014 | Malik et al. |
| 2014/0057268 A1 | 2/2014 | Tanner et al. |
| 2014/0073013 A1 | 3/2014 | Gorman et al. |
| 2014/0073043 A1 | 3/2014 | Holmes |
| 2014/0170661 A1 | 6/2014 | Lamura et al. |
| 2014/0188089 A1 | 7/2014 | Midgette et al. |
| 2014/0228773 A1 | 8/2014 | Burkholz |
| 2014/0242612 A1 | 8/2014 | Wang et al. |
| 2014/0335505 A1 | 11/2014 | Holmes |
| 2014/0356874 A1 | 12/2014 | Bearinger |
| 2015/0024436 A1 | 1/2015 | Eberhart et al. |
| 2015/0111201 A1 | 4/2015 | Ozcan et al. |
| 2015/0132795 A1 | 5/2015 | Griswold et al. |
| 2015/0151300 A1 | 6/2015 | Williams et al. |
| 2015/0154449 A1 | 6/2015 | Ito et al. |
| 2015/0182966 A1 | 7/2015 | Coursey |
| 2015/0218613 A1 | 8/2015 | De Forest et al. |
| 2015/0240293 A1 | 8/2015 | Tanner et al. |
| 2015/0247190 A1 | 9/2015 | Ismagilov et al. |
| 2015/0298118 A1 | 10/2015 | Chard et al. |
| 2015/0321193 A1 | 11/2015 | Sprague et al. |
| 2015/0328638 A1 | 11/2015 | Handique et al. |
| 2015/0359458 A1 | 12/2015 | Erickson et al. |
| 2016/0016171 A1 | 1/2016 | Goel |
| 2016/0077015 A1 | 3/2016 | Holmes et al. |
| 2016/0194685 A1 | 7/2016 | Unger et al. |
| 2016/0216287 A1 | 7/2016 | Holmes et al. |
| 2016/0256870 A1 | 9/2016 | Ismagilov et al. |
| 2016/0275149 A1 | 9/2016 | Majumdar et al. |
| 2016/0288121 A1 | 10/2016 | Ismagilov et al. |
| 2016/0334403 A1 | 11/2016 | Gibbons et al. |
| 2017/0044599 A1 | 2/2017 | Mitra et al. |
| 2017/0327867 A1 | 11/2017 | Dohale et al. |
| 2018/0293350 A1 | 10/2018 | Dimov et al. |
| 2018/0372595 A1 | 12/2018 | Pais et al. |
| 2019/0050988 A1 | 2/2019 | Dimov et al. |
| 2019/0060895 A1 | 2/2019 | Myers, III et al. |
| 2019/0076841 A1 | 3/2019 | Myers, III et al. |
| 2019/0083975 A1 | 3/2019 | Mitra et al. |
| 2019/0094114 A1 | 3/2019 | Myers, III et al. |
| 2019/0309356 A1 | 10/2019 | Mitra et al. |
| 2019/0314810 A1 | 10/2019 | Khattak et al. |
| 2020/0030798 A1 | 1/2020 | Mitra et al. |
| 2020/0122142 A1 | 4/2020 | Myers, III et al. |
| 2020/0164373 A1 | 5/2020 | Khattak et al. |
| 2020/0290035 A1 | 9/2020 | Samsoondar |
| 2020/0323474 A1 | 10/2020 | McIntosh |
| 2021/0378643 A1 | 12/2021 | Roswech et al. |

FOREIGN PATENT DOCUMENTS

| | | | |
|---|---|---|---|
| CN | 101297189 A | 10/2008 | |
| CN | 101821619 A | 9/2010 | |
| CN | 102395431 A | 3/2012 | |
| CN | 102439717 A | 5/2012 | |
| CN | 102811754 A | 12/2012 | |
| CN | 104374932 A | 2/2015 | |
| CN | 104870652 A | 8/2015 | |
| CN | 104937108 A | 9/2015 | |
| CN | 105142789 A | 12/2015 | |
| CN | 105441312 A | 3/2016 | |
| CN | 201930535293.7 | 4/2020 | |
| EP | 0056241 A1 | 7/1981 | |
| EP | 0520408 A2 | 12/1992 | |
| EP | 1557673 A1 | 7/2005 | |
| EP | 1581652 A2 | 10/2005 | |
| EP | 1661988 A1 | 5/2006 | |
| EP | 1964927 A1 | 9/2008 | |
| EP | 2251435 A1 | 11/2010 | |
| EP | 2528687 A2 | 12/2012 | |
| EP | 1 557 673 B1 * | 4/2015 | ............ G01N 35/08 |
| EP | 2888374 A1 | 7/2015 | |
| EP | 3134553 A1 | 3/2017 | |
| IN | 287440 | 8/2019 | |
| JP | 62-151198 A | 7/1987 | |
| JP | 2001-515216 A | 9/2001 | |
| JP | 2002-243748 A | 8/2002 | |
| JP | 2004-150804 A | 5/2004 | |
| JP | 2006-506979 A | 3/2006 | |
| JP | 2006-518449 A | 8/2006 | |
| JP | 2007-089591 A | 4/2007 | |
| JP | 2008-173218 A | 7/2008 | |
| JP | 2010-061383 A | 3/2010 | |
| JP | 2010-538801 A | 12/2010 | |
| JP | 2013-526867 A | 6/2013 | |
| JP | 2013-532488 A | 8/2013 | |
| JP | 2013-228350 A | 11/2013 | |
| JP | 2014-142361 A | 8/2014 | |
| JP | 2015-532593 A | 11/2015 | |
| JP | 2016-500002 A | 1/2016 | |
| JP | 2016-075687 A | 5/2016 | |
| JP | 2016-522676 A | 8/2016 | |
| JP | 2017-513531 A | 6/2017 | |
| KR | 10-0800436 B1 | 2/2008 | |
| KR | 10-2013-0022258 A | 3/2013 | |
| KR | 10-1439982 B1 | 9/2014 | |
| WO | 1997/011723 A1 | 4/1997 | |

(56) References Cited

FOREIGN PATENT DOCUMENTS

| WO | 1997/012681 A1 | 4/1997 | | |
|---|---|---|---|---|
| WO | 1997/041421 A1 | 11/1997 | | |
| WO | 99/09042 A2 | 2/1999 | | |
| WO | 2004/024892 A2 | 3/2004 | | |
| WO | 2005/012518 A1 | 2/2005 | | |
| WO | 2008/060604 A2 | 5/2008 | | |
| WO | 2008/107014 A1 | 9/2008 | | |
| WO | 2009/033178 A1 | 3/2009 | | |
| WO | 2009/039259 A1 | 3/2009 | | |
| WO | 2009/113010 A1 | 9/2009 | | |
| WO | 2009/125227 A1 | 10/2009 | | |
| WO | 2010/091080 A2 | 8/2010 | | |
| WO | 2010/119377 A1 | 10/2010 | | |
| WO | 2010/132453 A2 | 11/2010 | | |
| WO | 2011/094577 A2 | 8/2011 | | |
| WO | 2011/110873 A1 | 9/2011 | | |
| WO | 2011/123064 A1 | 10/2011 | | |
| WO | 2011/144345 A1 | 11/2011 | | |
| WO | 2012/018741 A2 | 2/2012 | | |
| WO | 2012/045889 A1 | 4/2012 | | |
| WO | 2013/008042 A1 | 1/2013 | | |
| WO | 2013/080154 A1 | 6/2013 | | |
| WO | 2014/018828 A1 | 1/2014 | | |
| WO | 2014/019829 A1 | 2/2014 | | |
| WO | 2014/020326 A2 | 2/2014 | | |
| WO | 2014/025415 A2 | 2/2014 | | |
| WO | 2014/031783 A1 | 2/2014 | | |
| WO | 2014/055963 A1 | 4/2014 | | |
| WO | 2014/144548 A2 | 9/2014 | | |
| WO | 2015/037281 A1 | 3/2015 | | |
| WO | 2015/038717 A1 | 3/2015 | | |
| WO | 2015/112496 A2 | 7/2015 | | |
| WO | 2015/164770 A1 | 10/2015 | | |
| WO | 2015/184360 A1 | 12/2015 | | |
| WO | WO 2017/019598 A1 | * | 2/2017 | ............ A61B 10/00 |
| WO | 2017/160836 A1 | 9/2017 | | |
| WO | 2017/160838 A1 | 9/2017 | | |
| WO | 2017/160839 A1 | 9/2017 | | |
| WO | 2017/160840 A1 | 9/2017 | | |
| WO | 2018/140540 A1 | 8/2018 | | |
| WO | 2018/185573 A1 | 10/2018 | | |
| WO | 2019/055135 A1 | 3/2019 | | |
| WO | 2020/180858 A1 | 9/2020 | | |

OTHER PUBLICATIONS

U.S. Appl. No. 15/306,240, PCT/2015/027556, filed Oct. 24, 2016.
U.S. Appl. No. 16/894,694, filed Jun. 5, 2020.
U.S. Appl. No. 15/481,349, PCT/IB2018/051326, filed Apr. 6, 2017.
U.S. Appl. No. 16/081,793, PCT/US2017/022300, filed Aug. 31, 2018.
U.S. Appl. No. 17/342,533, filed Jun. 8, 2021.
U.S. Appl. No. 17/393,398, filed Aug. 3, 2021.
U.S. Appl. No. 16/081,799, PCT/US2017/022304, filed Mar. 14, 2017.
U.S. Appl. No. 16/081,802, PCT/US2017/022306, filed Aug. 31, 2018.
U.S. Appl. No. 16/155,829, filed Oct. 9, 2018.
U.S. Appl. No. 17/364,773, filed Jun. 30, 2021.
U.S. Appl. No. 16/081,800, PCT/US2017/022305, filed Aug. 31, 2018.
U.S. Appl. No. 29/674,581, filed Dec. 21, 2018.
U.S. Appl. No. 29/759,253, filed Nov. 20, 2020.
U.S. Appl. No. 29/674,582, filed Dec. 21, 2018.
U.S. Appl. No. 16/185,314, PCT/US2018/044044, filed Nov. 9, 2018.
U.S. Appl. No. 16/722,475, filed Dec. 20, 2019.
U.S. Appl. No. 17/436,903, PCT/US2020/020772, filed Sep. 7, 2021.
U.S. Appl. No. 29/736,854, filed Jun. 3, 2020.
U.S. Appl. No. 29/733,684, filed May 5, 2020.
Anonymous: "Image Enhancement and Verification Tools—ABBYY Mobile Imaging SDK," Jul. 13, 2014, 12 pages.
Cao et al., "Microfluidic Chip for Molecular Amplication of Influenza A RNA in Human Respiratory Specimens," PLoS One, Mar. 2012, vol. 7, Issue 3, pp. 1-11.
European Application No. 17767336.5, Extended European Search Report mailed Sep. 26, 2019, 14 pages.
European Application No. 17767337.3, Extended European Search Report mailed Sep. 18, 2019, 6 pages.
European Application No. 17767339.9, Extended European Search Report mailed Oct. 4, 2019, 11 pages.
European Search Report for European Patent Application No. EP 19178796.9, Oct. 9, 2019, 7 Pages.
European Search Report, International Application No. EP18780624, Dec. 4, 2020, 10 pages.
Extended European Search Report, European Published Application No. I 15557673 A1, May 25, 2021, 21 pages.
FDA Approves in-home, rapid results COVID-19 test. Online, published Nov. 18, 2020.
Foo et al., "Rapid Tests for the Diagnosis of Influenza," Australian Prescriber, vol. 32, No. 3, Jun. 2009, pp. 64-67.
Goto., M., et al., "Colorimetric detection of loop-mediated isothermal amplification reaction by using hydroxy naphthol blue", Biotechniques, Mar. 1, 2009, pp. 167-172, vol. 46, No. 3.
Non-Final Office Action for U.S. Appl. No. 15/306,240, filed Jul. 24, 2018, 8 pages.
Non-Final Office Action for U.S. Appl. No. 16/359,913, filed Oct. 1, 2019, 9 pages.
Non-Final Office Action for U.S. Appl. No. 29/674,581, filed Jan. 8, 2020, 11 pages.
Notification of Transmittal of the International Search Report and the Written Opinion of the International Searching Authority, or the Declaration, Int'l Application No. PCT/US20/20772, Jun. 10, 2020, 15 pages.
Partial Supplemental European Search Report for European Patent Application No. EP 17767338.1, Oct. 10, 2019, 15 Pages.
Patent Cooperation Treaty, International Search Report and Written Opinion of the International Searching Authority, International Patent Application No. PCT/US19/55365, Feb. 5, 2020, 20 Pages.
Patent Cooperation Treaty, International Search Report and Written Opinion of the International Searching Authority, International Patent Application No. PCT/US2015/027556, Sep. 15, 2015, 18 Pages.
Patent Cooperation Treaty, International Search Report and Written Opinion of the International Searching Authority, International Patent Application No. PCT/US2017/022300, Jul. 10, 2017, 15 Pages.
Patent Cooperation Treaty, International Search Report and Written Opinion of the International Searching Authority, International Patent Application No. PCT/US2017/022304, Jul. 25, 2017, 20 Pages.
Patent Cooperation Treaty, International Search Report and Written Opinion of the International Searching Authority, International Patent Application No. PCT/US2017/022305, Jul. 19, 2017, 20 Pages.
Patent Cooperation Treaty, International Search Report and Written Opinion of the International Searching Authority, International Patent Application No. PCT/US2017/022306, Jun. 5, 2017, 18 Pages.
PCT International Search Report and Written Opinion for PCT/IB2018/051326, Jun. 26, 2018, 15 pages.
PCT International Search Report and Written Opinion for PCT/US2018/044044, Sep. 26, 2018, 13 Pages.
Supplementary European Search Report for European Patent Application No. EP 15783787, Nov. 28, 2017, 8 Pages.
Supplementary European Search Report for European Patent Application No. EP 17767338.1, Jan. 10, 2020, 13 Pages.
Westcott, S.L., et al., "Broadband optical absorbance spectroscopy using a whispering gallery mode microsphere resonator," Review of Scientific Instruments, vol. 79, No. 3, Mar. 13, 2008, 9 Pages.
Extended European Search Report, European Published Application No. 18857052, dated May 11, 2021, 10 pages.

(56) References Cited

OTHER PUBLICATIONS

Myers, F. B. et al., A handheld point-of-care genomic diagnostic system, and PLoS One, 2013, and vol. 8(8):e70266, pp. 1-9.
Notification of Transmittal of the International Search Report and the Written Opinion of the International Searching Authority Int'l Application No. PCT/US2021/049178, dated Jan. 14, 2022.
U.S. Appl. No. 18/111,791, filed Feb. 20, 2023, Debkishore Mitra, Pending.
U.S. Appl. No. 17/393,398, filed Aug. 3, 2021, Frank B. Myers, Pending.
U.S. Appl. No. 17/677,999, filed Feb. 22, 2022, Debkishore Mitra, Allowed.
U.S. Appl. No. 17/364,773, filed Jun. 30, 2021, Ivan Krastev Dimov, Allowed.
U.S. Appl. No. 18/364,401, filed Aug. 2, 2023, Ivan Krastev Dimov, Pending.
U.S. Appl. No. 16/081,800, filed Aug. 31, 2018, Frank B Myers, Allowed.
U.S. Appl. No. 17/962,324, filed Oct. 7, 2022, Frank B. Myers, Pending.
U.S. Appl. No. 17/436,903, filed Sep. 7, 2021, Frank B Myers, Pending.
U.S. Appl. No. 18/024,245, filed Mar. 1, 2023, Clay D. Reber, Pending.

* cited by examiner

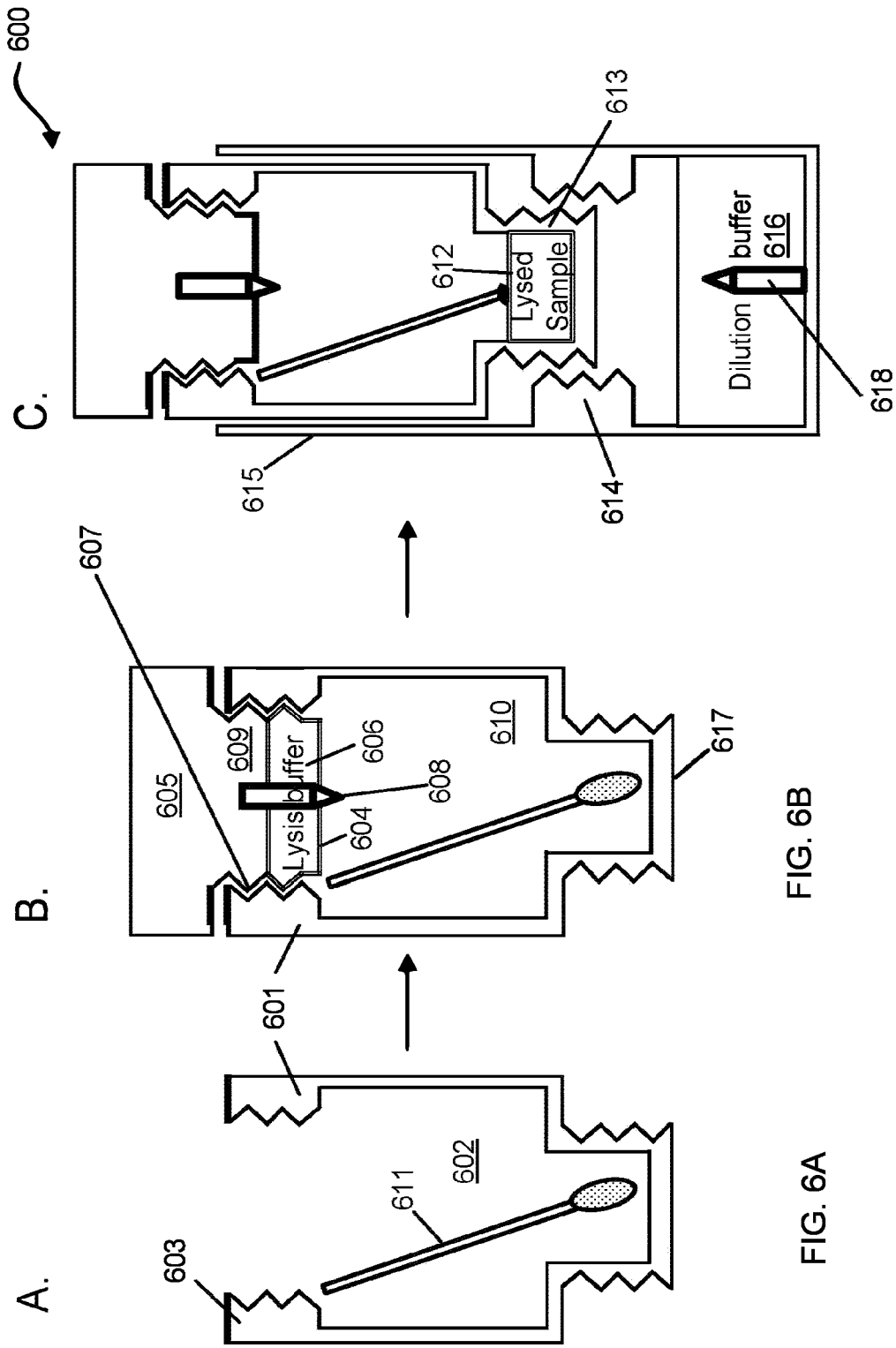

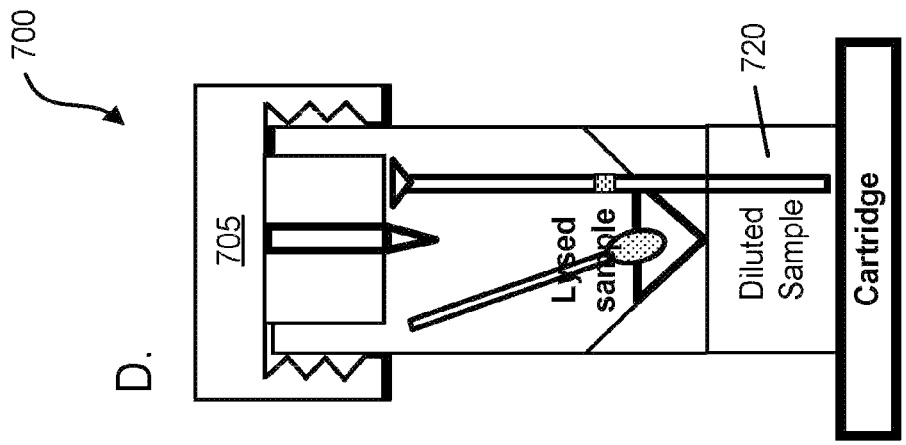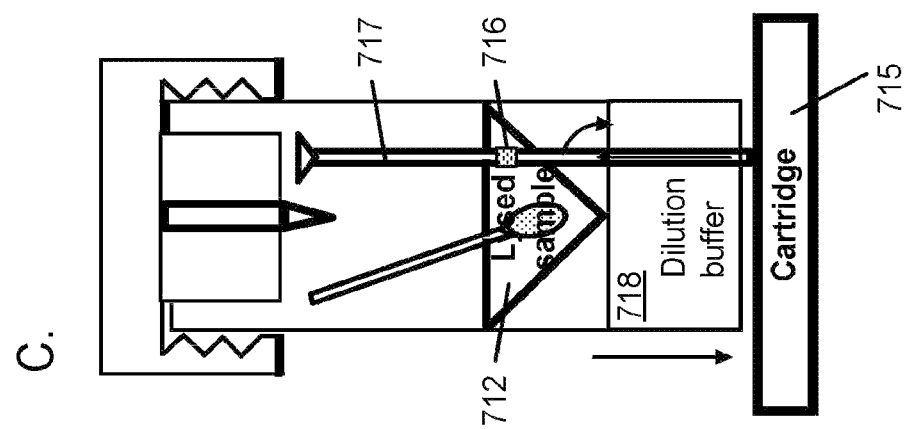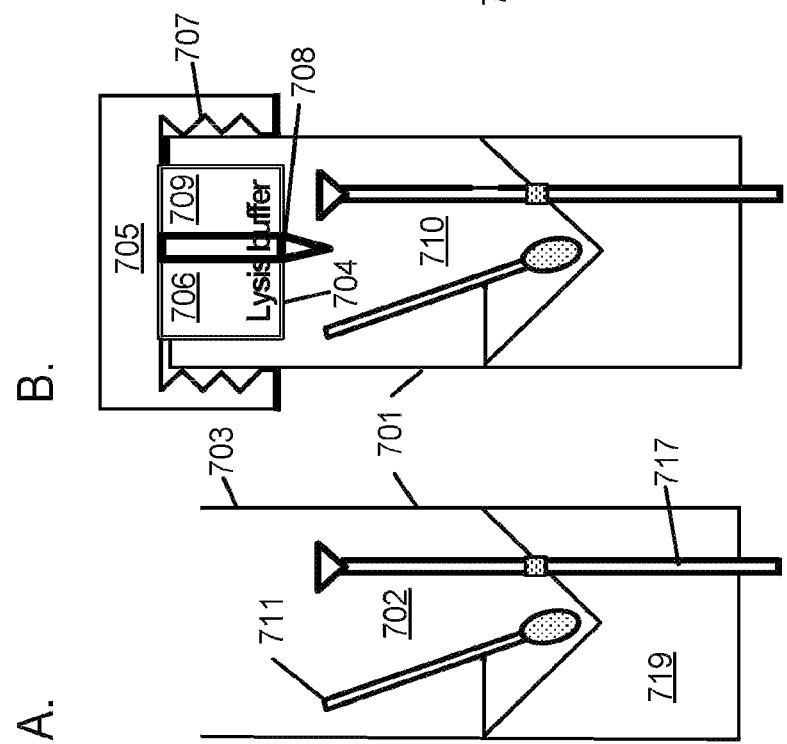

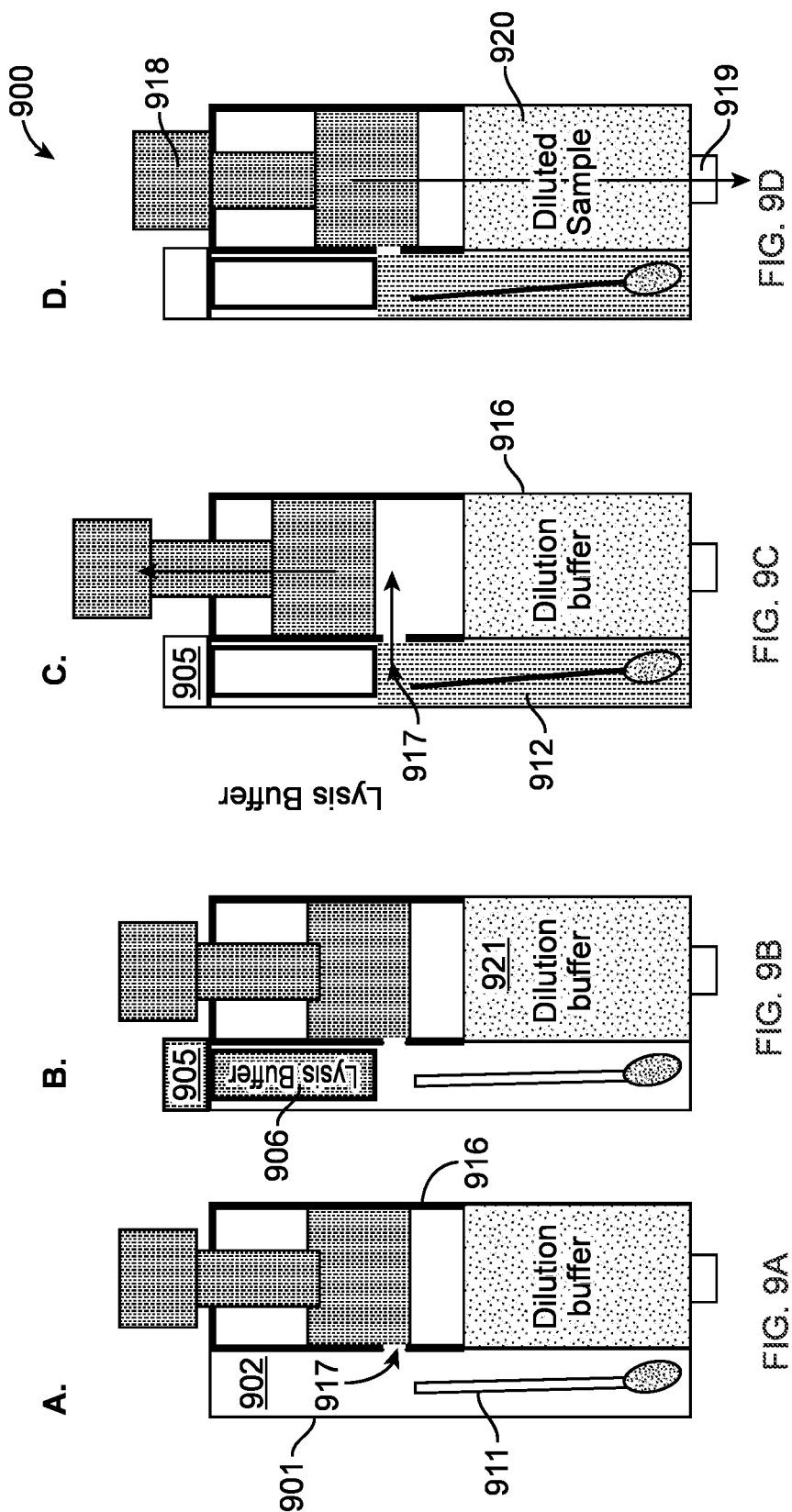

| Device | Time to Reaction | | | | | | Intra-Cartridge Statistics | |
|---|---|---|---|---|---|---|---|---|
| | 1 | 2 | 3 | 4 | 5 | 6 | Avg | StDev |
| D1 | | 21.7 | 19.3 | 16.8 | 20 | 18.5 | 19.3 | 1.8 |
| D2 | 19.4 | | 18.7 | 16.8 | 19.7 | 19 | 18.7 | 1.1 |
| D3 | 18 | 17 | | 17.6 | 18.9 | 17.9 | 17.9 | 0.7 |
| K1 | 20.5 | 17.8 | 17.8 | 17.2 | 18.9 | 18.8 | 17.8 | 0.7 |
| K2 | 18.3 | 17.5 | 16.2 | 15.4 | 16.7 | 17.7 | 17.3 | 2.0 |
| K3 | 22.2 | 19 | | 15.8 | 16.1 | 17.1 | 17.0 | 1.0 |
| B4 | 18.2 | 18.3 | 18.8 | 15.3 | 15.5 | 16.3 | 18.2 | 2.3 |
| B5 | 18 | 18.8 | 18.5 | 14.7 | 14.3 | 19.2 | 17.9 | 1.5 |
| B6 | | 19.2 | 19.7 | 19.7 | 17.9 | 17.5 | 17.1 | 2.5 |
| T4 | 22.8 | 21 | 20.4 | | | 17.5 | 19.2 | 2.2 |
| T5 | 22.7 | 21 | 19.2 | 19.2 | 16.7 | | 20.3 | 1.9 |
| T6 | | | | | | | 19.8 | 2.2 |
| Average | 19.9 | 19.1 | 19.1 | 16.9 | 17.3 | 18.0 | | |
| StDev | 2.0 | 1.6 | 1.6 | 1.7 | 1.8 | 0.9 | | |
| Inter-Cartridge Statistics | | | | | | | | |

FIG. 34

| Device | Delta E | | | | | | Intra-Cartridge Statistics | |
|---|---|---|---|---|---|---|---|---|
| | 1 | 2 | 3 | 4 | 5 | 6 | Avg | StDev |
| D1 |  | 46.4 | 61.1 | 63.6 | 57 | 56.5 | 56.9 | 6.6 |
| D2 | 36.6 | 43.4 | 36.8 | 44.1 | 35.8 | 38.9 | 38.4 | 3.4 |
| D3 | 43.9 |  |  | 52.1 | 49.9 | 47.8 | 47.4 | 3.8 |
| K1 |  | 64.3 | 63.9 | 63.3 | 66.7 | 59.1 | 63.5 | 2.9 |
| K2 | 37.2 |  | 44.3 | 52.3 | 54.2 | 51 | 47.8 | 7.0 |
| K3 | 46.6 | 47.5 |  | 56.1 | 56.8 | 51.3 | 51.7 | 4.7 |
| B4 | 44.8 | 53 | 55 |  | 59 | 52.2 | 52.8 | 5.2 |
| B5 | 47.1 | 50.3 | 50.7 | 52.1 |  | 42.8 | 48.6 | 3.7 |
| B6 | 42.5 | 47.4 | 43.5 | 53.7 | 50.8 |  | 47.6 | 4.8 |
| T4 |  | 58.5 |  |  | 62.7 | 61.1 | 60.8 | 2.1 |
| T5 | 33.1 | 36.1 | 34.5 | 34.5 |  | 35.2 | 34.7 | 1.1 |
| T6 | 29.4 | 32.3 | 38.9 | 42.7 | 46.1 |  | 37.9 | 7.0 |
| Average | 40.1 | 47.9 | 47.6 | 51.5 | 53.9 | 49.6 | | |
| StDev | 6.3 | 9.5 | 10.6 | 9.0 | 8.8 | 8.5 | | |
| Inter-Cartridge Statistics | | | | | | | | |

FIG. 35

```
                          SEQUENCE LISTING

<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
gatctgaatc cgaccaaccg                                                    20

<210> SEQ ID NO 2
<211> LENGTH: 18
<212> TYPE: DNA
<213> ORGANISM: Artificial Sequence
<220> FEATURE:
<223> OTHER INFORMATION: Primer

<400> SEQUENCE: 2
aacgcccacg ctctcgca                                                      18

<210> SEQ ID NO 3
<211> LENGTH: 41
<212> TYPE: DNA
<213> ORGANISM: Artificial Sequence
<220> FEATURE:
<223> OTHER INFORMATION: Primer

<400> SEQUENCE: 3
aaatccgtcc agtggttttt ttgaaaatcg ttgtatctcc g                            41

<210> SEQ ID NO 4
<211> LENGTH: 46
<212> TYPE: DNA
<213> ORGANISM: Artificial Sequence
<220> FEATURE:
<223> OTHER INFORMATION: Primer

<400> SEQUENCE: 4
ccgaaaccac tggacggatt tttattttta atctaaaaca aacatc                       46

<210> SEQ ID NO 5
<211> LENGTH: 121
<212> TYPE: DNA
```

```
<213> ORGANISM: Artificial Sequence
<220> FEATURE:
<223> OTHER INFORMATION: 5' to 3'

<400> SEQUENCE: 5
gatctgaatc cgaccaaccg ttctatgaaa atcgttgtat ctccgaaacc actggacgga      60
tttttatgat gtttgtttta gattatttgc gagagcgtgg gcgttaatat aaaacaagaa     120
t                                                                     121

<210> SEQ ID NO 6
<211> LENGTH: 121
<212> TYPE: DNA
<213> ORGANISM: Artificial Sequence
<220> FEATURE:
<223> OTHER INFORMATION: 3' to 5'

<400> SEQUENCE: 6
ctagacttag gctggttggc aagatacttt tagcaacata gaggctttgg tgacctgcct      60
aaaaatacta caaacaaaat ctaataaacg ctctcgcacc cgcaattata ttttgttctt     120
a                                                                     121
```

SYSTEMS AND METHODS FOR PERFORMING BIOLOGICAL ASSAYS

CROSS-REFERENCE TO RELATED APPLICATIONS

This application is a continuation of U.S. application Ser. No. 16/081,793, filed on Aug. 31, 2018, which is a 35 U.S.C. 371 national stage filing of International Application No. PCT/US2017/022300, filed on Mar. 14, 2017, which claims priority from U.S. Provisional Patent Application No. 62/307,867 filed on Mar. 14, 2016, which are hereby incorporated by reference in their entireties.

SEQUENCE LISTING

The instant application contains a Sequence Listing which has been submitted via EFS-Web and is hereby incorporated by reference in its entirety. Said ASCII copy, created on Nov. 8, 2021, is named DSS-003USC1_Sequence_Listing.txt, and is 1,756 bytes in size.

INTRODUCTION

Biological sample assays are used to evaluate one or more characteristics of biological samples. Such assays can qualitatively assess and/or quantitatively measure the presence, amount and/or functional activity of one or more analytes in a biological sample. Such an assessment can be made based on a change or lack of a change occurring in the assay. For example, a change in color and/or transmittance of a biological sample or aspect thereof occurring under specific conditions during an assay can serve as an indicator of one or more characteristics of the assayed sample.

SUMMARY OF THE INVENTION

Systems and methods for performing biological assays are provided herein. The systems and methods determine one or more characteristics of a nucleic acid amplification sample based on a modified optical property of the sample.

The subject disclosure includes system for performing one or more biological assay. Such systems include, in various embodiments one or more sample preparation device including: a sample receiving module having a fluid container including a preparation solution and/or a cap removably coupleable to the sample receiving module and including a pressurizing component for pressurizing the sample receiving module.

The systems can also include one or more optical property modifying device operatively coupleable to the sample preparation device. Such a device can include a sample receiving cartridge including one or more reaction chambers each including an optical property modifying reagent. Optical property modifying devices can also include a substrate including a heating element, and/or an adhesive layer operatively connecting the sample receiving cartridge and the substrate and thereby forming a wall of each of the one or more reaction chambers. Additionally, in some versions, when the sample preparation device is operatively coupled to the sample preparation device, the sample receiving module is configured to depressurize by transmitting at least a portion of the preparation solution into the one or more reaction chambers.

The subject disclosure also includes methods of determining one or more characteristics of a nucleic acid amplification sample based on a modified optical property of the sample. Such methods include introducing collecting a biological sample. The methods also can include inserting the biological sample including a nucleic acid into a nucleic acid preparation solution of a sample receiving module of a sample preparation device to produce a prepared nucleic acid amplification sample.

According to aspects, of the methods, the methods can also include pressurizing the sample receiving module and/or operatively coupling the sample preparation device with a nucleic acid amplification sample optical property modifying device. The methods also include, in various embodiments, depressurizing the sample receiving module by transmitting a portion of the prepared nucleic acid amplification sample out of the sample receiving module and into one or more reaction chambers of the optical property modifying device, wherein the chambers include an optical property modifying reagent and an amplification composition, and thereby generating a nucleic acid reaction mixture.

In some versions, the methods include heating the reaction mixture with a heating element of the optical property modifying device, wherein the heating accelerates a nucleic acid amplification reaction including the nucleic acid and the amplification composition, the reaction generating an amplified nucleic acid and a plurality of protons. The methods can also include reacting the protons with the optical property modifying reagent, wherein the reacting sufficiently modifies an optical property of the optical property modifying reagent to allow detection of the modified optical property by an un-assisted human eye. In addition, the methods include determining one or more characteristics of the sample based on the modified optical property.

BRIEF DESCRIPTION OF THE SEVERAL VIEWS OF THE DRAWINGS

FIG. 3A provides a partial cross sectional view of disclosed devices.

FIGS. 5A and 5B each includes a cross sectional view of disclosed devices.

FIGS. 6A, 6B, and 6C provide side cross sectional views of devices according to embodiments of the present disclosure.

FIGS. 7A, 7B, 7C, and 7D provide side cross sectional views of device aspects according to embodiments of the subject disclosure.

FIGS. 9A, 9B, 9C, and 9D provide side cross sectional views of devices according to embodiments of the subject disclosure.

FIG. 34 provides nucleic acid amplification reaction times across six different reaction chambers in an optical property modifying device according to embodiments of the subject disclosure.

FIG. 35 provides color changes, as measured using the CIE94 Delta-E scale, resulting from nucleic acid amplification reactions across six different reaction chambers in an optical property modifying device according to embodiments of the subject disclosure.

DETAILED DESCRIPTION OF THE INVENTION

Figure 1:
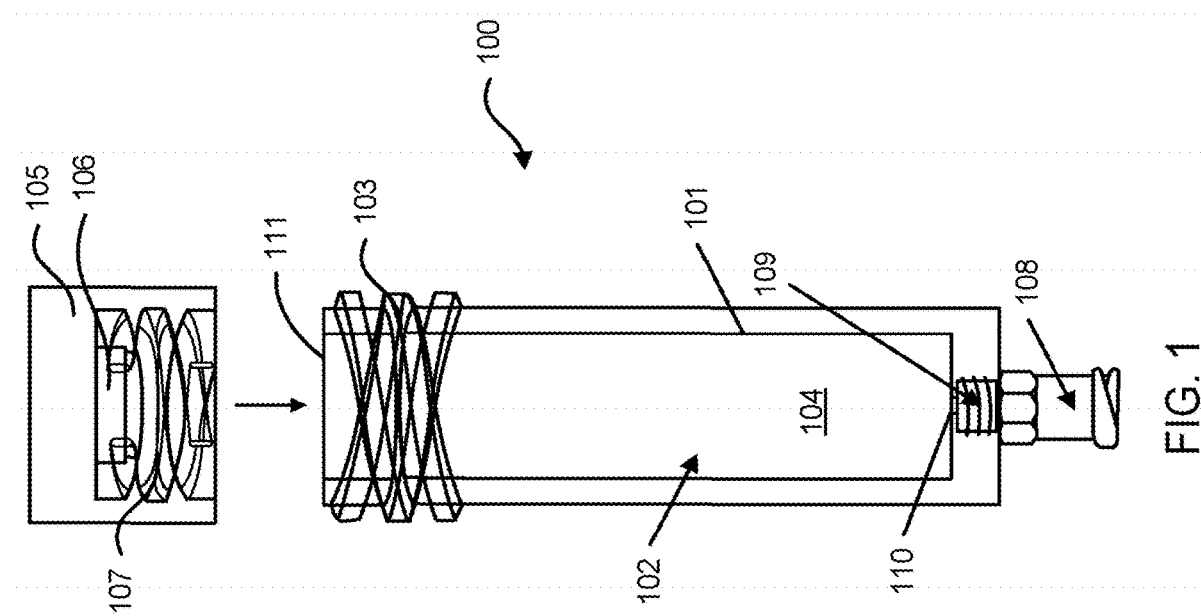
FIG. 1 provides a partial cross sectional view of a device according to embodiments of the subject disclosure.

Systems and methods for performing biological assays are provided herein. The systems and methods determine one or more characteristics of a nucleic acid amplification sample based on a modified optical property of the sample.

Before the present invention is described in greater detail, it is to be understood that this invention is not limited to particular embodiments described, as such can, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges can independently be included in the smaller ranges and are also encompassed within the invention, subject to any specifically excluded limit in the stated range. Where the stated range includes one or both of the limits, ranges excluding either or both of those included limits are also included in the invention.

Certain ranges can be presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number can be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided can be different from the actual publication dates which can need to be independently confirmed.

It is noted that, as used herein and in the appended claims, the singular forms "a," "an," and "the" include plural referents unless the context clearly dictates otherwise. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

Additionally, certain embodiments of the disclosed devices and/or associated methods can be represented by drawings which can be included in this application. Embodiments of the devices and their specific spatial characteristics and/or abilities include those shown or substantially shown in the drawings or which are reasonably inferable from the drawings. Such characteristics include, for example, one or more (e.g., one, two, three, four, five, six, seven, eight, nine, or ten, etc.) of: symmetries about a plane (e.g., a cross-sectional plane) or axis (e.g., an axis of symmetry), edges, peripheries, surfaces, specific orientations (e.g., proximal; distal), and/or numbers (e.g., three surfaces; four surfaces), or any combinations thereof. Such spatial characteristics also include, for example, the lack (e.g., specific absence of) one or more (e.g., one, two, three, four, five, six, seven, eight, nine, or ten, etc.) of: symmetries about a plane (e.g., a cross-sectional plane) or axis (e.g., an axis of symmetry), edges, peripheries, surfaces, specific orientations (e.g., proximal), and/or numbers (e.g., three surfaces), or any combinations thereof.

As will be apparent to those of skill in the art upon reading this disclosure, each of the individual embodiments described and illustrated herein has discrete components and features which can be readily separated from or combined with the features of any of the other several embodiments without departing from the scope or spirit of the present invention. Any recited method can be carried out in the order of events recited or in any other order which is logically possible.

In further describing the subject invention, subject devices for use in practicing the subject systems will be discussed in greater detail, followed by a review of associated methods.

Definitions

Terms used in the claims and specification are defined as set forth below unless otherwise specified.

The term "colorimetry" or "colorimetric" refers to techniques of quantifying or otherwise observing colored compound concentrations in solution. "Colorimetric detection" refers to any method of detecting such colored compounds and/or the change in color of the compounds in solution. Methods can include visual observation, absorbance measurements, or fluorescence measurements, among others.

The term "halochromic agent" refers to a composition that changes color upon some chemical reaction. In particular, a halochromic agent can refer to a composition that changes color with a pH change. Different halochromic agents can change colors over different pH transition ranges.

The term "transition pH range" or "pH transition range" refers to a pH range over which the color of a particular sample or compound changes. A specific transition pH range for a sample can depend on a halochromic agent in the sample (see above).

The term "nucleic acid amplification" or "amplification reaction" refers to methods of amplifying DNA, RNA, or modified versions thereof. Nucleic acid amplification includes several techniques, such as an isothermal reaction or a thermocycled reaction. More specifically, nucleic acid amplification includes methods such as polymerase chain reaction (PCR), loop-mediated isothermal amplification (LAMP), strand displacement amplification (SDA), recombinase polymerase amplification (RPA), helicase dependent amplification (HDA), multiple displacement amplification (MDA), rolling circle amplification (RCA), and nucleic acid sequence-based amplification (NASBA). The term "isothermal amplification" refers to an amplification method that is performed without changing the temperature of the amplification reaction. Protons are released during an amplification reaction: for every deoxynucleotide triphosphate (dNTP) that is added to a single-stranded DNA template during an amplification reaction, one proton ($H^+$) is released.

The term "sufficient amount" means an amount sufficient to produce a desired effect, e.g., an amount sufficient to modulate protein aggregation in a cell.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., J. Mol. Biol. 215:403-410 (1990). Software for performing BLAST analyses is publicly available through the National Center for Biotechnology Information (www.ncbi.nlm.nih.gov/).

Systems

Provided herein are various embodiments of systems for performing biological assays. Such systems can include a variety of devices including one or more biological assay sample preparation devices, which are also referred to herein as sample preparation devices, and/or optical property modifying devices. In some embodiments, the biological assay sample preparation device and optical property modifying device are operatively coupleable with one another.

By "operatively coupled," "operatively connected," and "operatively attached" as used herein, is meant connected in a specific way that allows the disclosed devices to operate and/or methods to be carried out effectively in the manner described herein. For example, operatively coupling can include removably coupling or fixedly coupling two or more aspects. Operatively coupling can also include fluidically and/or electrically and/or mateably and/or adhesively coupling two or more components. As such, devices which are operatively coupleable are devices which are capable of being operatively coupled. Also, by "removably coupled," as used herein, is meant coupled, e.g., physically and/or fluidically and/or electrically coupled, in a manner wherein the two or more coupled components can be un-coupled and then re-coupled repeatedly.

According to some versions of the subject systems, when the sample preparation device is operatively, e.g., fluidically, coupled to the sample preparation device, the sample receiving module is configured to depressurize, such as depressurize automatically without further user interaction. Such depressurization can occur by transmitting at least a portion of a preparation solution and/or a biological sample, such as a prepared biological sample, into the one or more reaction chambers. Further details of sample preparation devices, optical property modifying devices and their operation according to the subject embodiments are provided below.

Sample Preparation Devices

Various aspects of the subject disclosure include biological assay sample preparation devices. As used herein, a "biological assay" is test on a biological sample which is performed to evaluate one or more characteristics of the sample. A biological sample is a sample containing a quantity of organic material, e.g., one or more organic molecules, such as one or more nucleic acids e.g., DNA and/or RNA or portions thereof, which can be taken from a subject. Accordingly, biological assay sample preparation devices, according to some embodiments, are devices which prepare a biological sample for analysis with a biological assay. Also, in some aspects a biological sample is a nucleic acid amplification sample, which is a sample including one or more nucleic acids or portions thereof which can be amplified according to the subject embodiments.

Where appropriate, a biological sample can be collected from a subject and include one or more cells, such as tissue cells of the subject. As used herein, the term "tissue" refers to one or more aggregates of cells in a subject (e.g., a living organism, such as a mammal, such as a human) that have a similar function and structure or to a plurality of different types of such aggregates. Tissue can include, for example, organ tissue, muscle tissue (e.g., cardiac muscle; smooth muscle; and/or skeletal muscle), connective tissue, nervous tissue and/or epithelial tissue. Tissue can, in some versions, include cells from the inside of a subject's cheek and/or nose and/or throat and/or cells in a subject's saliva and/or mucus. For example, in some aspects, the biological samples are nasal, nasopharyngeal and/or mid turbinate samples.

A biological sample may also not include one or more cells. In some embodiments, a biological sample can include viral particles, free DNA, free RNA, bacteria cells or cell portions, fungi, spores, prions, or any combination thereof.

In some aspects, and as described further below, a biological sample is collected from a subject. In certain embodiments, a subject is a "mammal" or a "mammalian" subject, where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the subject is a human. The term "humans" can include human subjects of both genders and at any stage of development (e.g., fetal, neonates, infant, juvenile, adolescent, and adult), where in certain embodiments the human subject is a juvenile, adolescent or adult. While the devices and methods described herein can be applied in association with a human subject, it is to be understood that the subject devices and methods can also be applied in association with other subjects, that is, on "non-human subjects."

One version of a biological assay sample preparation device for use in practicing the subject methods is provided in FIG. 1. In various embodiments, the device 100 includes a sample receiving module 101 including a fluid container 102 for receiving one or more portions of a sample collector therein, e.g., entirely therein, a preparation solution 104, and a first attachment element 103. Such a device 100 can also include a cap 105 operatively, e.g., removably, coupleable to the sample receiving module 101 and including a pressurizing component 106, and a second attachment element 107 operatively coupleable with the first attachment element 103. In some embodiments of the devices, the pressurizing component 106 extends into and pressurizes the sample receiving module 101 for expelling fluid therefrom when the first attachment element 103 is operatively coupled to the second attachment element 107.

Figure 15:
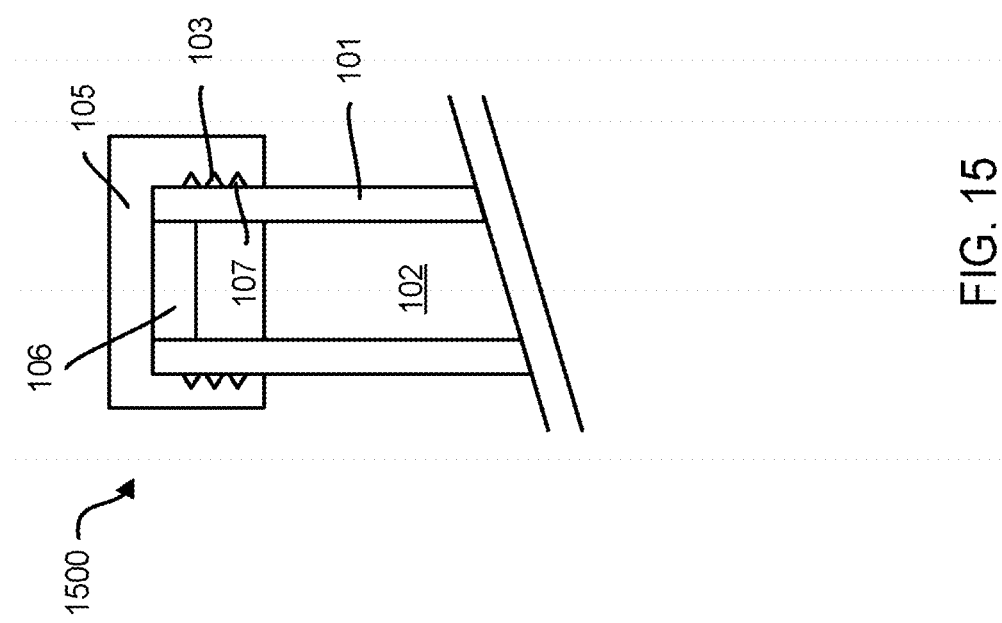
FIG. 15 provides a cross sectional view of a device according to embodiments of the present disclosure.

One portion of a biological assay sample preparation device for use in practicing the subject methods is provided in FIG. 15. The provided device 1500 portion includes many of the same elements of the embodiment shown in FIG. 1 including a cap 105 operatively, e.g., removably, coupled to the sample receiving module 101. Also provided is a fluid container 102, a first attachment element 103, and a second attachment element 107 operatively coupled with the first attachment element 103. As shown, the pressurizing component 106 extends into and pressurizes the sample receiving module 101 for expelling fluid therefrom when the first attachment element 103 is operatively coupled to the second attachment element 107.

Additionally, and as is also shown in FIG. 1, the subject devices can also include one or more valve 108, e.g., a reversibly actuable valve. The devices can also include a variety of optional components, any one or combination of which can be included in the devices, including a filter 109 for filtering one or more fluids passing through a valve 108, a first seal 110, e.g., a breakable seal, for sealing an opening at an end of the sample receiving module 101 also including a valve 108, and/or a second seal 111, e.g., a breakable seal, for sealing an opening at an end of the sample receiving module 101 which is operatively coupleable with the cap 105. A device can also include one or more re-sealable valve, e.g., a re-sealable puncture seal, e.g., a rubber septum, for sealing the opening or valve. Such a valve may be incorporated in the device at the same location but instead of a breakable seal.

Embodiments of the subject devices include a sample receiving module. Such a module can be configured to receive one or more portions of a biological sample described herein. Such a module can also be shaped, or shaped substantially, for example, as a cylinder and/or can be an elongated cylindrical tube. As used herein, "substantially" means to a great or significant extent, such as almost fully or almost entirely.

In versions wherein the sample receiving module is shaped as a cylinder, it can have a height, e.g., a height from one surface to an opposite surface, ranging from 1 cm to 50 cm, such as 1 cm to 10 cm, such as 1 cm to 5 cm, inclusive. The sample receiving module can also have a height of 50 cm or less, such as 30 cm or less, such as 20 cm or less, such as 10 cm or less, such as 5 cm or less, such as 3 cm or less, such as 1 cm or less. The sample receiving module can also have a height of 1 cm or more, such as 3 cm or more, such as 5 cm or more, such as 10 cm or more, such as 30 cm or more, such as 50 cm or more. Such a sample receiving module can also have a diameter, e.g., an outer diameter from an outer surface to an opposite outer surface, ranging from 1 mm to 5 cm, such as 1 mm to 3 cm, such as 1 mm to 1 cm, or 1 cm to 3 cm, each inclusive. Such a sample receiving module can also have a diameter, e.g., an outer diameter, of 5 cm or less, such as 3 cm or less, such as 1 cm or less, such as 5 mm or less, such as 3 mm or less, such as 1 mm or less. A sample receiving module can also have a diameter, e.g., an outer diameter, of 1 mm or more, such as 3 mm or more, such as 5 mm or more, such as 1 cm or more, such as 3 cm or more, such as 5 cm or more. A sample receiving module can also define an internal volume configured to receive any of the samples, and/or sample collectors, and/or preparation solutions described herein. Such an internal volume can range from, for example, 1 mm$^3$ to 500 cm$^3$, such as from 1 mm$^3$ to 200 cm$^3$, such as from 1 mm$^3$ to 100 cm$^3$, such as from 1 mm$^3$ to 10 cm$^3$, such as from 1 mm$^3$ to 5 cm$^3$, such as from 5 mm$^3$ to 1 cm$^3$, or from 1.5 cm$^3$ to 1 cm$^3$. A sample receiving module can also define an internal volume of 1 mm$^3$ or more, such as 1.5 cm$^3$ or more, such as 5 cm$^3$ or more, such as 1 cm$^3$ or more, such as 5 cm$^3$ or more, such as 10 cm$^3$ or more, such as 100 cm$^3$ or more, such as 200 cm$^3$ or more, such as 300 cm$^3$ or more. A sample receiving module can also define an internal volume of 500 cm$^3$ or less, such as 300 cm$^3$ or less, such as 100 cm$^3$ or less, such as 50 cm$^3$ or less, such as 10 cm$^3$ or less, such as 5 cm$^3$ or less, such as 1.5 cm$^3$ or less, such as 1 cm$^3$ or less or 5 mm$^3$ or less.

According to some aspects, a sample receiving module can have a first end, e.g., an open end having an opening which is sealable by a cap, and a second end, e.g., a closed end, opposite the first end. A first end can include a terminal flat surface which is insertable into, e.g., entirely insertable into, a cap. A pressurizing component can also be insertable into the first end of the sample receiving module. Furthermore, a second end, e.g., a closed end, can include one or more actuable valves, such as one or more reversibly actuable valves, such as reversibly actuable depressurization valves.

In various aspects, the devices include one or more valves, e.g., reversibly actuable depressurization valves. Such valves can be operatively coupleable to a reciprocating valve of an optical property modifying device to operatively couple the two devices together. Such valves can be configured to discharge fluid from a fluid container, e.g., a pressurized fluid container, therethrough when actuated. Valves according to the subject devices can be reversibly actuable between a first conformation and a second conformation. In the first conformation, the valve can provide an opening therethrough. Fluid, such as air and/or biological sample and/or a prepared sample and/or preparation solution, or any combination thereof, can pass through the opening in the valve when the valve is in the first conformation. In the second conformation, the valve is sealed and prevents the passage of fluid therethrough. The valve can be actuated from the first conformation to the second conformation by rotating the valve or a portion thereof, e.g., a first portion with respect to a second portion, such as by rotating the valve 45°, or 90° or 180° or 360° in a first rotational direction. The valve can be actuated from the second conformation to the first conformation by rotating the valve or a portion thereof, e.g., a first portion with respect to a second portion, such as by rotating the valve 45°, or 90° or 180° or 360° in a second rotational direction opposite the first rotational direction. In some versions, valves according to the subject embodiments are luer connectors, e.g., male and/or female luer connectors, and are mateably connectable to other luer connectors, e.g., male and/or female luer connectors. One or more valve according to the subject embodiments can be at an end of a sample receiving module opposite from an end attached to a cap when the sample receiving module is operatively coupled to the cap. In some versions, one or more valve according to the subject embodiments can be at an end of a sample receiving module opposite from an end at which an attachment element, e.g., a first attachment element, is positioned. Also, one or more valve according to the subject embodiments can be on a terminal flat surface of a sample receiving module and in some versions, can be centered on the surface. One or more valve according to the subject embodiments can also provide fluidic communication between a fluid container according to the subject embodiments and the environment external to the sample receiving module. The one or more valves can also include a locking element which provides tactile feedback to a user when the valve is operatively coupled to another and/or a sample preparation device is operatively coupled to an analyzing device.

In some versions, the sample receiving modules include a fluid container for containing one or more fluid, e.g., a liquid and/or a gas, and/or receiving one or more portions of a sample collector therein. Such a fluid container can be fluidically sealable such that, when sealed, fluids such as gasses and/or liquids cannot pass in or out of the container.

Where desired, sample receiving modules can include an outer surface and an interior surface defined by the one or more fluid container. Such a fluid container can extend inwardly from an opening, e.g., a circular opening, in a single flush and flat surface, e.g., a circular surface, of a sample receiving module at and end thereof. A fluid container can be configured to receive therein, e.g., entirely therein, one or more portions of a cap, e.g., a pressurizing component or an end thereof, when the cap is operatively coupled to the sample receiving module. A cap can also seal, e.g., fluidically seal, the fluid container of a sample receiving module when the cap is operatively coupled to the sample receiving module. A fluid container can be shaped as and/or define a cavity shape of a cylinder, rectangular box, pyramid, cube, or any combination thereof.

In aspects where the fluid container is shaped as a cylinder, it can have a height ranging from 1 cm to 50 cm, such as 1 cm to 10 cm, such as 1 cm to 5 cm, inclusive. The fluid container can also have a height of 50 cm or less, such as 30 cm or less, such as 10 cm or less, such as 5 cm or less, such as 3 cm or less, such as 1 cm or less. The fluid container can also have a height of 1 cm or more, such as 3 cm or more, such as 5 cm or more, such as 10 cm or more, such as 30 cm or more, such as 50 cm or more. Such a fluid container can also have a diameter ranging from 1 mm to 5 cm, such as 1 mm to 3 cm, such as 1 mm to 1 cm, or 1 cm to 3 cm, each inclusive. Such a fluid container can also have a diameter of 5 cm or less, such as 3 cm or less, such as 1 cm or less, such as 5 mm or less, such as 3 mm or less, such as 1 mm or less. A fluid container can also have a diameter of 1 mm or more, such as 3 mm or more, such as 5 mm or more, such as 1 cm or more, such as 3 cm or more, such as 5 cm or more. A fluid container can also define an internal volume configured to receive any of the samples, and/or sample collectors, and/or preparation solutions described herein. Such an internal volume can range from, for example, 1 mm$^3$ to 500 cm$^3$, such as from 1 mm$^3$ to 200 cm$^3$, such as from 1 mm$^3$ to 100 cm$^3$, such as from 1 mm$^3$ to 10 cm$^3$, such as from 1 mm$^3$ to 5 cm$^3$, such as from 5 mm$^3$ to 1 cm$^3$, or from 1.5 cm$^3$ to 1 cm$^3$. A fluid container can also define an internal volume of 1 mm$^3$ or more, such as 5 mm$^3$ or more, such as 1 cm$^3$ or more, such as 1.5 cm$^3$ or more, such as 5 cm$^3$ or more, such as 10 cm$^3$ or more, such as 100 cm$^3$ or more, such as 200 cm$^3$ or more, such as 300 cm$^3$ or more. A fluid container can also define an internal volume of 500 cm$^3$ or less, such as 300 cm$^3$ or less, such as 100 cm$^3$ or less, such as 50 cm$^3$ or less, such as 10 cm$^3$ or less, such as 5 cm$^3$ or less, such as 1.5 cm$^3$ or less, such as 1 cm$^3$ or less or 5 mm$^3$ or less.

Various embodiments of the subject sample receiving modules include one or more attachment elements, e.g., first attachment elements. An attachment element can be configured to operatively couple the cap with a sample receiving module. Such an element can be disposed on an exterior surface, e.g., entirely on an exterior surface, of a sample receiving module or a portion thereof, e.g., a body of a sample receiving module. An attachment element can specifically include one or more engagement elements for mateably coupling with a cap or a portion thereof, e.g., an attachment element. In some versions, an attachment element of a sample receiving module can include a screwable thread and/or a thread track or groove, for screwing to a reciprocating thread or thread track or groove. In some versions, an attachment element, e.g., a first attachment element or a second attachment element, includes a thread and another, e.g., a second or a first, attachment element includes a reciprocating groove for slidably receiving the thread therein. Attachment elements according to the subject embodiments can also include one or more releasing element for releasing one attachment from another and which can include one or more button and/or lever and/or switch. Attachment elements, e.g., a first attachment element, can extend around, e.g., concentrically around, a pressurizing component of a device when a cap is operatively coupled with a sample receiving module. Attachment elements, e.g., a second attachment element, can also be exclusively outside, e.g., on an external surface of, or inside, e.g., on an internal surface of, a sample receiving module or a portion thereof, e.g., a body. In other words, all portions of an attachment element can fall between at least two other portions of the sample receiving module, e.g., sample receiving module body.

In some aspects of the subject disclosure, and as noted above, the devices include a preparation solution. In some versions of the subject disclosure, the preparation solution is a nucleic acid amplification preparation solution and can include one or more buffer. A nucleic acid amplification preparation solution is a solution which prepares a biological sample such that one or more nucleic acid thereof can be amplified, e.g., amplified isothermally.

A nucleic acid amplification preparation solution can be a solution which prepares a biological sample for amplification with an isothermal amplification protocol including: transcription mediated amplification, strand displacement amplification, nucleic acid sequence-based amplification, rolling circle amplification, loop-mediated isothermal amplification, isothermal multiple displacement amplification, helicase-dependent amplification, circular helicase-dependent amplification, single primer isothermal amplification, loop-mediated amplification, or any combination thereof. Also, in some aspects, amplification is performed using a thermo-cycled reaction, such as polymerase chain reaction (PCR).

In some embodiments, a preparation solution, such as a nucleic acid amplification preparation solution, includes one or more lysing agent, such as one or more detergent. Such a lysing agent can include Dithiothreitol (DTT), detergents, e.g., TRITON X-100™, TWEEN®, Sodium dodecyl sulfate (SDS), dichlorodiphenyltrichloroethane (DDT), chaotropic salts, acids and/or bases, pH buffers, beads, solvents, or any combinations thereof. Such an agent can lyse cells of a biological sample to release nucleic acids therefrom. A preparation solution, such as a nucleic acid amplification preparation solution, can also include H$_2$O and/or one or more buffer. In various embodiments, lysing does not include heating the sample. Lysing can also be performed in 5 minutes or less, such as 10 minutes or less, such as 30 minutes or less, such as 1 hour or less.

In various aspects of the subject disclosure, the devices include one or more sample collector. A sample collector can be configured for obtaining and/or retaining a biological sample as described herein. A sample collector can also be configured for fitting into and/or being retain within, e.g., entirely within, a sample receiving module, such as a sample receiving module operatively coupled to a cap. A sample collector can be retained within, e.g., entirely within, a sample receiving module, such as a sample receiving module operatively coupled to a cap while preparing a sample and/or delivering a prepared sample as described herein.

Aspects of the subject sample collectors can extend longitudinally from a handle to a sample collection element at an end opposite the handle. A sample collector can be or include a swab, such as a cotton swab, configured for collecting and/or retaining a biological sample. Sample collectors can also be or include a scraping element for scraping a biological sample source to obtain the biological sample. A sample collector can also be or include a container, such as a sealable container for retaining a biological sample. Sample collectors according to the subject embodiments also can include one or more syringe, hollow capillary tube, punch tool, or any combination thereof.

Sample collectors can be substantially shaped as a cylinder or a rectangular box. In embodiments where the sample collector is shaped as a cylinder, it can have a height ranging from 1 cm to 50 cm, such as 1 cm to 20 cm, such as 1 cm to 10 cm, such as 1 cm to 5 cm, such as from 1 cm to 3 cm inclusive. The sample collector can also have a height of 50 cm or less, such as 30 cm or less, such as 20 cm or less, such as 10 cm or less, such as 5 cm or less, such as 3 cm or less, such as 1 cm or less. The sample collector can also have a height of 1 cm or more, such as 3 cm or more, such as 5 cm or more, such as 10 cm or more, such as 20 cm or more, such as 30 cm or more, such as 50 cm or more. Such a sample collector can also have a diameter ranging from 1 mm to 5 cm, such as 1 mm to 3 cm, such as 1 mm to 1 cm, or 1 cm to 3 cm, each inclusive. Such a sample collector can also have a diameter of 5 cm or less, such as 3 cm or less, such as 1 cm or less, such as 5 mm or less, such as 3 mm or less, such as 1 mm or less. A sample collector can also have a diameter of 1 mm or more, such as 3 mm or more, such as 5 mm or more, such as 1 cm or more, such as 3 cm or more, such as 5 cm or more. Sample collectors can also have or define a total volume ranging from, for example, 1 mm$^3$ to 200 cm$^3$, such as from 1 mm$^3$ to 100 cm$^3$, such as from 1 mm³ to 10 cm³, such as from 1 mm³ to 5 cm³, such as from 5 mm³ to 1 cm³. A sample collector can also have a volume of 1 mm³ or more, such as 5 mm³ or more, such as 1 cm³ or more, such as 5 cm³ or more, such as 10 cm³ or more, such as 100 cm³ or more, such as 200 cm³ or more. Sample collectors can also have a volume of 200 cm³ or less, such as 100 cm³ or less, such as 10 cm³ or less, such as 5 cm³ or less, such as 1 cm³ or less or 5 mm³ or less.

Embodiments of the subject devices include a cap. Such a cap can be configured to operatively couple, e.g., reversibly couple and/or sealably couple, to a sample receiving module. Accordingly, such a cap can be configured for sealing one or more opening of a sample receiving module. A cap can have a first end, e.g., an open end having an opening which defines a receptacle, and a second end, e.g., a closed and/or sealed end, opposite the first end and defined by a single flat terminal surface.

In some embodiments, a cap includes a pressurizing component and/or a cap body. A pressurizing component can be a protrusion, e.g., a cylindrical protrusion, extending from a surface, e.g., an interior surface, of the cap body. A pressurizing component can be integral with the cap body, e.g., composed of a single piece of material, or can be operatively coupled, e.g., adhesively coupled, thereto. In some versions, a pressurizing component is composed of the same material as the cap body and in other versions, the pressurizing component is composed of a different material than the cap body.

Pressuring components can include one or more biasing elements or materials which can be configured to deform from a first configuration to a second configuration and while in the second configuration, be biased to return to the first configuration. As described herein, biasing elements can deform from a first configuration to a second configuration when a cap is operatively coupled to a sample receiving module and while in the second configuration, be biased to return to the first configuration. A pressuring component can also return to a first configuration from a first configuration when a fluid is discharged from a sample receiving module. Biasing elements can exert force on a fluid in contact with the elements and can thereby pressurize the fluid.

A pressuring component according to the subject embodiments can be flexible. By "flexible," as used herein is meant pliable or capable of being bent or flexed repeatedly (e.g., bent or flexed with a force exerted by a human hand or other body part) without damage (e.g., physical deterioration). A pressuring component can also include one or more polymeric materials (e.g., materials having one or more polymers including, for example, plastic and/or rubber and/or foam) and/or metallic materials, such as metallic materials forming a spring.

Pressurizing components can be shaped as a cylinder, rectangular box, pyramid, cube, or any combination thereof. In embodiments where the pressurizing component is shaped as a cylinder, it can have a height ranging from 0.1 mm to 5 cm, such as 1 mm to 1 cm, such as 1 mm to 5 mm, inclusive. As used herein, "inclusive" refers to a provided range including each of the listed numbers. Unless noted otherwise herein, all provided ranges are inclusive. The pressurizing component can also have a height of 5 cm or less, such as 3 cm or less, such as 1 cm or less, such as 5 mm or less, such as 3 mm or less, such as 1 mm or less. The pressurizing component can also have a height of 1 mm or more, such as 3 mm or more, such as 5 mm or more, such as 1 cm or more, such as 3 cm or more, such as 5 cm or more. Such a pressurizing component can also have a diameter ranging from 1 mm to 5 cm, such as 1 mm to 3 cm, such as 1 mm to 1 cm, or 1 cm to 3 cm, each inclusive. Such a pressurizing component can also have a diameter of 5 cm or less, such as 3 cm or less, such as 1 cm or less, such as 5 mm or less, such as 3 mm or less, such as 1 mm or less. A pressurizing component can also have a diameter of 1 mm or more, such as 3 mm or more, such as 5 mm or more, such as 1 cm or more, such as 3 cm or more, such as 5 cm or more.

In aspects of the subject disclosure where a pressurizing component is shaped as a rectangular box or a cube, the pressurizing component can have a length, width, and/or height of 5 cm or less, such as 3 cm or less, such as 1 cm or less, such as 5 mm or less, such as 3 mm or less, such as 1 mm or less. A pressurizing component can also have a length, width, and/or height of 1 mm or more, such as 3 mm or more, such as 5 mm or more, such as 1 cm or more, such as 3 cm or more, such as 5 cm or more. A pressurizing component can also have a length, width, and/or height ranging from 1 mm to 5 cm, such as 1 mm to 3 cm, such as 1 mm to 1 cm, or 1 cm to 3 cm, each inclusive.

A pressurizing component can also be configured to extend into, such as fully into, and/or engage with, e.g., slidably and/or sealably engage with, a sample receiving module, or a portion thereof, such as a fluid container or a portion thereof, e.g., an internal surface defining the fluid container, when a cap is operatively coupled with the sample receiving module.

The disclosure also provides device embodiments wherein the pressurizing component extends into, e.g., extends fully into, and pressurizes the sample receiving module when the cap is operatively coupled to the sample receiving module, such as when a first attachment element is operatively coupled to a second attachment element. The pressure can be applied, for example, for expelling fluid from the sample receiving module. When desired, the sample receiving module or a fluid container thereof is sealed when the pressurizing component is inserted and extends therein.

The pressurizing component pressurizes the sample receiving module by exerting force on one or more fluid, e.g., a liquid and/or gas, within the sample receiving module, such as air and/or preparation solution. As the pressurizing component extends further into the sample receiving module, the pressure increases because the pressurizing component exerts more force on the one or more fluid. When the pressurizing component is retained in a particular position within the sample receiving module, the pressure in the module remains constant when the sample receiving module remains sealed.

According to some embodiments, the pressurizing component pressurizes the sample receiving module to a pressure, e.g., a peak pressure, ranging from 50 Pa to 50000 Pa, such as 500 Pa to 50000 Pa, such as 1000 Pa to 50000 Pa, such as 5000 Pa to 50000 Pa, such as 10000 Pa to 30000 Pa, such as 15000 Pa to 25000 Pa, each inclusive. Where desired, the pressurizing component pressurizes the sample receiving module to a pressure of 1000000 Pa or less, such as 50000 Pa or less, such as 30000 Pa or less, such as 10000 Pa or less, such as 5000 Pa or less, such as 1000 Pa or less, such as 500 Pa or less, such as 50 Pa or less. In some versions, the pressurizing component pressurizes the sample receiving module to a pressure of 1000000 Pa or more, 50000 Pa or more, 30000 Pa or more, 10000 Pa or more, or 5000 Pa or more, 1000 Pa or more, 500 Pa or more, or 50 Pa or more. As used herein, the term pressure can refer to peak pressure.

In various aspects, caps include one or more receptacle therein. Caps can include an outer surface and an interior surface defined by the one or more receptacle. Such a receptacle can extend inwardly from an opening, e.g., a circular opening, in a single flush and flat surface, e.g., a circular surface, of a cap. A receptacle can be configured to receive therein, e.g., entirely therein, one or more portions of a sample receiving module, e.g., an end of a sample receiving module and/or one or more portions of a preparation solution of a sample receiving module and/or one or more seal of a sample receiving module and/or one or more attachment elements of a sample receiving module, when the cap is operatively coupled to the sample receiving module. In some versions, a terminal end surface of a sample receiving module contacts and/or is flush against a surface of a cap, such as an internal surface, e.g., a terminal internal surface, of a cap receptacle, when the cap is operatively coupled to the sample receiving module. A cap can also seal, e.g., fluidically seal, a fluid container of a sample receiving module when the cap is operatively coupled to the sample receiving module. A receptacle can be shaped as a cylinder, rectangular box, pyramid, cube, or any combination thereof.

In instances where the receptacle is shaped as a cylinder, it can have a height ranging from 0.1 mm to 5 cm, such as 1 mm to 1 cm, such as 1 mm to 5 mm, inclusive. The receptacle can also have a height of 5 cm or less, such as 3 cm or less, such as 1 cm or less, such as 5 mm or less, such as 3 mm or less, such as 1 mm or less. The receptacle can also have a height of 1 mm or more, such as 3 mm or more, such as 5 mm or more, such as 1 cm or more, such as 3 cm or more, such as 5 cm or more. Such a receptacle can also have a diameter ranging from 1 mm to 5 cm, such as 1 mm to 3 cm, such as 1 mm to 1 cm, or 1 cm to 3 cm, each inclusive. Such a receptacle can also have a diameter of 5 cm or less, such as 3 cm or less, such as 1 cm or less, such as 5 mm or less, such as 3 mm or less, such as 1 mm or less. A receptacle can also have a diameter of 1 mm or more, such as 3 mm or more, such as 5 mm or more, such as 1 cm or more, such as 3 cm or more, such as 5 cm or more. A receptacle can also define an internal volume ranging from 1 $mm^3$ to 50 $cm^3$, from 1 $mm^3$ to 10 $cm^3$, from 1 $mm^3$ to 5 $cm^3$, such as from 5 $mm^3$ to 3 $cm^3$, such as from 5 $mm^3$ to 1 $cm^3$. A receptacle can also define an internal volume of 1 $mm^3$ or more, such as 5 $mm^3$ or more, 1 $cm^3$ or more, or 10 $cm^3$ or more. A receptacle can also define an internal volume of 50 $cm^3$ or less, such as 10 $cm^3$ or less, such as 5 $cm^3$ or less, such as 1 $cm^3$ or less or 5 $mm^3$ or less.

In some aspects of the subject embodiments, a pressurizing component is disposed within, e.g., entirely within, a receptacle of a cap. In some embodiments, a pressurizing component can extend from a circular end surface of a cylindrical receptacle toward an opposite open end of the cylindrical receptacle.

Also, in some embodiments, caps include one or more attachment element. Such an element can be disposed within, e.g., entirely within, a receptacle of a cap. Such an element can also be disposed on an exterior surface of a cap. An attachment element can be configured to operatively couple the cap with a sample receiving module. Such an attachment element can specifically include one or more engagement elements for mateably coupling with a sample receiving module. In some versions, an attachment element can include a screwable thread and/or a thread track or groove, for screwing to a reciprocating thread or thread track or groove. Attachment elements according to the subject embodiments can also include one or more releasing element for releasing one attachment from another and which can include one or more button and/or lever and/or switch. Attachment elements, e.g., a second attachment element, can extend around, e.g., concentrically around, a pressurizing component of a device. Attachment elements, e.g., a second attachment element, can also be exclusively inside, e.g., on an internal surface of, a cap or a portion thereof, e.g., a cap body. In other words, all portions of an attachment element can fall between at least two other portions of the cap, e.g., cap body.

According to the subject embodiments, the sample receiving modules and/or caps or portions thereof, e.g., pressurizing components, can each be composed of a variety of materials and can be composed of the same or different materials. The sample receiving modules and/or caps or portions thereof can be composed of polymeric materials (e.g., materials having one or more polymers including, for example, plastic and/or rubber) and/or metallic materials. Such materials can have characteristics of flexibility and/or high strength (e.g., able to withstand significant force, such as a force exerted on it by use, without breaking and/or resistant to wear) and/or high fatigue resistance (e.g., able to retain its physical properties for long periods of time regardless of the amount of use or environment).

Materials of interest of which any of the device components described herein can be composed include, but are not limited to: polymeric materials, e.g., plastics and/or elastomers, such as polytetrafluoroethene or polytetrafluoroethylene (PFTE), including expanded polytetrafluoroethylene (e-PFTE), polyester (Dacron™), nylon, polypropylene, polyethylene, high-density polyethylene (HDPE), polyurethane, etc., metals and metal alloys, e.g., titanium, chromium, stainless steel, etc., and the like.

According to some aspects, the subject devices and components thereof, e.g., sample receiving modules and/or caps, are hand-held devices. As used herein, the term "hand-held" refers to the characteristic ability of an aspect to be held (e.g., retained, or easily or comfortably held) in a hand, such as the hand of a mammal, such as the hand of a human, such as the hand of an adult male or female human of an average size and/or strength. As such, a hand-held aspect is an aspect that is sized and/or shaped to be retained (e.g., easily or comfortably retained) in the hand of a human. A hand-held aspect can also be an aspect that can be moved (e.g., easily moved, such as easily moved in a vertical and/or horizontal direction) by a human (e.g., one or two hands of a human).

In some versions, and as noted above, the subject devices can include a variety of optional components, any one or combination of which can be included in the devices, including a filter for filtering one or more fluids passing through a valve. The filter can be a porous membrane and/or a gel and/or a sponge material and can be selectively permeable. Such a filter can have a porosity such that it filters cellular components, such as cellular membranes from a prepared sample when the prepared sample flows through the filter. The filter can also have a porosity such that it traps and/or concentrates particles, e.g., bacteria, from a sample. As such, the subject methods as provided below can include concentrating one or more particles, e.g., particles in a sample fluid, by flowing a liquid, e.g., a sample fluid, through the filter. A filter can have a pore size ranging from 1 µm to 100 µm, 1 µm to 50 µm, 1 µm to 25 µm, 1 µm to 15 µm, such as 1 µm to 10 µm, such as 1 µm to 5 µm, or 100 µm or less, or 50 µm or less, or 15 µm or less or 10 µm or less or 5 µm or less. A filter can also be mounted within, e.g., entirely within, a wall of a sample receiving module and can be at an end of a sample receiving module opposite an end operatively connectable to a cap. Filters, according to the subject embodiments, can be part of or positioned within the one or more valves described herein.

Various embodiments of the disclosed devices also include a first seal e.g., a breakable seal and/or a frangible seal, for sealing an opening at an end of the sample receiving module through which fluid can flow out of the module via the valve. The seal can be positioned between, such as between in a path of fluid flow when fluid is flowing out of the sample receiving module, a filter and a valve, as such components are described herein. A first seal can be punctured by actuating a valve of a pressurized sample receiving module. Pressurized fluid from a pressurized sample receiving module can exert sufficient force on a seal to break it and flow through the created opening.

Where desired, embodiments of the disclosed devices also include a second seal e.g., a breakable seal and/or a frangible seal, for sealing an opening at an end of the sample receiving module which operatively couples to a cap. A second seal can provide a fluidic seal to a fluid container. Such a seal can be broken by exerting force on it with a sample collector and thus creating an opening in the seal through which the sample collector or a portion thereof can be inserted. A second seal can also be broken by operatively coupling a cap to a sample receiving module. Such an action can cause a pressurizing component to exert sufficient force on the seal to puncture it.

A seal, such as a first and/or second seal, can be a layer of material, such as a polymeric and/or metallic material as such materials are described herein. In some versions, a seal is a foil sheet composed of aluminum and/or other metals. A seal, as described herein, can have a thickness of 1 mm or less, such as 0.5 mm or less, such as 0.1 mm or less.

Figure 2:
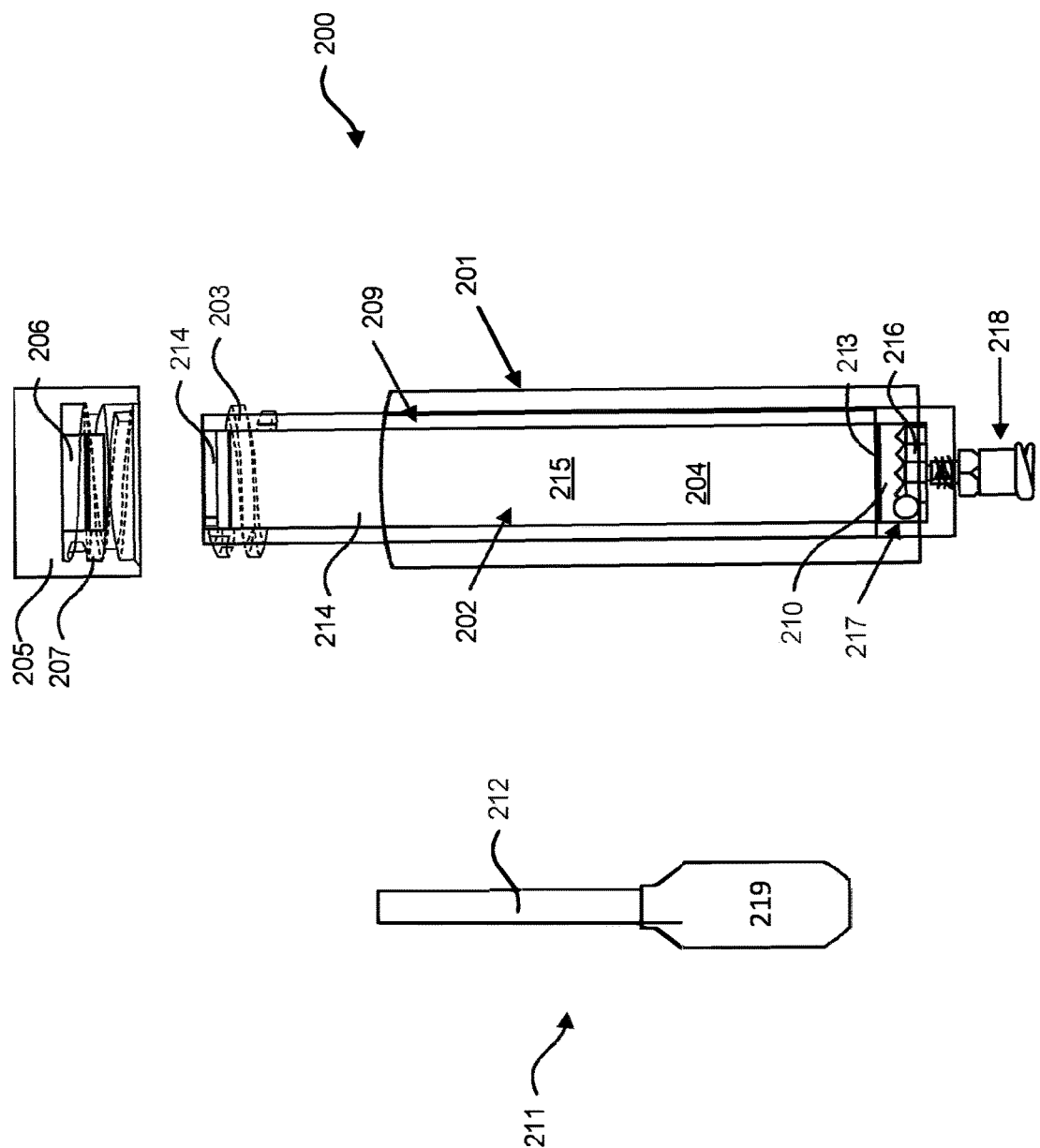
FIG. 2 provides a partial cross sectional view of a device according to embodiments of the present disclosure.

One embodiment of a biological assay sample preparation device is provided in FIG. 2. As is shown, in some versions, the device 200 includes a sample receiving module 201 including an outer body 209 forming a first chamber 210. The sample receiving module 201 also includes a fluid container 202 for receiving one or more portions of a sample collector 211 therein, e.g., entirely therein, a preparation solution 204, and a first attachment element 203. As shown, in some versions, the fluid container 202 includes a breakable seal 213 and an inner body 214 forming a second chamber 215, wherein the inner body 214 is actuable, e.g., slidable, within the outer body 209.

As is shown, the sample collector includes a handle 212 and a sample collection portion 219. Such a device 200 can also include a cap 205 operatively, e.g., removably, coupleable to the sample receiving module 201 and including a pressurizing component 206, and a second attachment element 207 operatively coupleable with the first attachment element 203. In some embodiments of the devices, the pressurizing component 206 extends into and pressurizes the sample receiving module 201 for expelling fluid therefrom when the first attachment element 203 is operatively coupled to the second attachment element 207.

In some embodiments, the outer body 209 includes one or more piercing member 216. Also, in some aspects, the inner body 214 actuates within the outer body 209 when the cap 205 is operatively coupled to the sample receiving module 201 to break the breakable seal 213 with the one or more piercing member 216 and place the first chamber 210 in fluidic communication with the second chamber 215. Such actuation can be in a direction, e.g., a linear direction along an axis of symmetry of the device, toward the one or more piercing member 216 and/or valve 218 and/or away from the cap 205. In some versions, the outer body 209 includes a staging reagent 217 and such actuation places the staging reagent 217 in fluidic communication with the second chamber 215. In some aspects, the staging reagent 217 includes one or more lyophilized agents, such as one or more lyophilized cell lysing reagent, and placing the staging reagent 217 in fluidic communication hydrates the reagent with the preparation solution 204 and/or exposes the staging reagent 217 to the biological sample. Additionally, in some versions, a cap 205 and/or valve 217 are centered on an axis of symmetry of the sample receiving module 201 when the module 201 is operatively coupled to the cap 205.

As used herein, staging reagents are reagents that prepare a biological sample for further processing as described herein. Such reagents can be lysing agents and can be configured to create a lysate. In various aspects, the one or more staging reagents 217 include detergents, e.g., TRITON X-100™, TWEEN®, Sodium dodecyl sulfate (SDS), dichlorodiphenyltrichloroethane (DDT), chaotropic salts, Dithiothreitol (DTT), acids and/or bases, pH buffers, beads, solvents, or any combinations thereof.

Figure 3:
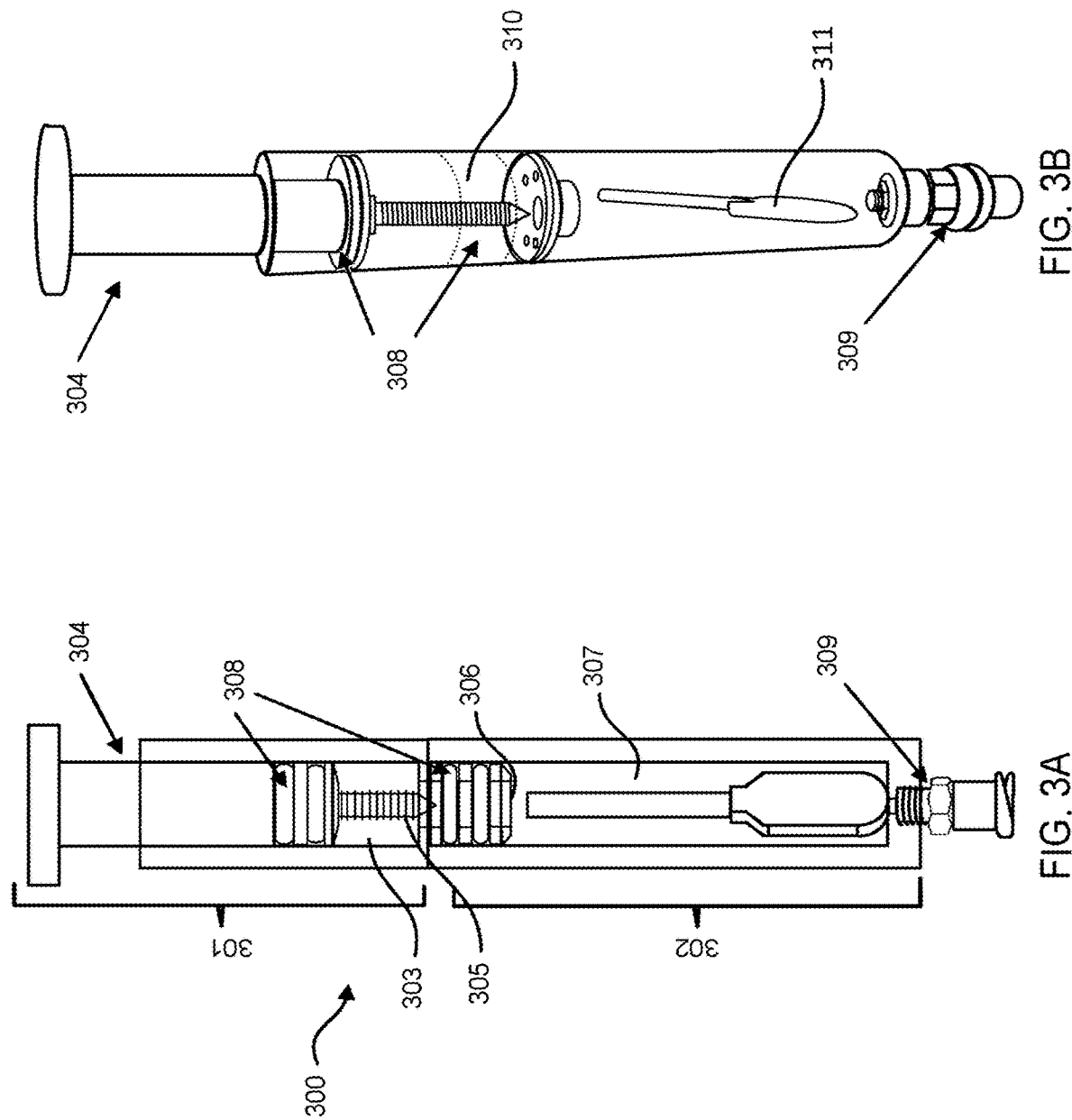
FIGS. 3A and 3B provide side views of devices according to embodiments of the subject disclosure.

In some embodiments of the subject devices, the devices include one or more plungers. Such a device is shown, for example, in FIGS. 3A, 3B and 4. Specifically, provided in these figures is a biological assay sample preparation device 300 including a cap 301 and a sample receiving module 302 which is operatively coupleable to the cap 301. As depicted, the cap 301 can include a first chamber 303, a plunger 304 including a piercing member 305, and/or a seal 306. In various embodiments, the first chamber 303 includes a preparation solution 310, such as any of the solutions described herein. Also, the sample receiving module 302 can include a second chamber 307. The second chamber 307 can be configured to receive and/or retain a sample collector 311 therein. The second chamber 307 can also include solution, such as a preparation solution and/or water and/or one or more buffer.

A cap can include a preparation solution 310 in an amount ranging from 500 µL to 1500 µL, such as from 700 µL to 1000 µL, such as from 700 µL to 900 µL. The cap can include a preparation solution in an amount of 1500 µL or less, such as 1000 µL or less, such as 800 µL or less. The cap can include a preparation solution in an amount of 600 µL or more, such as 800 µL or more, such as 1000 µL or more. The cap can include a preparation solution in an amount of 800 µL. Also, in some embodiments, the preparation solution is a buffer, such as a cell lysis buffer, and can include one or more detergents.

In some aspects, when the sample receiving module 302 is operatively coupled to the cap 301, advancing the plunger 304 pierces the seal 306 with the piercing member 305 and places the first chamber 303 in fluidic communication with the second chamber 307. As is also shown, the plunger can include one or more, e.g., two, or four, or more, O-rings 308 for sealably actuating the plunger 304 within the cap 301 and/or operatively coupling the cap 301 and the sample receiving module 302. The device 300 can also include one or more actuable valve 309 on the sample receiving module 302.

Figure 4:
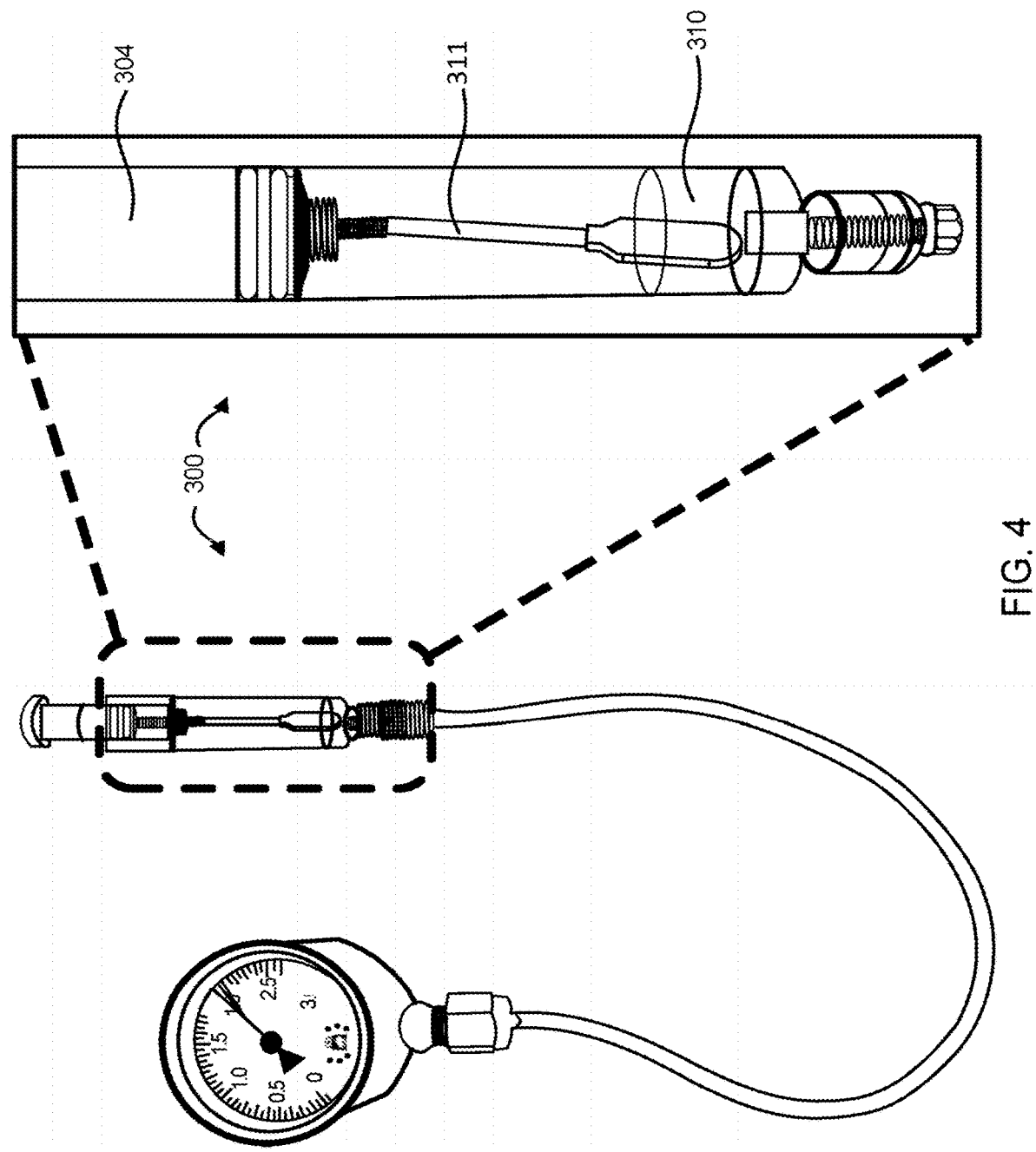
FIG. 4 provides side views of a device according to embodiments of the present disclosure.

The plunger 304 can also be a manual plunger which actuates within the first chamber 303 linearly along an axis of symmetry of the sample receiving module 302 and/or in a direction toward and/or away from a valve 309 of the device. Such a plunger 304 can be pushable directly by a user to increase pressure within the second chamber 307. The plunger 304 is shown in FIG. 4 in an advanced conformation where the plunger 304 has pushed the preparation solution 310 from the first chamber 303 into the second chamber 307. As is depicted, the plunger 304 is actuable, e.g., slidably actuable, within the cap 301 with respect to other portions of the cap 301, e.g., the cap body or housing, and as such, can move independently of the other portions. Also, as is shown, the plunger 304 is actuable, e.g., slidably actuable, within the cap 301 after the cap is first operatively coupled with the sample receiving module 302. Accordingly, operatively coupling the sample receiving module 302 and the cap 301 and then actuating the plunger 304 can be performed as two and separate steps with the subject device 300.

The user action of pressing the top of the cap 301, once it is sealed to the sample receiving module 302 forces the plunger 304 to break the seal 306 at the bottom of the cap 301, and exposes the sample collector 311 to the preparation solution 310. The pressure required for driving fluid flow is generated by the depression of the plunger 304 within the cap 301. This user action compresses fluid, e.g., preparation solution and/or biological sample, and/or air, inside the cap 301, leading to pressure generation. Subsequently, a valve 309, e.g., a luer-activated valve, of the device can be actuated and fluid, e.g., prepared sample and/or preparation solution and/or air, propelled by the pressure therethrough and out of the device. Alternatively, a valve 309 of the device can be replaced by a seal (not shown), e.g., a foil seal, e.g., a foil heat seal, which can be broken to allow fluid, e.g., prepared sample and/or preparation solution and/or air, propelled by the pressure to pass therethrough and out of the device.

The plunger 304 can be configured to reversibly actuate within the first chamber 303, such as by actuating in a first direction and/or actuating in a second direction opposite the first. Advancing the plunger 304 can pressurize the sample receiving module 302 or portion thereof, e.g., second chamber 307, to a pressure ranging from 5000 Pa to 50000 Pa, such as 10000 Pa to 40000 Pa, such as 15000 Pa to 25000 Pa, each inclusive. Where desired, the plunger pressurizes the sample receiving module to a pressure of 1000000 Pa or less, such as 50000 Pa or less, such as 40000 Pa or less, such as 10000 Pa or less, such as 5000 Pa or less. In some versions, the plunger pressurizes the sample receiving module to a pressure of 1000000 Pa or more, 50000 Pa or more, 40000 Pa or more, 10000 Pa or more, or 5000 Pa or more. As used to herein, the term pressure can refer to peak pressure.

Furthermore, any of the components of FIG. 3A, 3B, 4, 5A or 5B, such as the plunger 304, can be composed of any of the polymeric and/or metallic materials described herein, or any combinations thereof.

Figure 5A:
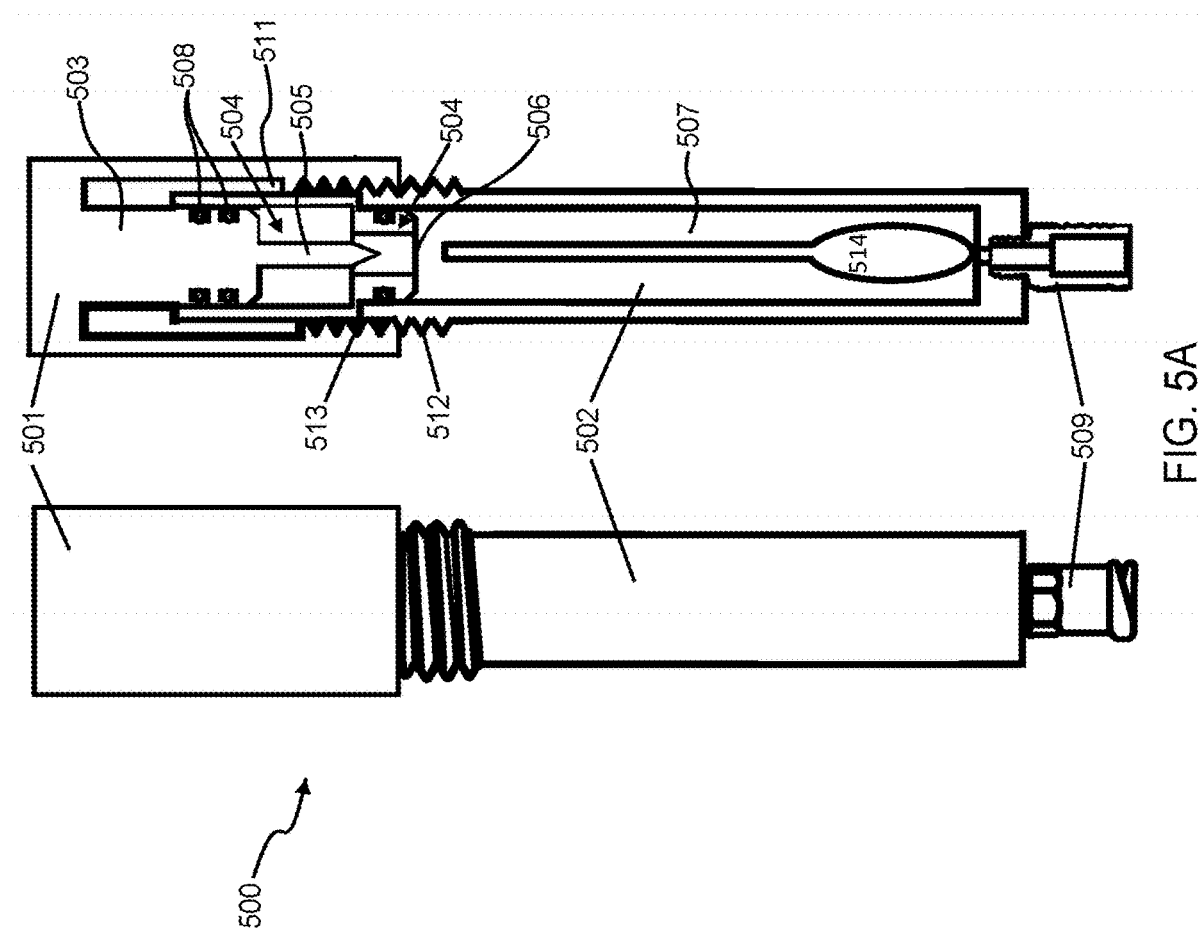
FIGS. 5A and 5B provide side views of devices according to embodiments of the subject disclosure.
Figure 5B:
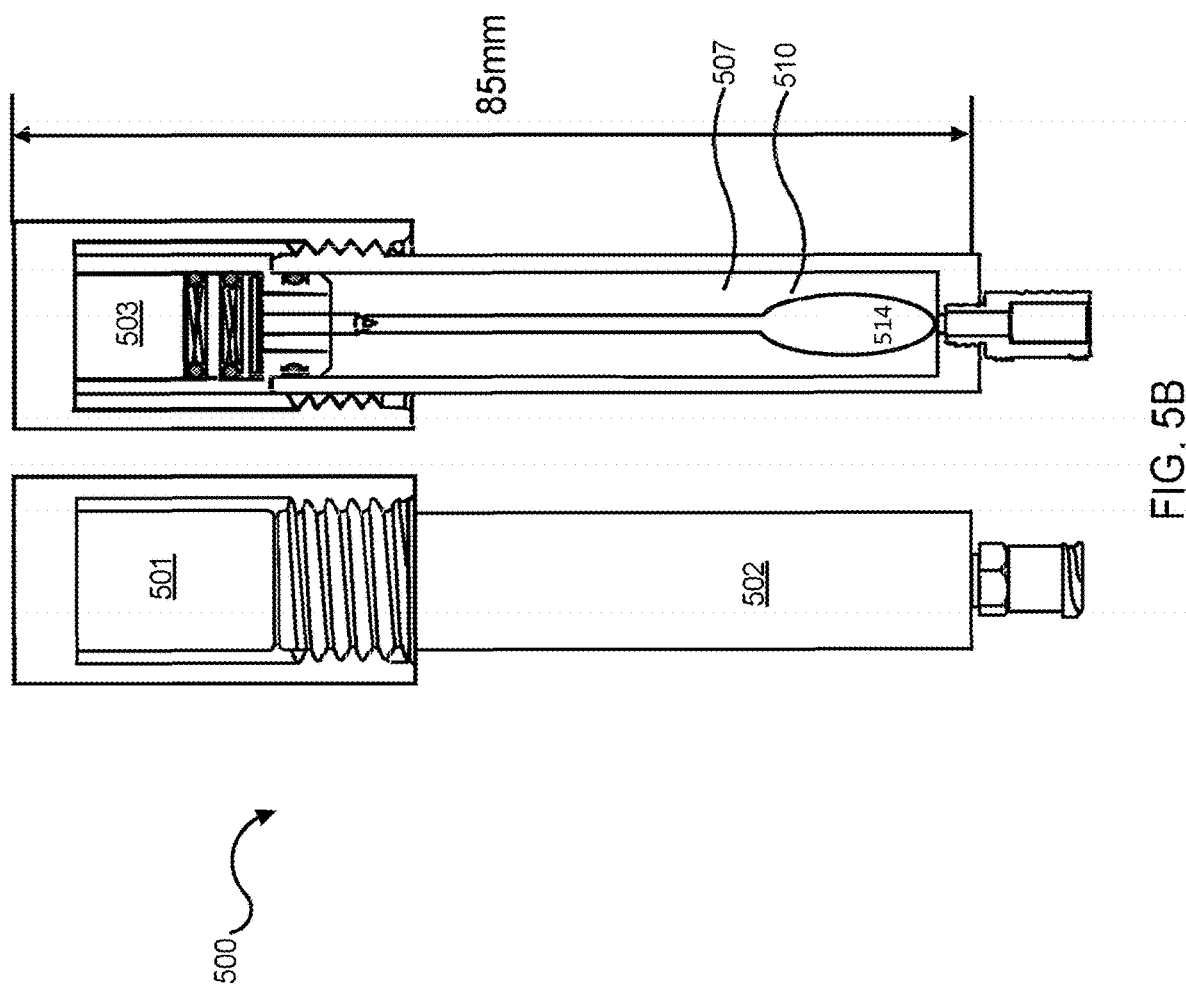

In some aspects of the subject devices, such as the device shown in FIGS. 5A and 5B, the device 500 includes one or more plunger 503 of a cap 501 which is advanced by operatively coupling, such as by screwing, the cap 501 to a sample receiving module 502. More specifically, FIG. 5A provides both side and cross-sectional side views of the device 500 in a first conformation wherein the plunger 503 is substantially un-advanced within the device 500. FIG. 5B provides both side and cross-sectional side views of the device 500 in a second conformation wherein the plunger 503 is fully advanced within the device 500.

Operatively coupling the sample receiving module 502 and the cap 501 and actuating the plunger 503 can be performed as a single concerted step with the subject device 500. In other words, operatively coupling the sample receiving module 502 and the cap 501 also advances the plunger 503 of the device 500, such as advances the plunger from the first conformation to the second conformation. Also, as is depicted, the plunger 503 is integral with at least some portions of the cap, e.g., a housing or exterior shell. In some versions, the cap 501 includes a stationary body portion 511 which sealably mates with the sample receiving module 502 and includes a protruding portion which extends into the sample receiving module 502 when the two are mated. The plunger 503, as well the portions of the cap other than the stationary body portion 511 are freely actuable, e.g., slidably actuable, with respect to and can move independently of the stationary body portion 511 when the plunger actuates. As is shown in FIGS. 5A and 5B, the stationary body portion 511 remains in a fixed position with respect to the sample receiving module 502 when the device advances from the first conformation to the second conformation.

The cap 501 of device 500 shown in FIGS. 5A and 5B also includes a first chamber 504, plunger 503, piercing member 505, and/or seal 506. In various embodiments, the first chamber 504 includes a preparation solution 510, such as any of the solutions described herein. Also, the sample receiving module 502 can include a second chamber 507. The second chamber 507 can be configured to receive and/or retain a sample collector 514 therein. The second chamber 507 can also include solution, such as a preparation solution and/or water and/or one or more buffer.

A cap can include a preparation solution in an amount ranging from 500 μL to 1500 μL, such as from 700 μL to 1000 μL, such as from 700 μL to 900 μL. The cap can include a preparation solution in an amount of 1500 μL or less, such as 1000 μL or less, such as 800 μL or less. The cap can include a preparation solution in an amount of 600 μL or more, such as 800 μL or more, such as 1000 μL or more. The cap can include a preparation solution in an amount of 800 μL. Also, in some versions, the preparation solution is a buffer, such as a cell lysis buffer, and can include one or more detergents.

In some versions, advancing the plunger 503 by operatively coupling the sample receiving module 502 and the cap 501, such as by screwing the sample receiving module 502 and the cap 501, pierces the seal 506 with the piercing member 505 and places the first chamber 504 in fluidic communication with the second chamber 507. As is also shown, the plunger can include one or more, e.g., two, or four, or more, O-rings 508 for sealably actuating the plunger 304 within the cap 501. The device 500 can also include one or more actuable valve 509 on the sample receiving module 502.

The plunger 503 can also actuates within the first chamber 504 linearly along an axis of symmetry of the sample receiving module 502 and/or in a direction toward and/or away from a valve 509 of the device. Such a plunger 503 can be advance to increase pressure within the second chamber 507. The plunger 503 is shown in FIG. 5B in an advanced conformation where the plunger 503 has pushed the preparation solution 510 from the first chamber 504 into the second chamber 507.

The subject sample receiving module 502 can also include one or more first attachment element 512. Also, a cap 501 can include one or more second attachment element 513 for operatively, e.g., reciprocally, coupling with the first attachment element 512. Such attachment elements can be configured to operatively couple the cap 501 with the sample receiving module 502. In some versions, and as shown in FIGS. 5A and 5B, a first and/or second attachment element of a sample receiving module or a cap can each include a screwable thread and/or a thread track or groove, for screwing to a reciprocating thread or thread track or groove. In some versions, an attachment element, e.g., a first attachment element or a second attachment element, includes a thread and another, e.g., a second or a first, attachment element includes a reciprocating groove for slidably receiving the thread therein.

The plunger 503 can be configured to reversibly actuate within the first chamber 504, such as by actuating in a first direction and/or actuating in a second direction opposite the first. Advancing the plunger 503 can pressurize the sample receiving module 502 or portion thereof, e.g., second chamber 507, to a pressure ranging from 5000 Pa to 50000 Pa, such as 10000 Pa to 40000 Pa, such as 15000 Pa to 25000 Pa, each inclusive. Where desired, the plunger pressurizes the sample receiving module to a pressure of 1000000 Pa or less, such as 50000 Pa or less, such as 40000 Pa or less, such as 10000 Pa or less, such as 5000 Pa or less. In some versions, the plunger pressurizes the sample receiving module to a pressure of 1000000 Pa or more, 50000 Pa or more, 40000 Pa or more, 10000 Pa or more, or 5000 Pa or more.

According to various aspects, a user action of turning the cap 501, after it is sealed to the sample receiving module 502, forces the plunger 503 to break the seal 506 at the bottom of the cap 501, and places the preparation solution 510 and the sample collector 514 in fluidic communication and in some embodiments, immerses the sample collector 514 in the preparation solution 510. According to some embodiments, the pressure required for driving fluid flow within device 500 is generated by the actuation of the plunger due to rotation of the cap 501 with respect to the sample receiving module 502. Such a user action compresses fluid, e.g., air and/or preparation solution and/or biological sample, inside the device 500, and causes pressure generation. Such pressure is maintained while the preparation solution reacts with the biological sample to produce a prepared sample. Subsequently, a valve 509, e.g., a luer-activated valve, of the device can be actuated and fluid, e.g., prepared sample and/or preparation solution and/or air, propelled by the pressure therethrough and out of the device. Alternatively, a valve 509 of the device can be replaced by a seal (not shown), e.g., a foil seal, e.g., a foil heat seal, which can be broken to allow fluid, e.g., prepared sample and/or preparation solution and/or air, propelled by the pressure to pass therethrough and out of the device. Also, in some embodiments, when the sample receiving module is operatively coupled to the cap, advancing the plunger pierces the seal with the piercing member and places the first chamber in fluidic communication with the second chamber.

An embodiment of a biological assay sample preparation device for use in practicing the subject methods is provided in FIGS. 6A-6C. The provided device 600 includes a sample receiving module 601 including a fluid container 602 for receiving one or more portions of a sample collector 611 therein, e.g., entirely therein, and a first attachment element 603. Such a device 600 can also include a cap 605 operatively, e.g., removably, coupleable to the sample receiving module 601 and including a preparation solution, e.g., a lysis buffer 606, second attachment element 607 operatively coupleable with the first attachment element 603. The sample receiving module 601, cap 605 and other provided components can have any of the characteristics or combination of characteristics of sample receiving modules, caps and/or other corresponding components described herein.

In the version shown, operatively coupling the sample receiving module 601 and the cap 605, as is shown in FIG. 6B, such as by screwing the sample receiving module 601 and the cap 605, pierces a seal 604 with a piercing member 608 and places a first chamber 609 in fluidic communication with a second chamber 610. As such, operatively coupling the sample receiving module 601 and the cap 605, such as by screwing the sample receiving module 601 and the cap 605 together, exposes preparation solution 606 to a sample on a sample collector 611 and thereby produces a prepared, e.g., lysed, sample 612.

Once the prepared, e.g., lysed, sample 612 is made, the sample receiving module 601 can be operatively coupled to a pressurizing module 615. Operatively coupling can be performed by attaching, such as by screwing, an attachment element 613 of a sample receiving module 601 and a second attachment element 614 of a pressurizing module 615. The pressurizing module 615 also includes a buffer, e.g., a dilution buffer 616. Operatively coupling the sample receiving module 601 and the pressurizing module 615, as is shown in FIG. 6C, places the prepared sample 612 in fluidic communication with the dilution buffer 616 so that the prepared sample 612 is diluted and pressurizes the sample receiving module. Thereafter, the diluted prepared sample can be delivered out of the device 600 for further analysis using the pressure within the device to push the diluted prepared sample out of the device 600.

Another embodiment of a biological assay sample preparation device for use in practicing the subject methods is provided in FIGS. 7A-7D. The provided device 700 includes a sample receiving module 701 including a fluid container 702 for receiving one or more portions of a sample collector 711 therein, e.g., entirely therein, and a first attachment element 703. Such a device 700 can also include a cap 705 operatively, e.g., removably, coupleable to the sample receiving module 701 and including a preparation solution, e.g., a lysis buffer 706, second attachment element 707 operatively coupleable with the first attachment element 703. Operatively coupling the cap 705 and the sample receiving module 701 can pressurize the sample receiving module 701. The sample receiving module 701 can also include a buffer, e.g., a dilution buffer 718 in a buffer container 719 therein. The sample receiving module 701, cap 705 and other provided components can have any of the characteristics or combination of characteristics of sample receiving modules, caps and/or other corresponding components described herein.

In the provided embodiment, operatively coupling the sample receiving module 701 and the cap 705, as is shown in FIG. 7B, such as by screwing the sample receiving module 701 and the cap 705, pierces a seal 704 with a piercing member 708 and places a first chamber 709 in fluidic communication with a second chamber 710. As such, operatively coupling the sample receiving module 701 and the cap 705, such as by screwing the sample receiving module 701 and the cap 705 together, exposes preparation solution 706 to a sample on a sample collector 711 and thereby produces a prepared, e.g., lysed, sample 712.

Once the prepared, e.g., lysed, sample 712 is made, the sample receiving module 701 can be operatively coupled to, such as by being lowered onto, a cartridge 715. Such operative coupling can actuate a fluidic communication element 717 and/or open a valve 716, e.g., poppet valve, of the fluidic communication element 717. The fluidic communication element 717 can be actuated toward the cap 705 when the cartridge 715 exerts force on it. Opening the valve 716 in turn releases the prepared sample 712 into the dilution buffer 718 in the buffer container 719 and produces a prepared diluted sample 720. Operatively coupling the sample receiving module 701 and the cartridge 715, as is shown in FIG. 7D, delivers the prepared diluted sample 720 out of the sample receiving module 703 and in to the cartridge.

An embodiment of a biological assay sample preparation device for use in practicing the subject methods is provided in FIGS. 8A-8D. The provided device 800 includes a sample receiving module 801 including a fluid container 802 for receiving one or more portions of a sample collector 811 therein, e.g., entirely therein. Such a device 800 can also include a cap 805 operatively, e.g., removably, coupleable to the sample receiving module 801 and including a preparation solution, e.g., a lysis buffer 806.

Operatively coupling the cap 805 and the sample receiving module 801 may not pressurize the sample receiving module 801 but may place the lysis buffer 806 in fluidic communication with a sample on the sample collector 811 and thereby produce a prepared, e.g., lysed, sample 812. The sample receiving module 801, cap 805 and other provided components can have any of the characteristics or combination of characteristics of sample receiving modules, caps and/or other corresponding components described herein.

The device 800 also includes a pressurizing chamber 816 operatively coupled to the sample receiving module 801 and including a valve 817, e.g., a one-way valve, to provide fluidic communication therebetween. The pressurizing chamber 816 also includes a plunger 818, e.g., a manually actuable plunger, which creates positive and/or negative pressure within the pressurization chamber 816 when actuated. The pressurizing chamber 816 also includes a buffer, e.g., a dilution buffer 821. The pressurizing chamber 816 also includes an expulsion valve 819 for expelling a diluted prepared sample 820 therefrom upon actuation of the plunger 818.

Figure 8A:
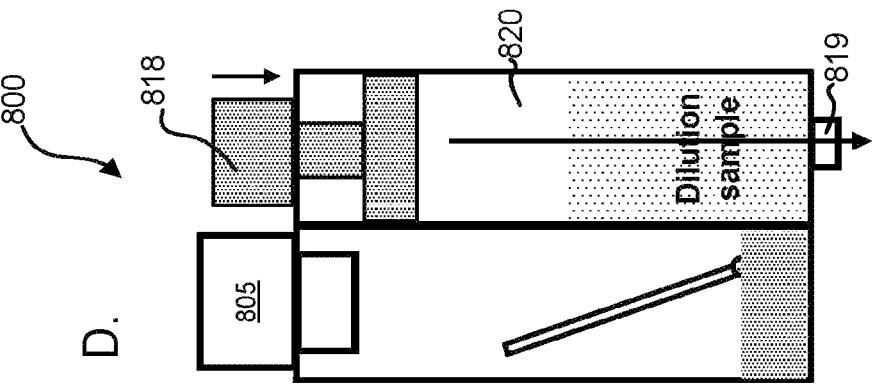
FIGS. 8A, 8B, 8C, and 8D provide side cross sectional views of devices according to embodiments of the subject disclosure.
Figure 8B:
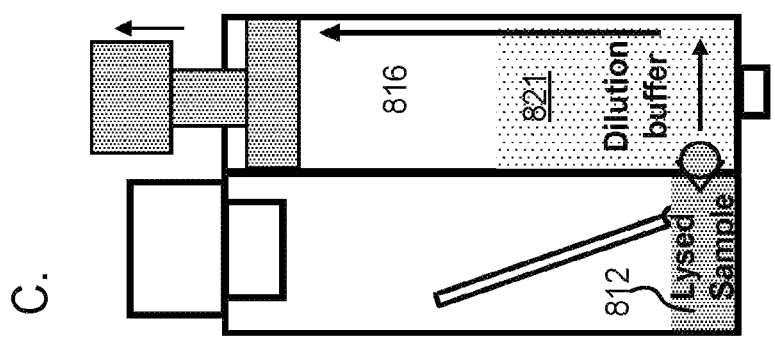
Figure 8C:
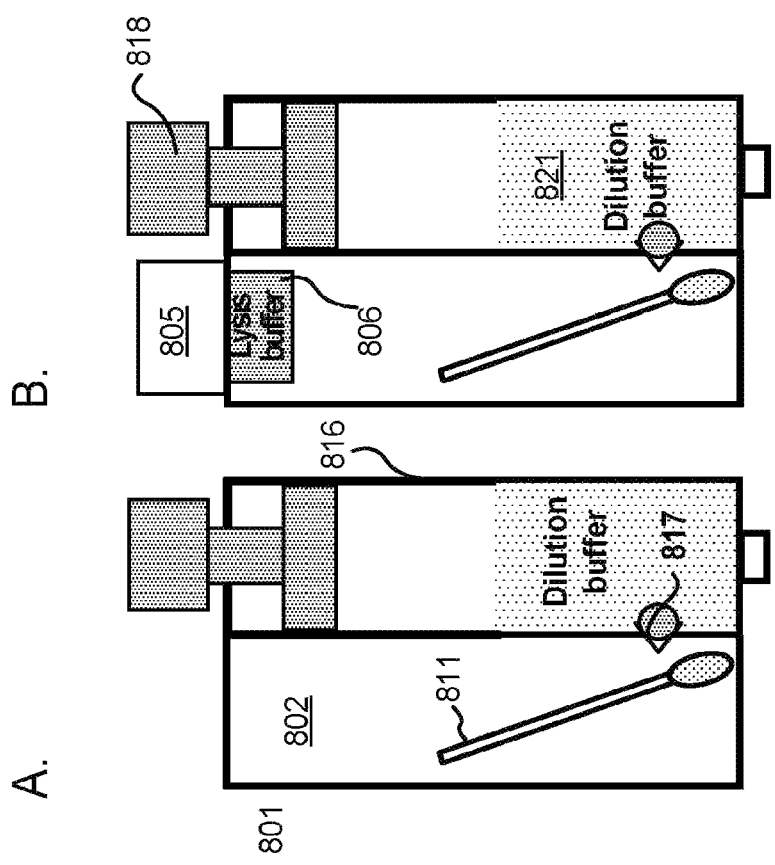
Figure 8D:
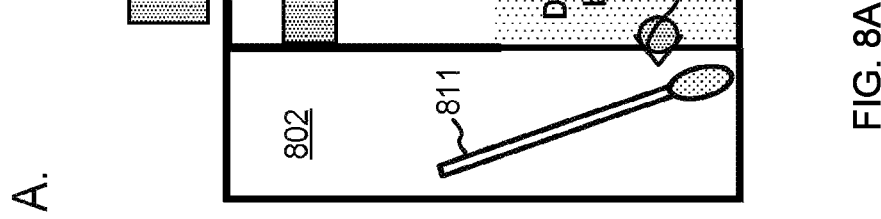

The device 800 is configured such that when the cap 805 is operatively coupled to the sample receiving module 801 to produce a prepared sample 812, the plunger 818 can be actuated in a first direction, as is shown in FIG. 8C, to propel the prepared sample 812 from the sample receiving module 801 and into the pressurizing chamber 816 via valve 817 and thereby produce a diluted prepared sample 820. The device 800 is also configured such that the plunger 818 can then be actuated in a second direction opposite the first, as is shown in FIG. 8D, to propel the diluted prepared sample 820 out of the pressurizing chamber 816 via expulsion valve 819.

Another embodiment of a biological assay sample preparation device for use in practicing the subject methods is provided in FIGS. 9A-9D. The provided device 900 includes a sample receiving module 901 including a fluid container 902 for receiving one or more portions of a sample collector 911 therein, e.g., entirely therein. Such a device 900 can also include a cap 905 operatively, e.g., removably, coupleable to the sample receiving module 901 and including a preparation solution, e.g., a lysis buffer 906.

Operatively coupling the cap 905 and the sample receiving module 901 may not pressurize the sample receiving module 901 but may place the lysis buffer 906 in fluidic communication with a sample on the sample collector 911 and thereby produce a prepared, e.g., lysed, sample 912. The sample receiving module 901, cap 905 and other provided components can have any of the characteristics or combination of characteristics of sample receiving modules, caps and/or other corresponding components described herein.

The device 900 also includes a pressurizing chamber 916 operatively coupled to the sample receiving module 901 and including an opening, e.g., a vent 917, to provide fluidic communication therebetween. The pressurizing chamber 916 also includes a plunger 918, e.g., a manually actuable plunger, which creates positive and/or negative pressure within the pressurization chamber 916 when actuated. The pressurizing chamber 916 also includes a buffer, e.g., a dilution buffer 921. The pressurizing chamber 916 also includes an expulsion valve 919 for expelling a diluted prepared sample 920 therefrom upon actuation of the plunger 918.

The device 900 is configured such that when the cap 905 is operatively coupled to the sample receiving module 901 to produce a prepared sample 912, the plunger 918 can be actuated in a first direction, as is shown in FIG. 9C, to propel the prepared sample 912 from the sample receiving module 901 and into the pressurizing chamber 916 via vent 917 and thereby produce a diluted prepared sample 920. Actuating the plunger 918 in such as direction can unseal the vent 917. The device 900 is also configured such that the plunger 918 can then be actuated in a second direction opposite the first, as is shown in FIG. 9D, to propel the diluted prepared sample 920 out of the pressurizing chamber 916 via expulsion valve 919. Actuating the plunger 918 in such as direction can seal the vent 917 and prevent further fluid communication therethrough.

Figure 10:
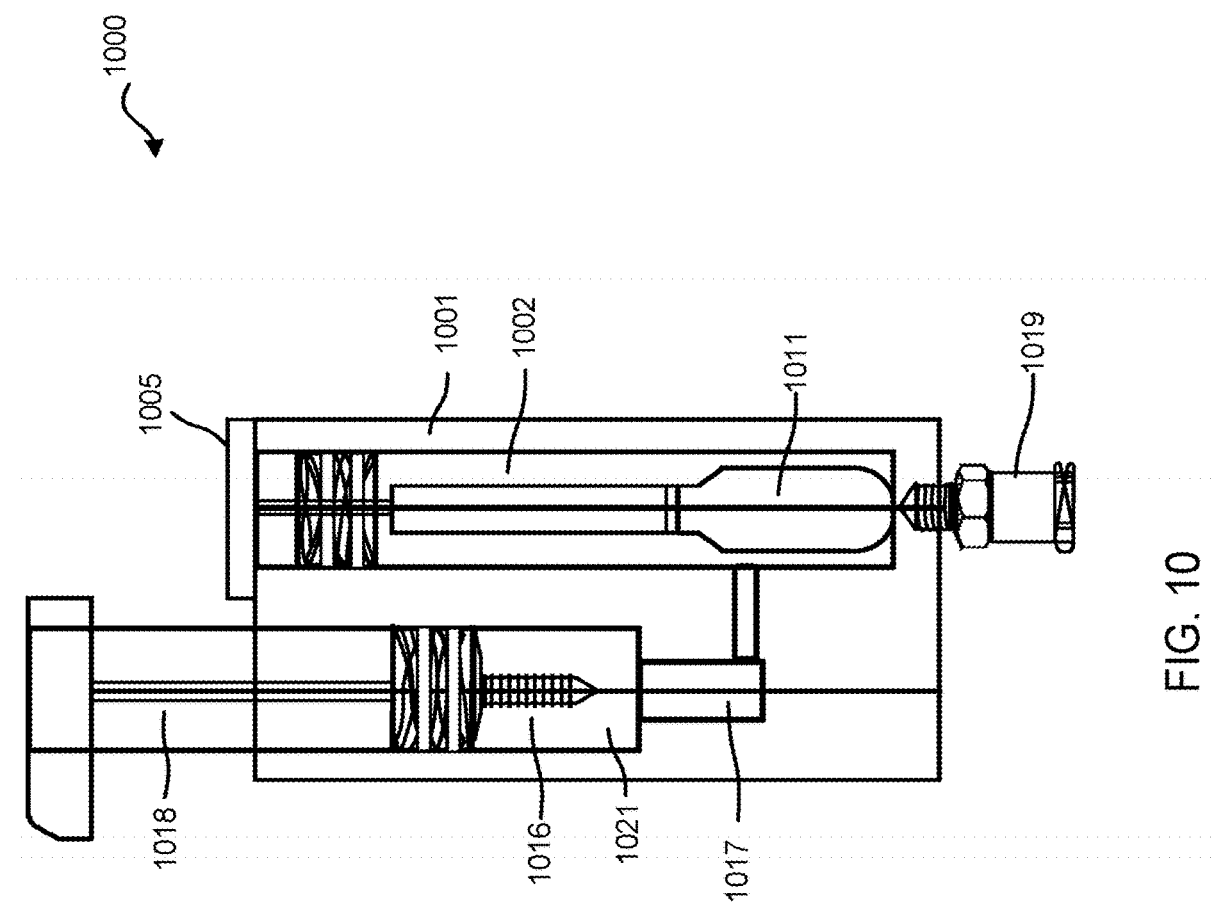
FIG. 10 provides a partial cross sectional view of a device according to embodiments of the present disclosure.

One embodiment of a biological assay sample preparation device for use in practicing the subject methods is provided in FIG. 10. The provided device 1000 includes a sample receiving module 1001 including a fluid container 1002 for receiving one or more portions of a sample collector 1011 therein, e.g., entirely therein. Such a device 1000 can also include a cap 1005 operatively, e.g., removably, coupleable to the sample receiving module 1001. The sample receiving module 1001, cap 1005 and other provided components can have any of the characteristics or combination of characteristics of sample receiving modules, caps and/or other corresponding components described herein. Operatively coupling the cap 1005 and the sample receiving module 1001 may not pressurize the sample receiving module 1001 but may place a preparation solution, e.g., a lysis buffer, in fluidic communication with a sample on the sample collector 1011 and thereby produce a prepared, e.g., lysed, sample.

The device 1000 also includes a pressurizing chamber 1016 operatively coupled to the sample receiving module 1001 and including an opening, e.g., a channel 1017 including one or more containers, such as containers including one or more buffer, to provide fluidic communication therebetween. The pressurizing chamber 1016 can be oriented in parallel to the sample receiving module 1001, e.g., can both have a central axis of symmetry oriented in the same direction with respect to that of the other. The pressurizing chamber 1016 also includes a plunger 1018, e.g., a manually actuable plunger, which operates by pushing and/or pulling in a linear direction, and which creates positive and/or negative pressure within the pressurization chamber 1016 and/or sample receiving module 1001 when actuated. The pressurizing chamber 1016 also can include a buffer, e.g., a dilution buffer 1021. The sample receiving module 1001 also includes an expulsion valve 1019 for expelling a diluted prepared sample therefrom upon actuation of the plunger 1018.

The provided device 1000 is configured such that the plunger 1018 can be actuated in a first direction, to propel a buffer from channel 1017 into the sample receiving module 1001 and thereby produce a diluted prepared sample therein and pressurize the sample receiving module. The diluted prepared sample can then be propelled by the pressure out of the sample receiving module 1001 via expulsion valve 1019.

Figure 11:
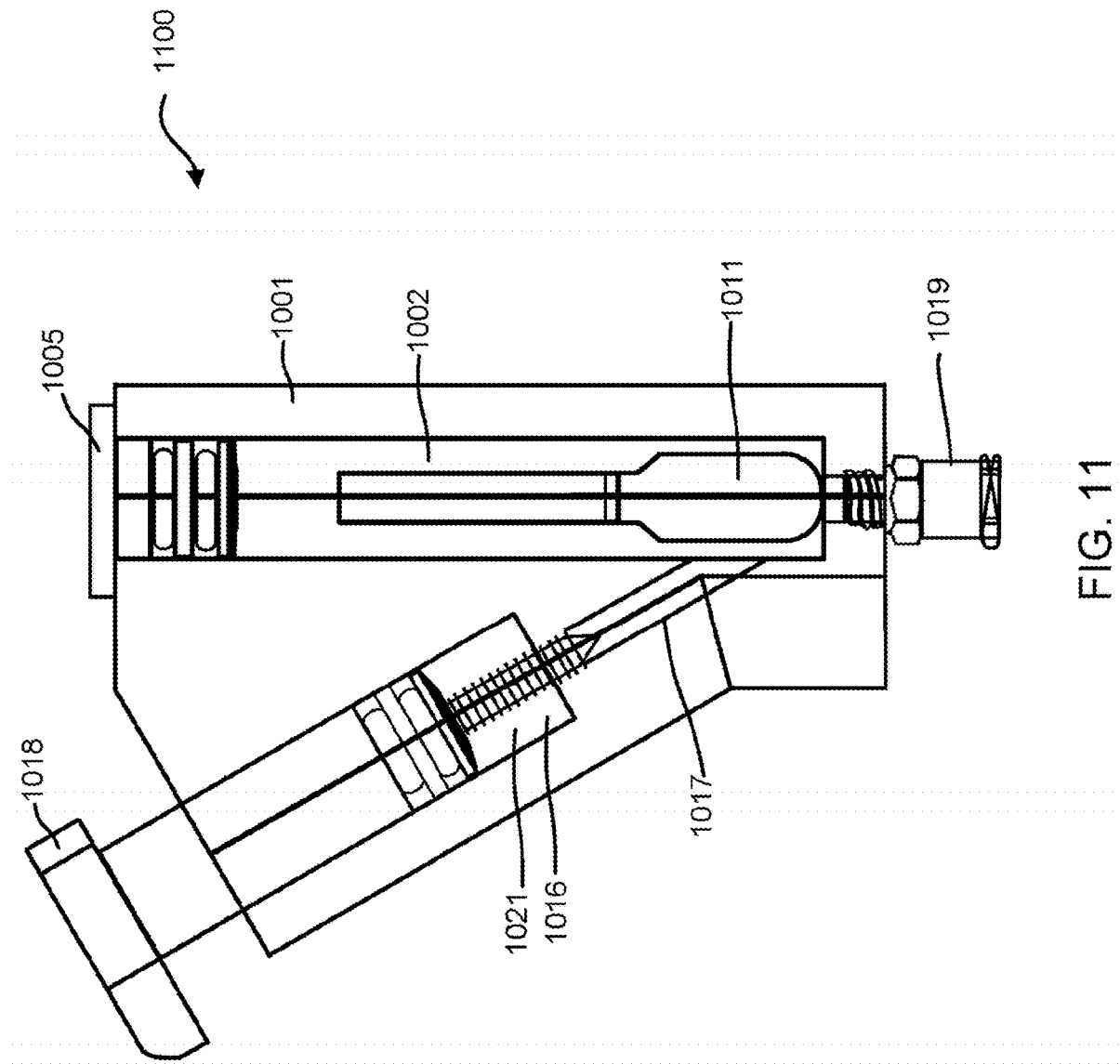
FIG. 11 provides a partial cross sectional view of a device according to some embodiments of the subject disclosure.

An embodiment of a biological assay sample preparation device for use in practicing the subject methods is provided in FIG. 11. The provided device 1100 includes many of the same components as the device shown in FIG. 10. However, the pressurizing chamber 1016 of the device 1100 of FIG.

11, can be oriented at an angle to the sample receiving module 1001, e.g., can both have a central axis of symmetry which intersects the other and/or is oriented at an angle, e.g., 30° or less, 45° or less, or 50° or less, or an angle ranging from 10° to 90°, inclusive, with respect to that of the other.

Figure 12:
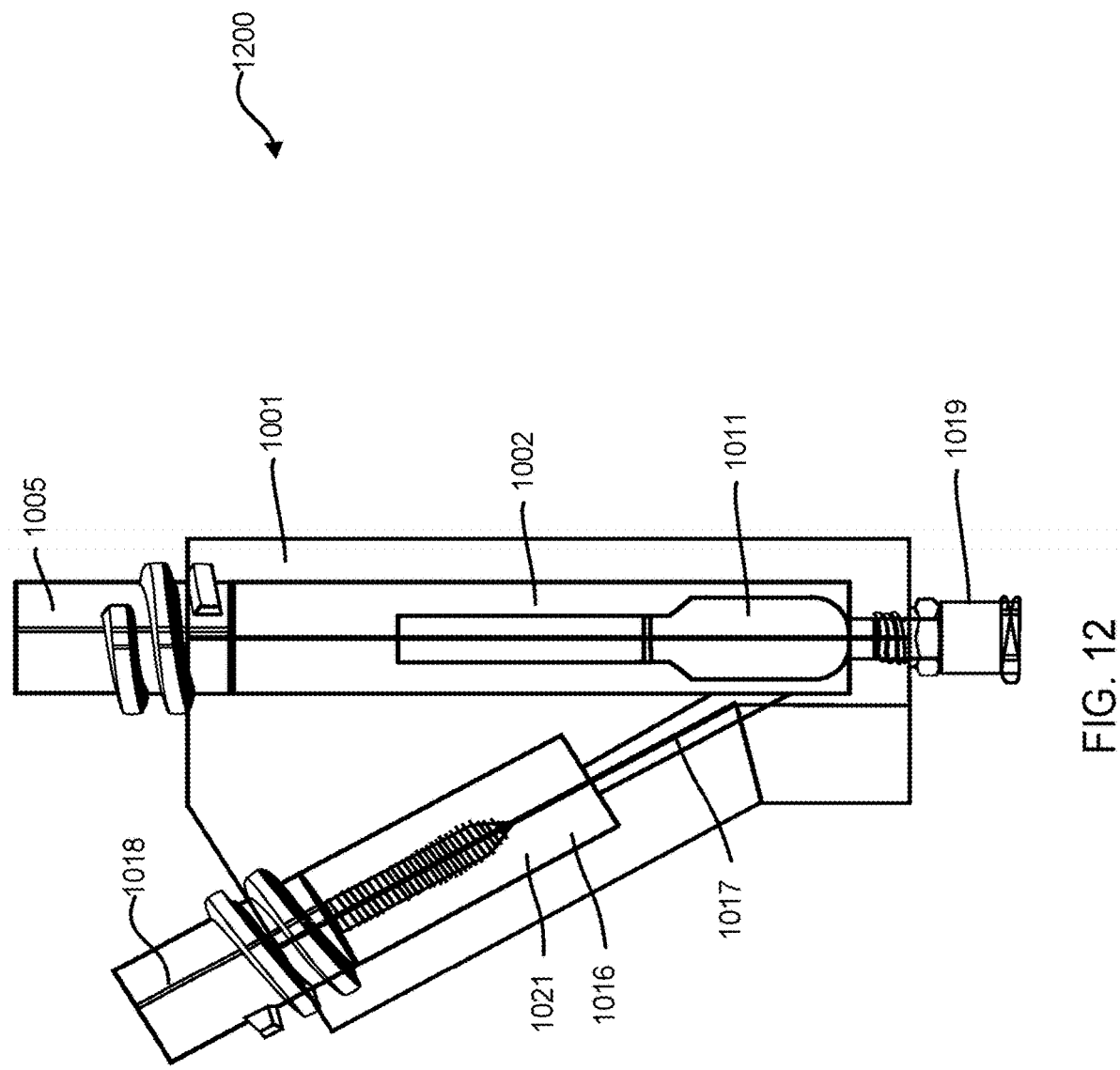
FIG. 12 provides a partial cross sectional view of a device according to embodiments of the present disclosure.

Another version of a biological assay sample preparation device for use in practicing the subject methods is provided in FIG. 12. The provided device 1200 includes many of the same components as the devices shown in FIGS. 10 and 11. The pressurizing chamber 1016 can be oriented at an angle to the sample receiving module 1001, e.g., can both have a central axis of symmetry which intersects the other and/or is oriented at an angle, e.g., 30° or less, 45° or less, or 50° or less, or an angle ranging from 10° to 90°, inclusive, with respect to that of the other. Furthermore, the cap 1005 of the device 1200 is operatively coupleable to the sample receiving module 1001 by screwable attachment. Also, the plunger 1018 of the device 1200 is actuable by screwing it, such as by twisting it, further into the pressurizing chamber 1016 to pressurize the pressurizing chamber 1016 and/or the sample receiving module 1001.

Figure 13:
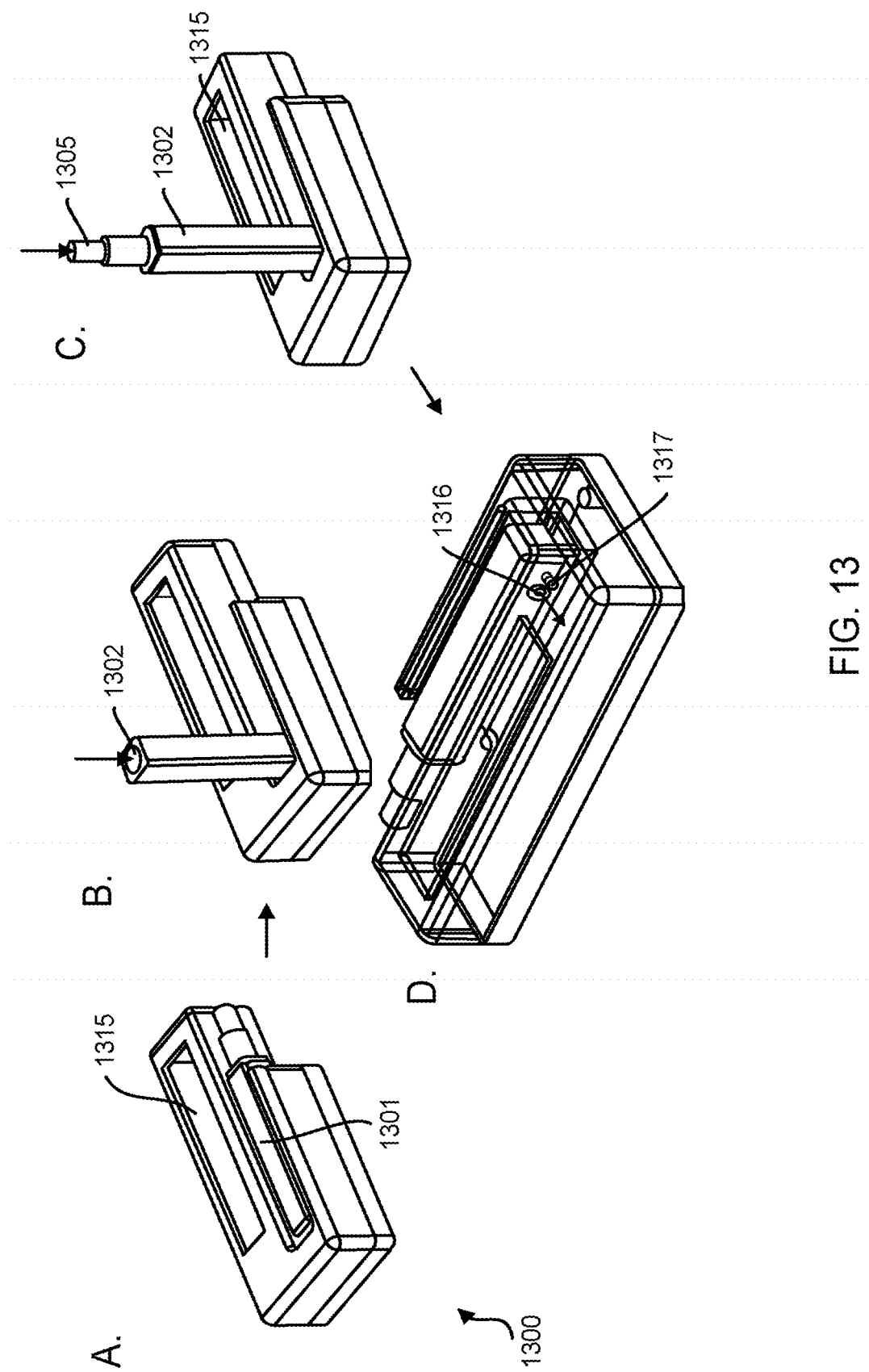
FIG. 13 provide perspective and partial cross sectional views of devices according to embodiments of the disclosure.

One aspect of a biological assay sample preparation device for use in practicing the subject methods is provided in A-D of FIG. 13. A of FIG. 13 shows the device in a stored configuration and B of FIG. 13 shows the device in a configuration such that a sample collector can be inserted therein. The device 1300 includes a sample receiving module 1301 including a fluid container 1302 for receiving one or more portions of a sample collector therein, e.g., entirely therein. Such a device 1300 can also include a cap 1305 operatively, e.g., removably, coupleable to the sample receiving module 1301 to pressurize the sample receiving module 1301, as is shown in C of FIG. 13. The sample receiving module 1301, cap 1305 and other provided components can have any of the characteristics or combination of characteristics of sample receiving modules, caps and/or other corresponding components described herein.

In the version shown, operatively coupling the sample receiving module 1301 and the cap 1305, as is shown in C of FIG. 13, can expose a preparation solution to a sample on a sample collector and thereby produces a prepared, e.g., lysed, sample. Once the prepared, e.g., lysed, sample is made, the sample receiving module 1301 can be operatively coupled, fluidically coupled, such as by actuating, such as by rotating the sample receiving module 1301 about an axis of a coupling component 1317, via a vent 1316, to a preparation module 1315 of the device 1300. Operatively coupling can be performed by rotating the sample receiving module 1301 about an axis of a coupling component 1317 90° or less.

The preparation module 1315 also can include a buffer, e.g., a dilution buffer. Operatively coupling the sample receiving module 1301 and the preparation module 1315, as is shown in D of FIG. 13, places the prepared sample in fluidic communication with the dilution buffer so that the prepared sample is diluted in the preparation module 1315. Thereafter, the diluted prepared sample can be delivered out of the device 1300 for further analysis using the pressure within the device to push the diluted prepared sample out of the device 1300.

Figure 14:
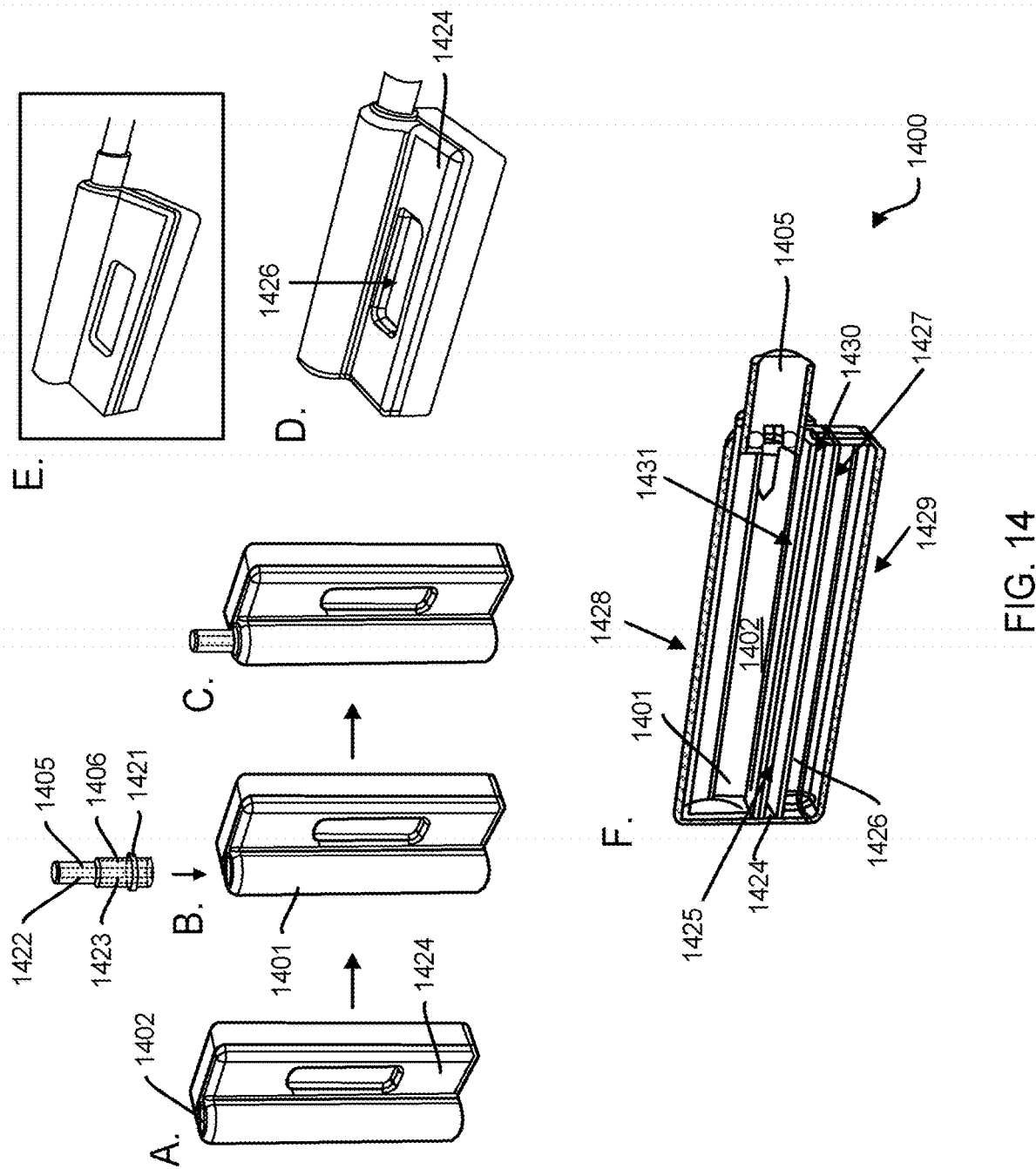
FIG. 14 provide perspective views of devices according to various embodiments of the subject disclosure.

A version of a biological assay sample preparation device for use in practicing the subject methods is provided in A-F of FIG. 14. A of FIG. 14 shows the device in a configuration such that a sample collector can be inserted therein, as indicated by the arrow. The device 1400 includes a sample receiving module 1401 including a fluid container 1402 for receiving one or more portions of a sample collector therein, e.g., entirely therein. Such a device 1400 can also include a cap 1405 operatively, e.g., removably, coupleable to the sample receiving module 1401, as is shown in C of FIG. 14. Such a cap 1405 can also include a preparation solution, e.g., a lysis buffer 1406, a seal 1421, and a plunger 1422 including a piercing member 1423. The plunger 1422 can be actuated by pushing the plunger 1422 to pierce the seal 1421 with the piercing member 1423, provide fluidic communication between the lysis buffer 1406 and a sample collector in the sample receiving module 1401, and pressurize the sample receiving module 1401. The sample receiving module 1401, cap 1405 and other provided components can have any of the characteristics or combination of characteristics of sample receiving modules, caps and/or other corresponding components described herein.

Once the prepared, e.g., lysed, sample is made, the prepared sample can pass to a sample incubation chamber 1424 via an actuating valve 1425 which can include a bimetal valve actuator. Therein, the sample can be incubated and the incubated sample measured to produce an assay result. The assay result can be displayed to a user via a display 1426 of the device 1400. The device 1400 also includes a power source 1426, e.g., one or more batteries, and a substrate 1427, e.g., a printed circuit board, for performing the measurement and displaying the result. The device 1400 also includes a housing composed of a top cover 1428 and a bottom cover 1429 and a bottom plate 1430 and/or gasket 1431 separating the sample receiving module 1401 and the incubation chamber 1424. Furthermore, F of FIG. 14 provides a cross-sectional view of the device 1400.

Optical Property Modifying Devices

The systems provided herein include various embodiments of biological sample assay optical property modifying devices. In some versions, such devices are selectively vented devices. By "selectively vented" is meant having one or more selective venting elements as disclosed herein and operating according to the associated methods.

In some versions, the subject devices include one or more, e.g., 2 or more, 5 or more, or 15 or more, selective venting elements. Selective venting elements can be porous and as such, have a plurality of pores extending therethrough. Such elements can have a passively tunable porosity and/or can control flow of one or more fluids, e.g., gas, such as air and/or liquids, such as liquids including a biological sample, within a device.

The phrase "passively tunable porosity," as used herein, refers to the ability of having a first conformation in which one or more gasses, e.g., air, can pass therethrough, e.g., through pores, and a second conformation in which fluids including the one or more gasses and liquids, such as liquids including a biological sample, are prevented from passing therethrough, e.g., through the pores, and proceeding automatically from the first to the second conformation upon contact with a liquid. Also, in the second conformation, the selective venting elements prevent evaporation of the liquids therethrough, e.g., through the pores. Furthermore, in the second conformation, the selective venting elements can fluidically seal a fluidic passage, e.g., a reaction chamber at an end by covering an opening of the reaction chamber, e.g., a venting opening, and prevent passage of fluid, including evaporation, therethrough. In addition, selective venting elements are configured to proceed from the first conformation to the second conformation passively, e.g., automatically without user interaction, upon contacting one or more liquids, such as liquids including a biological sample, with the selective venting elements or a portion thereof, e.g., a surface, such as a surface forming a wall of a reaction chamber. As such, in some versions, selective venting elements can be self-sealing to liquids and gasses when contacted by a liquid. Also, in some versions, selective venting elements may cover and/or seal one or more inlet and/or sample receiving opening of a device and may thereby regulate, e.g., allow and/or prevent liquid and/or gas flow therethrough in the same manner as through the one or more venting openings.

Also, each reaction chamber can include a sample receiving opening for receiving a biological sample from the sample inlet and/or a conduit. A sample receiving opening can be operatively, e.g., fluidically, connected to a sample inlet. In some versions, each reaction chamber includes one or more, e.g., two, additional openings, such as a "vented" and "supplementary," or "first" and "second" opening. Accordingly, in some versions, a sample receiving opening is a third opening and is adjacent to the first and/or second openings. Reaction chambers can also include a fourth opening operatively coupling the chamber to one or more other chambers and/or the inlet via one or more conduits.

In various instances, passing a liquid through one or more surface of a selective venting element causes the selective venting element to proceed from a first confirmation to a second confirmation. Accordingly in some versions, selective venting elements are configured to receive an amount, e.g., a small amount, of a liquid, e.g., biological sample, water and/or buffer, therein when contacted by the liquid. The presence of the liquid within the element seals pores of the element and/or expands the element so that further liquid and/or gas cannot pass into or through the element.

Selective venting elements can include a body and one or more protrusions extending therefrom. Each protrusion can extend from the body to a surface, e.g., a sealing surface, at an end of the protrusion. The sealing surface can extend into and/or over, e.g., completely over, an opening at an end of a reaction chamber. In some versions, a portion of a sealing surface, e.g., a concentric portion, can contact a surface, e.g., a top or bottom surface, of a sample receiving cartridge when the cartridge is operatively coupled to the selective venting element. In some versions, a selective venting element does not extend into a reaction chamber when the device operates. As such, according to the subject embodiments, an amount of liquid, e.g., biological sample, water, and/or buffer, can be passed into a selective venting element through a sealing surface of a protrusion to thereby seal the selective venting element and prevent further passage of liquid or gas, such as by evaporation, into or through the element.

Figure 17:
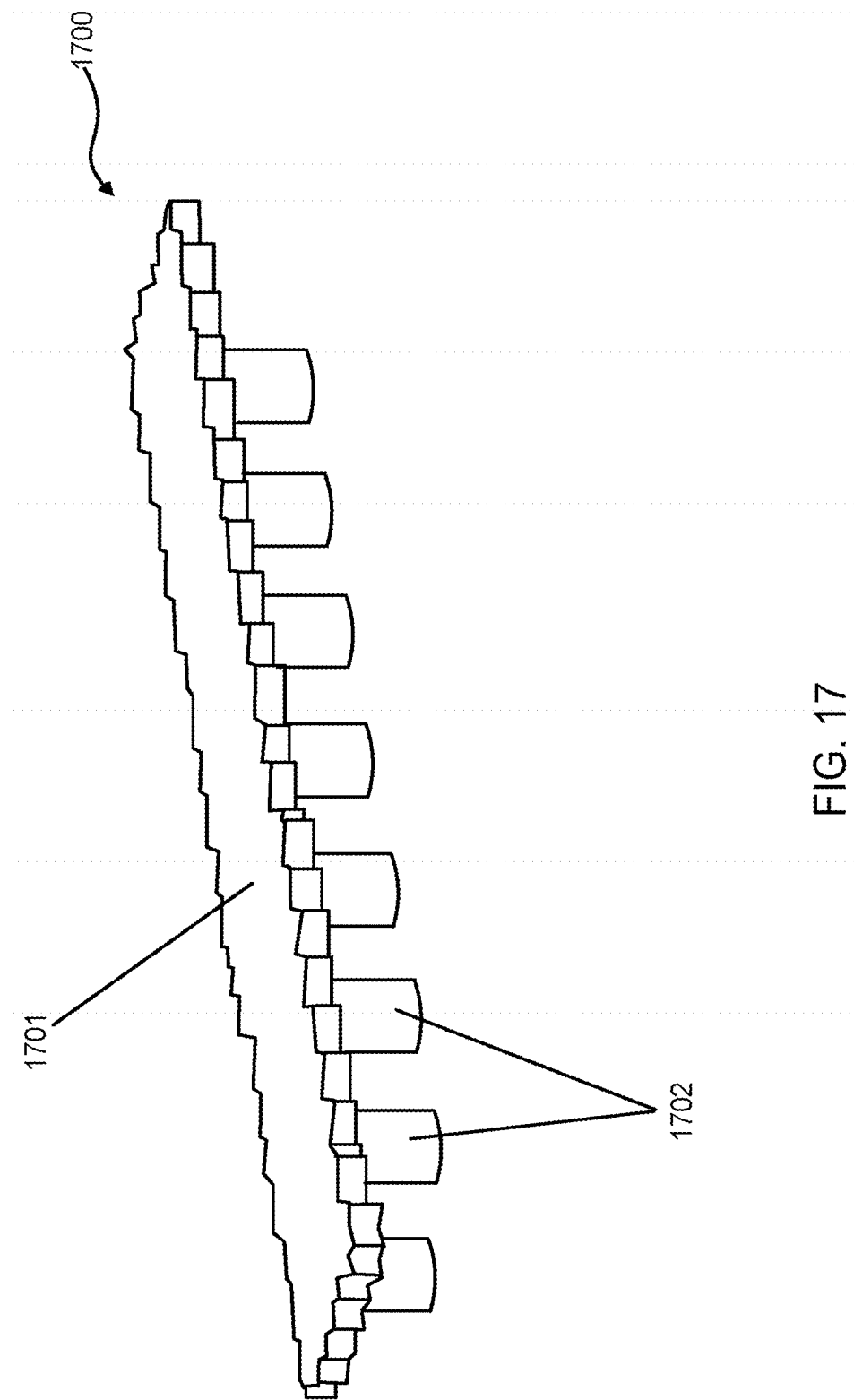
FIG. 17 provides a perspective view of a device component according to embodiments of the subject disclosure.

One embodiment of a selective venting element 1700 for use in practicing the subject methods is provided in FIG. 17. As is shown, in various embodiments, the element 1700 is shaped as a comb and includes a body 1701 and one or more protrusions 1702, e.g., sealing protrusions, extending from the body 1701.

A body of a selective venting element, or a "body," according to the subject embodiments, can be or include a sheet, e.g., a solid sheet, of one or more materials, e.g., two materials, having a thin and/or planar shape. A body or other components of the subject devices can include a top surface and a bottom surface each defining a plane parallel with the other and separated by a thickness. In some versions, protrusions extend from the top and/or bottom surface. In various embodiments, a selective venting element body is or includes a uniform layer of a single material. A body can also be composed of two or more, e.g., three, four, five, or more, etc. sheets laminated to one another.

A body of a selective venting element can, in some aspects, have a length, a width and a height, also referred to as a thickness. A selective venting element body can be shaped as a rectangular box with the width and length being substantially greater than the thickness. A thickness of a body, e.g., a thickness between a first surface and a second surface opposite the first surface, can be 5 mm or less, 3 mm or less, 1 mm or less, 0.5 mm or less, 0.1 mm or less, or 50 microns or less. A thickness of a selective venting element body can also range for example, from 2 cm to 50 microns, from 1 cm to 50 microns, such as 5 mm to 50 microns, or from 5 mm to 0.1 mm, such as 2 mm to 0.1 mm, inclusive. Also, a length and/or width of a body can also range from 1 mm to 40 cm, such as from 1 cm to 30 m, such as from 1 cm to 10 cm, such as from 1 cm to 5 cm, or from 1 mm to 5 cm, from 1 mm to 3 cm, from 1 mm to 1 cm or from 1 mm to 5 mm.

Aspects of selective venting element bodies can be and/or have an area defining any suitable size or shape including a: circle, semi-circle, oval, rectangle, square, triangle, polygon, quadrilateral, or combination thereof. For example, in embodiments where the body is shaped a rectangle, the length of the body is greater than the width. A body can include one or more sheets of solid, uniform, integrated material, and in some versions, may not include any openings therethrough.

A selective venting element body can have three edges, four edges, or more than four edges which define the area of the body. In various embodiments, the edges meet at corners, e.g., three, four, five, or ten or more corners. In some versions, a first edge of an adhesive layer is opposite a second edge of an adhesive layer and adjacent to a third and/or fourth edge of an adhesive layer. In such an embodiment, the third edge can be opposite a fourth edge and the fourth edge can be adjacent to the first and/or second edge. Also, in some versions, a selective venting element includes only a body and does not include protrusions extending therefrom.

Furthermore, as noted above, in various instances, a selective venting element includes one or more protrusions, e.g., sealing protrusions, extending from the body or a portion thereof, e.g., a top and/or bottom surface. In various embodiments, a selective venting element includes one or more, such as a plurality, such as two or more, such as 5 or more, such as 10 or more, such as 15 or more, such as 20 or more, such as 50 or more protrusions. A selective venting element can include 50 or less, such as 20 or less, such as 15 or less, such as 10 or less, such as 5 or less protrusions. A selective venting element can include from 1 to 25, such as from 1 to 20, such as from 1 to 15, such as from 1 to 10 such as from 1 to 5, protrusions, or from 2 to 20, such as from 2 to 15, such as from 5 to 15 protrusions, wherein each range is inclusive. A selective venting element can include 1, 2, 3, 4, 5, 6, 7, 8, 9, 10, 11, 12, 13, 14, 15, 16, 17, 18, 19, or 20 or more protrusions. A selective venting element of a device can have a number of protrusions equal to the number of reaction chambers in the device.

A protrusion of a selective venting element can be shaped as a cylinder, rectangular box, pyramid, cube, or any combination thereof. In embodiments where protrusions are shaped as a cylinder, they can have a height, e.g., a distance from a surface of a venting element body to a sealing surface at an end of the protrusion, ranging from 0.1 mm to 5 cm, such as 0.1 mm to 1 cm, such as 0.1 mm to 5 mm, such as 0.1 mm to 1 mm, or 1 mm to 5 mm, inclusive. A protrusion can also have a height of 5 cm or less, such as 3 cm or less, such as 1 cm or less, such as 5 mm or less, such as 3 mm or less, such as 1 mm or less. A protrusion can also have a height of 0.1 mm or more, such as 1 mm or more, such as 3 mm or more, such as 5 mm or more, such as 1 cm or more, such as 3 cm or more, such as 5 cm or more. Such a protrusion can also have a diameter ranging from 0.1 mm to 5 cm, such as 0.1 mm to 3 cm, such as 0.1 mm to 1 cm, such as 0.1 mm to 5 mm, such as 0.1 mm to 1 mm, or 1 mm to 1 cm, or 1 cm to 3 cm, each inclusive. Protrusions can also have a diameter of 5 cm or less, such as 3 cm or less, such as 1 cm or less, such as 5 mm or less, such as 3 mm or less, such as 1 mm or less, such as 0.5 mm or less. A protrusion can also have a diameter of 0.1 mm or more, such as 1 mm or more, such as 3 mm or more, such as 5 mm or more, such as 1 cm or more.

In aspects where a protrusion is shaped as a rectangular box or a cube, the pressurizing component can have a length, width, and/or height of 1 cm or less, such as 0.5 cm or less, such as 0.3 cm or less, such as 1 mm or less, such as 0.5 mm or less, such as 0.3 mm or less, such as 0.1 mm or less. A protrusion can also have a length, width, and/or height of 1 mm or more, such as 3 mm or more, such as 5 mm or more, such as 1 cm or more, such as 3 cm or more, such as 5 cm or more. A pressurizing component can also have a length, width, and/or height ranging from 0.1 mm to 5 cm, such as 0.1 mm to 3 cm, such as 1 mm to 1 cm, or 1 cm to 3 cm, each inclusive.

In some instances, each protrusion is separated from another protrusion on a body by a distance, e.g., a distance on a surface of a body, ranging from 0.1 mm to 5 cm, such as 0.1 mm to 1 cm, such as 0.1 mm to 5 mm, such as 0.1 mm to 1 mm, or 1 mm to 5 mm, inclusive. Such a distance can also be 5 cm or less, such as 3 cm or less, such as 1 cm or less, such as 5 mm or less, such as 3 mm or less, such as 1 mm or less. A distance between protrusions can also be 0.1 mm or more, such as 1 mm or more, such as 3 mm or more, such as 5 mm or more, such as 1 cm or more, such as 3 cm or more, such as 5 cm or more.

Where desired, a protrusion or a portion thereof, e.g., a sealing surface, at an end of a protrusion can be a flat planar surface defining, for example, a circular shape and can extend into and/or over an opening at an end of a reaction chamber. By extending into and/or over, e.g., completely over, such an opening, the surface can seal the reaction chamber.

In some embodiments, selective venting elements or portions thereof, e.g., one or more bodies and/or protrusions, are be composed of a single body of solid, uniform, integrated material. In other versions, a body of a selective venting element can be composed of a different material than one or more protrusions thereof.

Also, one or more portions or materials of selective venting elements can have a passively tunable porosity. For example, in some versions, selective venting elements can be composed of a hydrogel having a passively tunable porosity. Such a hydrogel can be capable of swelling and reducing the porosity of the porous polymer matrix upon contact with a liquid, e.g., an aqueous liquid.

Furthermore selective venting elements can be composed of a variety of materials including one or more polymer matrix, such as a porous polymer matrix, such as polyethylene. Selective venting elements can also be composed of a hydrogel such as carboxymethyl cellulose. Other materials of which selective venting elements or portions thereof, such as coatings, can also be composed include saccharides, proteins, deliquescent materials, nylon, ABS, polycarbonate, and Poly(methyl methacrylate), and other hygroscopinc materials, or any combinations thereof. Selective venting elements can also be or include one or more coatings.

Figure 18:
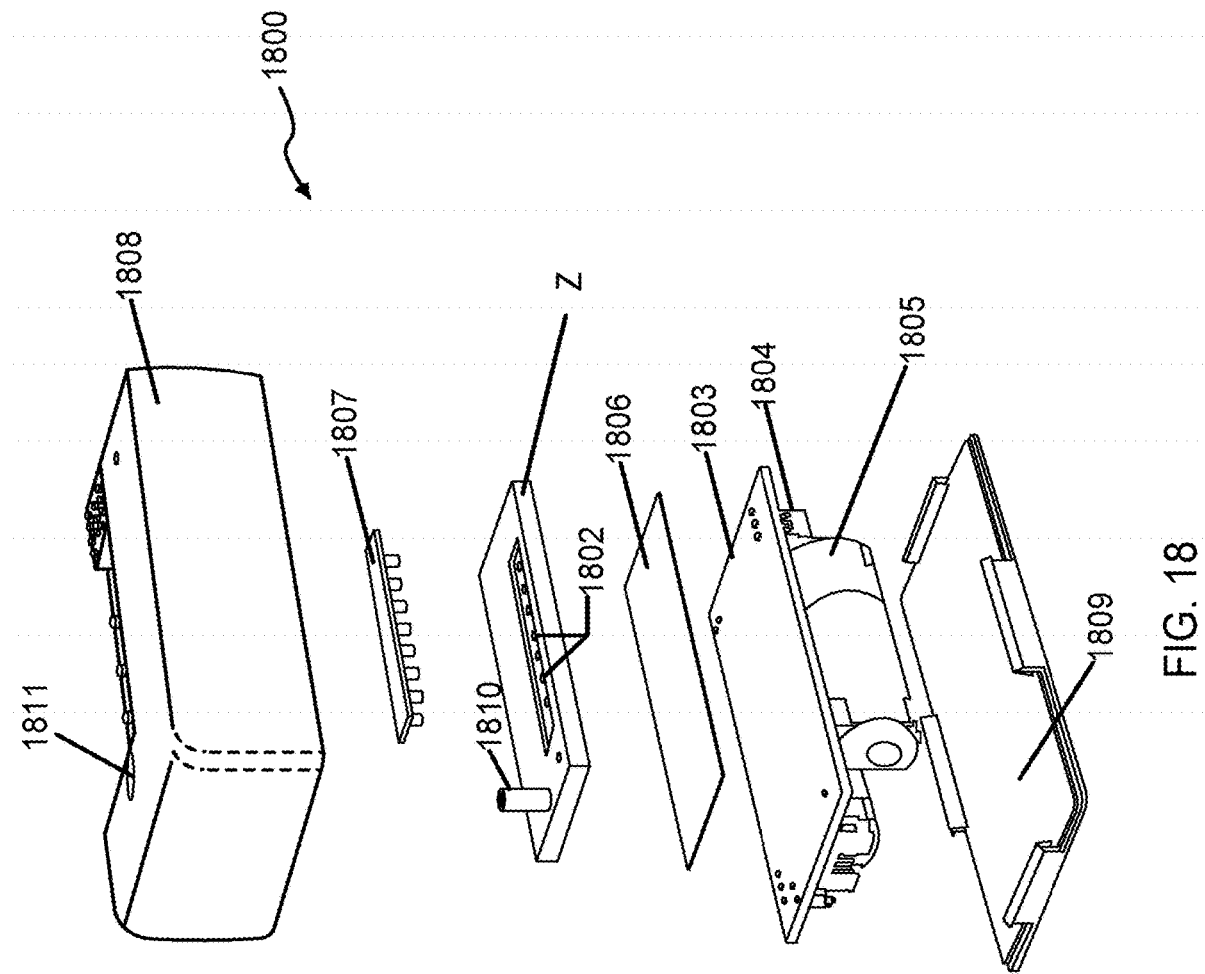
FIG. 18 provides a perspective view of a device according to versions of the subject disclosure.

One embodiment of an optical property modifying device for use in practicing the subject methods is provided in FIG. 18. In various embodiments, the device 1800 includes a selective venting element 1807. Also provided is a sample receiving cartridge 1801 including one or more reaction chambers 1802 for receiving a biological sample and each including an optical property modifying reagent. Such a device 1800 also includes a substrate 1803 including a heating element 1804 and/or a power source 1805 operatively coupled to the heating element 1804. Also, as used herein, the phrase "optical property," refers to one or more optically-recognizable characteristics, such as a characteristic resulting from wavelength and/or frequency of radiation, e.g., light, emitted from an aspect, such as color, fluorescence, phosphorescence, etc. As such, modifying an optical property refers to changing such a characteristic.

The illustrated device 1800 also includes an adhesive layer 1806. Such a layer 1806 can operatively connect the sample receiving cartridge 1801 and the substrate 1803 and thereby form a wall of each of the one or more reaction chambers 1802. The device 1800 also includes a selective venting element 1807 which also forms a wall of each of the one or more reaction chambers 1802. Also, as provided in FIG. 18, the device includes a housing composed of a first portion 1808 including a receptacle 1811 and a second portion 1809 mateable with the first portion to encapsulate the sample receiving cartridge 1801, substrate 1803 and adhesive layer 1806. In such a configuration, the sample receiving cartridge 1801, substrate 1803 and adhesive layer 1806 can all be disposed between at least two opposite portions, e.g., walls, of the first portion 1808.

Figure 19:
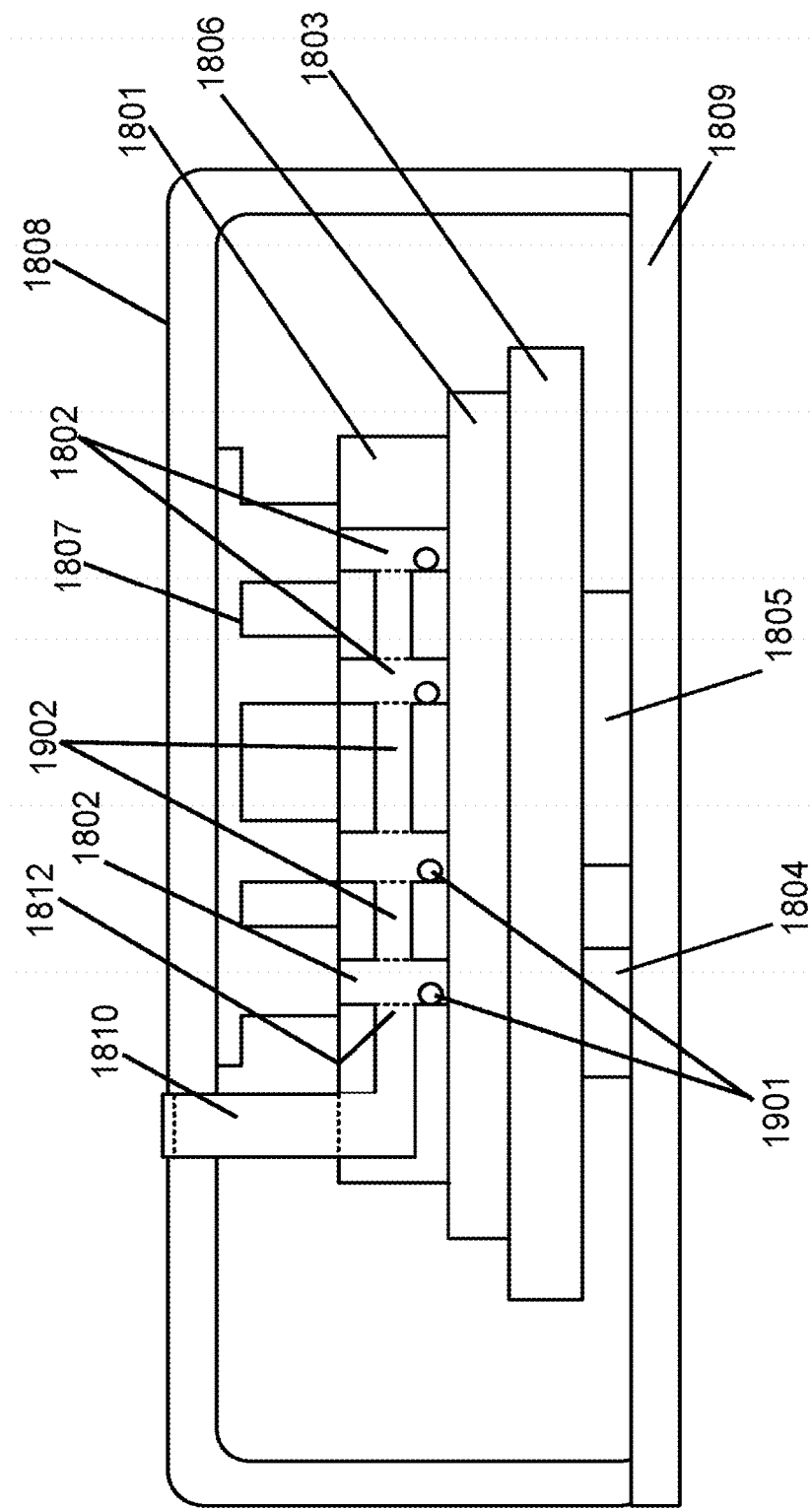
FIG. 19 provides a representative cross sectional view of a device according to embodiments of the present disclosure.

As the embodiment provided in FIG. 18, is shown in an unassembled conformation for illustrative purposes, a representative embodiment of the device in an assembled conformation is provided in FIG. 19. FIG. 19 specifically provides a representative illustration of many of the same elements as FIG. 18. FIG. 19 also shows a modifying reagent 1901 within each of the one or more reaction chambers 1802. Also shown are conduits 1902 operatively coupling each of the one or more reaction chambers 1902 with one another and/or with a sample inlet 1910.

A sample receiving cartridge according to the subject disclosure can include one or more, such as a plurality, such as two or more, such as 5 or more, such as 10 or more, such as 15 or more, such as 20 or more, such as 50 or more reaction chambers. A sample receiving cartridge can include 50 or less, such as 20 or less, such as 15 or less, such as 10 or less, such as 5 or less reaction chambers. A sample receiving cartridge can include from 1 to 25, such as from 1 to 20, such as from 1 to 15, such as from 1 to 10 such as from 1 to 5, reaction chambers, or from 2 to 20, such as from 2 to 15, such as from 5 to 15 reaction chambers, wherein each range is inclusive. A sample receiving cartridge can include 1, 2, 3, 4, 5, 6, 7, 8, 9, 10, 11, 12, 13, 14, 15, 16, 17, 18, 19, or 20 or more reaction chambers.

Where appropriate, each reaction chamber can be shaped as a cylinder, rectangular box, cube, or any combination thereof. Each reaction chamber can include a sample receiving opening for receiving a biological sample from the sample inlet and/or a conduit. A sample receiving opening can be operatively, e.g., fluidically, connected to a sample inlet. In some versions, each reaction chamber includes one or more, e.g., two, additional openings, such as a "vented" and "supplementary," or "first" and "second" opening. Accordingly, in some versions, a sample receiving opening is a third opening and is adjacent to the first and/or second openings. Reaction chambers can also include a fourth opening operatively coupling the chamber to one or more other chambers and/or the inlet via one or more conduits.

In some instances, each reaction chamber can extend from a first opening in a first surface of a sample receiving cartridge, through the cartridge to a second opening in a second surface of a sample receiving cartridge opposite the first. Also, as noted herein, each opening can be a sealed by a portion, e.g., surface, of a component, such as an adhesive layer and/or a selective venting element, each forming a wall of a reaction chamber. For example an adhesive layer can form a wall of a reaction chamber at a first end and/or a selective venting element can form a wall of the reaction chamber at a second end opposite the first. In doing so, the adhesive layer can seal each supplementary or "second" opening and/or the selective venting element can seal each venting or "first" opening.

Each reaction chamber can also be a microfluidic reaction chamber. The subject reaction chambers can each have a volume of 1 µL to 1000 µL, such as 1 µL to 100 µL, such as 1 µL to 50 µL, such as 10 µL to 30 µL, such as 15 µL to 30 µL, or 50 µL or less, or 30 µL or less. As such, each reaction chamber is configured to receive contents, e.g., contents including solid and/or liquid media, such as a biological sample and/or optical property modifying reagents, therein having a volume equal to or less than any of the provided volumes.

In various instances, each reaction chamber can include, such as contain within a chamber, one or more modifying reagent, such as an optical property modifying reagent. A modifying reagent is a reagent that chemically modifies a biological sample or an aspect thereof when mixed therewith. In some versions, a modification reagent includes an amplification reagent as described herein. In various embodiments, optical property modifying reagents can include one or more biomarker and/or biomarker target, pH sensitive dyes, fluorescent dyes, FRET dyes, micro and nano particles, fluorescent proteins, colorimetric substrates, enzymes and reagents, plasmonic structures, precipitation reagents and substrates, or any combination thereof.

In some versions, the optical property modifying reagent is or includes an enzyme-linked immunosorbent assay (ELISA) reagent. In some aspects, the ELISA reagent is selected from the group consisting of alkaline phosphatase, horseradish peroxidase, β-galactosidase, BCIP/NBT (5-bromo-4-chloro-3-indolyl-phosphate/nitrobluetetrazolium), TMB (3,3',5,5' tetramethylbenzidine), DAB (3,3',4,4' diaminobenzidine), 4CN (4-chloro-1-naphthol). TMB (dual function substrate), ABTS (2,2'-azino-di [3-ethylbenzthiazoline] sulfonate), OPD (o-phenylenediamine), MUG (4-methylumbelliferyl galactoside), HPA (hydroxyphenylacetic acid), and HPPA (3-p-hydroxyphenylproprionic acid).

Also, in some versions, an optical property modifying reagent, can be stored in a sample receiving cartridge in dry, e.g., lyophilized, form. As such, moving a biological sample, e.g., a fluid biological sample, into a reaction chamber can include mixing the biological sample and the optical property modifying reagent and/or hydrating the optical property modifying reagent. According to some embodiments, an optical property of an optical property modifying reagent is changed due to the presence or the absence of a particular marker in a biological sample when the biological sample or one or more aspect thereof, such as one or more amplified nucleic acids and/or protons, are exposed to the optical property modifying reagent.

In some instances, each reaction chamber can include, such as contain within a chamber, one or more nucleic acid amplification composition. Such nucleic acid amplification composition can include, for example, one or more primers, deoxynucleotides (dNTPs), and/or polymerases, Trizma preset crystals (Tris buffer, pH 8.8; Sigma, cat. no. T9443), Potassium chloride (KCl; Wako Pure Chemicals, cat. no. 163-03545), Magnesium sulfate heptahydrate (MgSO4; Wako Pure Chemicals, cat. no. 137-00402), Ammonium sulfate ((NH4)2SO4; Kanto Chemical, cat. no. 01322-00), TWEEN® 20 (Tokyo Chemical Industry, cat. no. T0543), Betaine solution (Betaine, 5 M; Sigma, cat. no. B0300), Calcein (DOJINDO, cat. no. 340-00433) plus all other optical modification reagents as discussed above, Manganese(II) chloride tetrahydrate (MnCl2; Wako Pure Chemicals, cat. no. 133-00725), Agarose S, EtBr solution, template nucleic acids, or any combination thereof. In addition, in some versions, a nucleic acid amplification composition, can be stored in a sample receiving cartridge in dry, e.g., lyophilized, form. As such, moving a biological sample, e.g., a fluid biological sample, into a reaction chamber can include mixing the biological sample and the nucleic acid amplification composition and/or hydrating the nucleic acid amplification composition.

According to some versions of the subject disclosure, the nucleic acid amplification composition includes one or more buffer and/or water. A nucleic acid amplification composition is a solution which prepares a biological sample such that one or more nucleic acid thereof can be amplified, e.g., amplified isothermally.

Where appropriate, a nucleic acid amplification composition can be a reagent which prepares a biological sample for amplification with an isothermal amplification protocol including: transcription mediated amplification, strand displacement amplification, nucleic acid sequence-based amplification, rolling circle amplification, loop-mediated isothermal amplification, isothermal multiple displacement amplification, helicase-dependent amplification, circular helicase-dependent amplification, single primer isothermal amplification, loop-mediated amplification, or any combination thereof.

In various aspects, the amplification according to the subject embodiments is reverse transcriptase loop-mediated amplification (RT-LAMP). In various aspects, RT-LAMP is an isothermal gene amplification procedure in which the reaction can be processed at a constant temperature, e.g., 63° C., by one type of enzyme, e.g., Bst polymerase, in a single step. RT-LAMP, in various aspects, uses six primers that recognize eight regions on a target nucleic acid. In various embodiments, the sensitivities and specificities of the RT-LAMP technique is higher than those associated with performing a polymerase chain reaction (PCR). The RT-LAMP method is also fast, producing a signal from a few copies of RNA in 60 minutes, or less, 45 minutes or less, 30 minutes or less, or 15 minutes or less. RT-LAMP can also not require any special reagents. Also, according to the subject embodiments a detection according to the subject embodiments is a detection of one or more aspects, such as specific pathogenic genetic markers in samples. Amplification according to the subject embodiments can also be performed by applying PCR.

In some embodiments, the sample receiving cartridges also include one or more conduits operatively, e.g., fluidically, connecting each or any combination of the one or more reaction chambers with one another and/or with a sample inlet. Each of the one or more conduits can be shaped as a cylinder or a quadrilateral prism and can have dimensions including a length of 10 m or less, such as 1 m or less, such as 10 cm or less, such as 1 mm or less, and/or have a diameter, width and/or height of 100 mm or less, such as 10 mm or less, such as 1 mm or less, such as 0.1 mm or less, such as 10 micrometers or less. Each of the one or more conduits can also have a volume of 1000 μL or less, such as 10 μL or less, such as 1 μL or less, such as 0.1 μL or less, such as 1 nL or less. Movement, e.g., diffusion, of a liquid or a component thereof from one reaction chamber to another is substantially prevented by the conduits due to the length of the conduits. Accordingly, each of the reaction chambers is isolated from one another and the amount of such movement over the duration of an assay is negligible in influencing an assay result.

In some aspects the sample receiving cartridges also include one or more inlets, e.g., sample inlets, operatively, e.g., fluidically, connecting each or any combination of the one or more reaction chambers with one another and/or with an environment external to the device. Each of the one or more inlets can be shaped as a tube extending from a surface of the microfluidic cartridge through the cartridge. A first end of the inlet can extend from a surface of the cartridge to an opening in the housing and be configured for receiving a fluid, e.g., a biological sample, therein. A second end, or a plurality of second ends, opposite the first end of the inlet, can each terminate at a reaction chamber, e.g., a sample receiving opening of a reaction chamber, and be configured for conveying fluid, e.g., biological sample, to the chamber. Also, a second end, or a plurality of second ends, opposite the first end of the inlet, can each terminate at a conduit, as described herein. An inlet can also be microfluidic and can be configured such that a fluid flows automatically therethrough upon introduction at a first end. An inlet can have a diameter ranging from 1 μm to 10 cm and can also have a volume of 1 pL to 1 mL. Furthermore, in some versions, inlets can include one or more connectors, e.g., fluidic connectors, e.g., luer connectors, such as at an end, for operatively connecting to one or more reciprocating connectors, e.g., fluidic connectors, e.g., luer connectors, such as one or more connector of a sample preparation device.

The sample receiving cartridges can be composed of one or more materials including, for example, polymeric materials (e.g., materials having one or more polymers including, for example, plastic and/or rubber) and/or metallic materials. Materials of which any of the device components including sample receiving cartridges or portions thereof described herein can be composed include, but are not limited to: polymeric materials, e.g., plastics and/or elastomers, such as polytetrafluoroethene or polytetrafluoroethylene (PFTE), including expanded polytetrafluoroethylene (e-PFTE), polyethylene, polyester (Dacron™), nylon, polypropylene, polyethylene, high-density polyethylene (HDPE), polyurethane, polydimethylsiloxane (PDMS), etc., metals and metal alloys, e.g., titanium, chromium, aluminum, stainless steel, etc., and the like. In various embodiments, the materials are transparent materials and as such, allow light within the visible spectrum to efficiently pass therethrough.

In various instances, a sample receiving cartridge, or a portion thereof is transparent to light, e.g., visible light. As such, a user can observe an optical property modification of a sample or an aspect thereof through the sample receiving cartridge. Also, in some versions, a sample receiving cartridge, or a portion thereof, is opaque and/or white.

The subject devices can include a substrate. A substrate can be operatively coupled to the sample receiving cartridge via, for example, an adhesive layer. The substrate, in some instances, can be a circuit board, e.g., a printed circuit board, composed, for example, of a layer of Silicon and/or Copper and/or Gold and/or Aluminum contacts therein or thereon. Substrates can be printed circuit boards composed, for example, of a layer, e.g., a silicon layer, having thereon metallic contacts affixed thereto with one or more adhesive, e.g., epoxy. Substrates according to the subject embodiments can also have one or more surface, e.g., a first surface and a second surface opposite a first surface, having a roughness (Ra) of 5 μm or more, such as 10 μm or more, such as 20 μm or more, such as 50 μm or more. The substrates can also have a roughness (Ra) of 50 μm or less, such as 20 μm or less, such as 10 μm or less, such as 5 μm or less.

Substrates, in various instances, can include one or more optical property modifying substances and as such, be configured to have one of their optical properties, such as color, modified. As such, the methods include modifying one or more optical property of a substrate. In some aspects, substrates can include one or more enzyme, e.g., a colorimetric enzyme, which can provide a color change. As such, modifying an optical property can include changing the color and/or opacity of a substrate.

In some embodiments of the subject devices, the substrates can include one or more heating elements. Heating elements are elements and/or one or more reactants that are configured to generate thermal energy and can be configured for heating one or more reaction chambers and contents thereof, e.g., a biological sample and/or an optical property modifying reagent and/or a nucleic acid amplification composition. Examples of such heating elements include thermoelectric heating elements, e.g., thermoelectric heating elements that include resistive conductors, e.g., thermistors, Peltier devices, or other elements that generate heat.

In some aspects, heating elements are or include one or more heat-generating reactants, e.g., liquid reactants, that cause an exothermic reaction when exposed to one another or one or more of the compositions and/or reagents disclosed herein, e.g., water. Also, in some embodiments, the methods include adding to contents of a device as disclosed herein, e.g., contents including a biological sample, one or more heating reagents which, when mixed, cause an exothermal reaction. Such a reaction can, for example, heat a sample for lysis or produce a colorimetric change as described herein.

The heating elements described herein can be configured to elevate the temperature of a reaction chamber and/or contents thereof, e.g., a biological sample, by 1° C. or more, 5° C. or more, 10° C. or more, 15° C. or more, 25° C. or more, 50° ° C. or more, or 100° C. or more. Such elements can be configured to increase the temperature of a reaction chamber and/or contents thereof from room temperature, e.g., 21° C., to 59° C., 60° C., 61° ° C., 62° C., 63° C., 64° C., 65° C., 66° C., or 67° C. and/or within a range from 50-75° C., such as 60-70° C., such as 60-66° C., in 10 minutes or less, such as in 5 minutes or less, such as in 3 minutes or less, such as in 2 minutes or less. For example, a heating element can be configured to increase the temperature of a reaction chamber and/or contents thereof from room temperature to 63° C.±1° C. in 3 minutes or less and/or can be configured to maintain such a temperature for 30 minutes or more. Heating elements can also be configured to maintain the temperature of a reaction chamber and/or contents thereof for a period of time such as 2 hours or more or 2 hours or less, such as 1 hour or less, such as 30 minutes or less, such as 15 minutes or less. Such a temperature can be maintained at, for example, 59° C., 60° C., 61° C., 62° ° C., 63° C., 64° C., 65° C., 66° C., or 67° C. and/or within a range from 50-75° C., such as 60-70° C., such as 60-66° C. Maintaining such a temperature can be performed by applying a thermistor as a heating sensing element and/or can be based on sensor feedback to a control unit. Heating elements can be configured to elevate the temperature of a reaction chamber and/or contents thereof, repeatedly, e.g., heat the contents a first time and then a second time. The subject heating elements also can heat the contents of a reaction chamber so that an optical property modification and/or nucleic acid amplification occurs. Furthermore, the subject heating elements also can heat contents to perform thermo-cycling for amplification reactions, such as PCR.

Where appropriate, the subject substrates include one or more power sources. A power source can be operatively connected to one or more heating elements. By "power source," as used herein, is meant a device that supplies electric power to an electrical load. As such, in some aspects, power sources can include, for example, one or more battery, direct current (DC) power supply, alternating current (AC) power supply, linear regulated power supply, switched-mode power supply, programmable power supply, uninterruptible power supply, high-voltage power supply and/or a voltage multiplier. The amount of power, current and/or voltage capable of being provided by a power supply can, for example, be equivalent to that required to power the heating elements to generate heat according to the subject embodiments and/or other elements described herein, e.g., one or more controller, to provide their described functions. A power source can, in some aspects, be one or more battery, e.g., a portable and/or self-contained and/or replaceable battery, such as one or two AA batteries, an outlet, or another source of electrical power. In some aspects, a power source can include one or more electrical cords, e.g., cords configured to operatively connect a device to an outlet. Cords of power sources can be configured to removably connect to a device and/or an outlet.

Aspects of power sources include power sources configured to turn on to provide electrical power to another component and/or turn off to stop providing electrical power to another component. Such power sources can be configured to be turned on and/or off, for example, by operation of a switch, button, timer or other component operatively connected to or included in the power source, such as a control unit.

Versions of power sources can also, in certain aspects, be operatively connected to one or more components of the disclosed systems, e.g., a control unit. As such, embodiments of power sources include electrical connections from a power source to components of the disclosed systems. Such electrical connections can include one or more lengths of electrically conductive material, e.g., contacts, traces, and/or wires.

Substrates can include one or more control unit, e.g., a central processing unit (CPU) or a field-programmable gate array (FPGA). Such a unit can include a memory and/or a processor, e.g., a microprocessor, configured to generate one or more outputs, e.g., electrical signals, based on one or more sets of inputs, e.g., inputs from a user and/or a sensor, and/or a timer, and/or instructions stored in the memory. A device can also include a user interface for receiving an input and operatively coupled to the control unit.

According to various embodiments, a control unit is configured to perform an optical property modification and/or colorimetric analysis of a biological sample in the one or more reaction chambers. As such, a control unit can be configured to determine, based on an input from one or more sensors, whether a change in an optical property, e.g., color, of one or more contents of a reaction chamber, has occurred. Based on the determination, the control unit can be configured to generate an output, such as an output to a user via a display, wherein the output reflects to the user whether a change has occurred.

In some embodiments, a substrate can include one or more sensor, e.g., a plurality of sensors, configured to detect the presence and/or absence of a liquid, e.g., a biological sample, in one or more of the reaction chambers. In some instances the sensors are operatively connected to the control unit and send an input thereto based on a detected presence and/or absence of a sample. For example, a control unit can generate an output which activates a heating element of a device to heat contents, e.g., a biological sample, of one or more reaction chambers by transmitting thermal energy via an adhesive layer to the reaction chambers when an input from a sensor indicating the presence of a biological sample in a reaction chamber is received. In some versions, the one or more sensors can be configured to detect an optical property, e.g., a wavelength of light, e.g., color, and/or a change in an optical property, such as a wavelength of light emitted from contents of a reaction chamber, e.g., a biological sample.

In some aspects, substrates according to the subject embodiments include one or more light source configured to emit light. Such light sources can be operatively coupled to the one or more sensors and/or control units such that when a sensor detects a liquid, e.g., a biological sample, in the one or more reaction chambers, the light source emits light. Such light sources can also be operatively coupled to the one or more sensors and/or control units such that when an optical property modification occurs or does not occur in the one or more reaction chambers, the light source emits light. Light sources according to the subject embodiments can also include one or more light emitting diode (LED).

In some instances, the subject devices include one or more display for displaying one or more output, e.g., reaction result, and/or status, to a user. In some versions, the devices also include an interface for receiving an input, wherein the interface is operatively coupled to the control unit.

A wireless signal transmitter and/or a wireless signal receiver can also be included in the subject devices. A wireless signal transmitter can be operatively coupled to the control unit and can be configured to transmit a signal, such as an audio signal, from the control unit to, for example, a wireless receiver operatively coupled to one or more other device, such as a second central processing unit and/or a sample analyzer, which can be a mobile device, such as a cellular telephone. The wireless signal receiver can be configured to receive a signal and transmit it for processing by the control unit.

The subject devices can also include a housing. Such a housing can include a first portion and a second portion operatively coupleable, e.g., mateable, e.g., snapedly coupleable, with the first portion to encapsulate the sample receiving cartridge, substrate and adhesive layer. In some versions, a second portion is substantially flat and a first portion is composed of five walls separated by edges and configured to contain, e.g., fully contain, one or more other components of a device, such as by retaining the components between at least two portions, e.g., opposite walls, thereof. In some versions a second portion makes up a bottom surface of the housing and the housing includes an inlet opening in a top surface of the housing opposite the bottom surface.

Housings according to the subject disclosure can be composed of one or more layers of material, e.g., a polymeric material, as described herein, and can be shaped substantially as a rectangular box. The housings can include one or more inlet opening providing access, e.g., fluidic access, to an inlet of a sample receiving cartridge so that a biological sample can be loaded into the cartridge therethrough. In some versions, such an opening is on a top surface of a device and/or is in a first portion.

In some aspects, a housing has a volume and/or defines an exterior or interior volume, sufficient to contain any of the described components therein. A housing can have a volume, for example, of 1 $cm^3$ to 500 $cm^3$, such as from 10 $cm^3$ to 200 $cm^3$, such as from 50 $cm^3$ to 150 $cm^3$. In some instances, a housing can also have a volume of 1 $cm^3$ or more, such as 50 $cm^3$ or more, such as 100 $cm^3$ or more, such as 200 $cm^3$ or more, such as 300 $cm^3$ or more, such as 500 $cm^3$ or more. A housing can also have a volume of 500 $cm^3$ or less, such as 300 $cm^3$ or less, such as 200 $cm^3$ or less, such as 100 $cm^3$ or less, such as 50 $cm^3$ or less, such as 10 $cm^3$ or less.

In some aspects, the subject devices include one or more adhesive layer operatively connecting a sample receiving cartridge and a substrate. As is shown, for example, in FIG. 3, such a layer can also form a wall of each of the one or more reaction chambers. In forming a wall, an adhesive layer can seal and/or extend over an opening, e.g., a supplementary opening, at an end of a reaction chamber. In some versions, a supplementary opening is a first end of a reaction chamber and a venting opening is at a second end of the chamber opposite the first end. An adhesive layer and/or a portion thereof, e.g., a sheet and/or an adhesive material can define an end of a reaction chamber and/or sealably contain one or more solid and/or fluid media, e.g., a biological sample and/or a modifying reagent and/or an amplification composition within the reaction chamber. In various embodiments, an adhesive layer can be operatively coupled to a sample receiving cartridge such that the adhesive layer fluidically seals one or more openings, e.g., an opening at an end, of one or more reaction chambers of the cartridge.

An adhesive layer can be or include a sheet, e.g., a solid sheet, of one or more materials, e.g., two materials, having a thin and/or planar shape. An adhesive layer or other components of the subject devices can include a top surface and a bottom surface each defining a plane parallel with the other and separated by a thickness. In various embodiments, a sheet is or includes a uniform layer of a single material. An adhesive layer can also be composed of two or more, e.g., three, four, five, or more, etc. sheets laminated to one another. In some versions, the adhesive layers are acrylic adhesive laminates.

In some aspects an adhesive layer can be composed entirely of an adhesive material or can have an adhesive material, e.g., a coating and/or layer of adhesive material, on a first surface and/or one or other surfaces, e.g., a second surface opposite the first. Such an adhesive can be an acrylic adhesive. Accordingly, an adhesive layer can include one or more sheets, e.g., laminated sheets, and have an adhesive material on a top surface and/or a bottom surface thereof. One layer of adhesive material can operatively connect the adhesive layer with a substrate and/or another layer of adhesive material can operatively connect the adhesive layer and a sample receiving cartridge.

According to some embodiments, a sheet can have a length, a width and a height, also referred to as a thickness. A sheet can be shaped as a rectangular box with the width and length being substantially greater than the thickness. A thickness of an adhesive layer and/or a sheet, e.g., a thickness between a first surface and a second surface opposite the first surface, can be 5 mm or less, 3 mm or less, 1 mm or less, 0.5 mm or less, 0.1 mm or less, or 50 microns or less.

A thickness of an adhesive layer and/or a sheet thereof can also range for example, from 5 mm to 50 microns, such as 3 mm to 0.1 mm, such as 1 mm to 0.1 mm, inclusive. Also, a length and/or width of an adhesive layer and/or a sheet can also range from 1 mm to 2 m, such as from 1 cm to 1 m, such as from 1 cm to 10 cm, such as from 1 cm to 5 cm.

Adhesive layers can be and/or have an area defining any suitable size or shape including a: circle, semi-circle, oval, rectangle, square, triangle, polygon, quadrilateral, or combination thereof. For example, in embodiments where the adhesive layer is a rectangle, the length of the adhesive layer is greater than the width. An adhesive layer can include one or more sheets of solid, uniform, integrated material, and in some versions, may not include any openings therethrough.

In addition, an adhesive layer and/or a sheet thereof can have three edges, four edges, or more than four edges which define the area of the adhesive layer. In various embodiments, the edges meet at corners, e.g., three, four, five, or ten or more corners. In some versions, a first edge of an adhesive layer is opposite a second edge of an adhesive layer and adjacent to a third and/or fourth edge of an adhesive layer. In such an embodiment, the third edge can be opposite a fourth edge and the fourth edge can be adjacent to the first and/or second edge.

Where desired, adhesive layers can each be composed of a variety of materials and can be composed of the same or different materials. The sample receiving modules and/or caps or portions thereof can be composed of polymeric materials, e.g., materials having one or more polymers including, for example, plastic and/or rubber. Such materials can have characteristics of flexibility and/or high strength (e.g., resistant to wear) and/or high fatigue resistance (e.g., able to retain its physical properties for long periods of time regardless of the amount of use or environment). Materials of interest of which adhesive layers or portions thereof described herein can be composed include, but are not limited to: polymeric materials, e.g., plastics and/or elastomers, such as polytetrafluoroethene or polytetrafluoroethylene (PFTE), including expanded polytetrafluoroethylene (e-PFTE), polyester (Dacron™), nylon, polypropylene, polyethylene, high-density polyethylene (HDPE), polyurethane, polydimethylsiloxane (PDMS), one or more acrylic adhesive, silicone adhesive, epoxy adhesive, or any combination thereof. As described, each of such materials can include coatings or layers of adhesive materials, e.g., acrylic adhesive materials, on one or more surface thereof.

In some aspects, an adhesive layer, or a portion thereof, such as a first and/or second laminated layer, does not include an acid. Furthermore, in some versions, an adhesive layer, or a portion thereof, e.g., such as a first and/or second laminated layer, is opaque and/or white. Where an adhesive layer or a portion thereof is white, the white layer provides a uniform background of visual inspection of one or more reaction chambers. In some versions, a layer, e.g., a first layer and/or second layer and/or an adhesive layer, is opaque and/or a color complementary to a reaction start color, e.g., red, orange, yellow, green, blue, indigo, violet, black, gold, silver, brown, or any combination thereof. A reaction start color is the color of the reaction product and/or the optical property modifying reagent before a reaction occurs to sufficiently modifies an optical property of the optical property modifying reagent to allow detection of the modified optical property. The color complementary to a reaction start color can provide sufficient color contrast, e.g., increased color contrast as opposed to a single color, of the reaction chambers such that, for example, detection of the modified optical property may be made by an unassisted human eye.

In some embodiments, an adhesive layer, or a portion thereof, is transparent to light, e.g., visible light. In other versions, an adhesive layer, or a portion thereof, is reflective, e.g., entirely or substantially reflective to light, e.g., visible light. Also, as noted herein, an adhesive layer can include a first layer laminated with a second layer. In such embodiments, for example, a first layer does not include an acid and/or a second layer is opaque and/or white.

Additionally, in various aspects, an adhesive layer, or a portion thereof such as a sheet, has a thermal conductivity ranging from 0.1 W/m-K to 10 W/m-K, such as 0.1 W/m-K to 5 W/m-K, such as 1 W/m-K to 5 W/m-K.

Also, an adhesive layer can be a patterned adhesive layer. In such embodiments, the adhesive layer can be or have a portion that is porous and/or includes one or more opening extending from a first surface of an adhesive layer to a second surface of the adhesive layer opposite the first surface such that one or more contents, e.g., liquids, of a reaction chamber can pass therethrough. As such, in some aspects, one or more contents, e.g., liquids, of a reaction chamber can contact a substrate and/or one or more components thereof, e.g., a sensor and/or a heating element, directly while an assay is performed.

Also, in various aspects, and where appropriate as referred to herein, a biological sample can, in some versions be a prepared biological sample. As discussed above, a prepared biological assay sample is a biological assay sample which has been processed for example by exposing the sample to a preparation solution, such as a solution including a lysing agent, such as a detergent. Accordingly, in some embodiments, a biological sample is a lysate. Such preparation can enable the prepared biological sample to react, for example, with an amplification composition and/or an optical property modifying reagent upon exposure thereto. The exposure can include lysing cells of the sample with a lysing agent of the preparation solution and/or extracting nucleic acids therefrom. Such extracted nucleic acids can be released into a resulting prepared sample solution. In some embodiments, a step of extracting genomic deoxyribonucleic acid (DNA) from a biological sample is included. Where desired, the preparation solution is a nucleic acid amplification preparation solution and exposure to the solution prepares nucleic acids of the sample for amplification, e.g., isothermal amplification.

As described herein, the subject methods can be used to detect the presence and/or absence of one or more nucleic acids in one or more reaction chambers. The subject methods can also be applied, for example to detect the presence and/or absence of one or more other biomarkers, such as proteins, in the one or more reaction chambers.

In various aspects, optical property modifying devices contain one or more, e.g., three, assay controls: a sample adequacy control, a positive control, e.g., an internal positive control, and/or a negative control. The sample adequacy control detects, for example, abundant human nucleic acid markers such as housekeeping genes, RNA, and/or human β-actin deoxyribonucleic acid (DNA) to ensure a sufficient swab sample was collected. The positive control amplifies a synthetic oligonucleotide that will be co-packaged and/or co-lyophilized in the reaction well. Such a synthetic oligonucleotide can be included, for example, in a modifying reagent, an optical property modifying reagent and/or an amplification composition. Such a control ensures that the device operates under conditions that allow amplification of genetic markers of interest. The negative control also amplifies the positive control but without the co-lyophilized synthetic oligonucleotide. Such a control ensures the absence of any contaminating self-amplifying amplicon.

Furthermore, the optical property modifying devices or portions thereof, e.g., housings, can include calibrators for an image data analysis algorithm as performed, for example, by a control unit of a sample analyzer. For example a quick response (QR) code, can be a resolution calibration target. Also, a white housing, and specifically a region proximate reaction chambers, can be applied by the sample analyzer for white balance calibration and illumination uniformity calibration. Additionally, housings can include printed color targets for calibrating color change measurements.

Optical property modifying devices can also include one or more code, e.g., a quick response (QR) code, on an exterior of a housing thereof. Such a code can include an identification of assay type, expiration date for the device, serial number, or any combination thereof. A sample analyzer can be configured to read and/or recognize such a code so that a proper identification of the device can be made and the device used accordingly.

Sample Analyzing Devices

Systems according to the subject embodiments can also include one or more sample analyzing devices, also referred to herein as sample analyzers. A sample analyzer can, in various embodiments, be configured to determine, such as by recognizing, one or more characteristics of a sample or aspect thereof. In various embodiments, a sample analyzer is a mobile device, e.g., a hand-held mobile device, such as a cellular telephone and/or a camera.

In some aspects sample analyzers are configured for detecting a modified optical property, as is described herein. Also, in some versions, a sample analyzer is configured to produce a colorimetric assay result based on the detected modified optical property. A colorimetric assay result refers to an output, such as an output conveyed to a user via a display of a sample analyzer, wherein the output reflects to the user whether a change in an optical property, e.g., color, of one or more contents of one or more reaction chambers, has occurred.

In some versions, sample analyzers include a control unit, such as a control unit including a processor, configured to perform a colorimetric analysis of contents, e.g., contents including a biological sample, in one or more reaction chambers. As such, a control unit can be configured to determine, based on an input from an signal generator, such as camera and/or one or more sensors, whether a change in an optical property, e.g., color, of one or more contents of a reaction chamber, has occurred. Based on the determination, the control unit can be configured to generate an output, such as an output to a user via a display, wherein the output reflects to the user whether a change and/or what type or extent of change, has occurred.

In some aspects, a sample analyzer or a portion thereof, e.g., a control unit, can include a camera control. Such a control can evaluate, such as a by performing a check on, camera hardware to ensure appropriate parameters, e.g., resolution and/or shutter speed, to obtain a quality image, such as a clear and/or easily-readable image. As such, a user can verify if the sample analyzer can be applied, e.g., effectively applied, to obtain and/or read and/or analyze one or more images before and/or after one or more images are taken. Also, in some aspects, a sample analyzer or a portion thereof, e.g., a control unit, can include a processor control. The processor control can ensure the processor is suited for an image data analysis algorithm applied by the processor to evaluate the modified optical property image data, as described herein.

Also, in some versions, a sample analyzer is configured for obtaining modified optical property image data. Modified optical property image data is image data, such as recorded image data, e.g., a photo and/or video, e.g., a digital photo and/or video, of an optical property modification or lack thereof in one or more reaction chamber. A sample analyzer can also include a database including stored analysis data, e.g., modified optical property image data or features thereof and associated data, for analyzing, such as by comparing with, modified optical property image data obtained by the sample analyzer to thereby generate an assay result, e.g., a colorimetric assay result. Analysis data can include one or more characteristics or classifications, e.g., names, numbers, or other designations, etc., associated with a particular image aspect, e.g., brightness, color, shape and/or size of one or more aspects of an image. Furthermore, optical property image data obtained by the sample analyzer can also be added to and/or stored in a database of a sample analyzer for later communication to an external source, reference and/or analysis.

Also, an assay result, e.g., a colorimetric assay result, can also be generated manually by evaluating one or more aspects of modified optical property image data and/or analysis data associated therewith displayed on a display of a sample analyzer and/or entering one or more input into the analyzer based on the displayed data. A diagnosis can also be made directly by evaluating one or more aspects of modified optical property image data and/or analysis data associated therewith displayed on a display of a sample analyzer and making a diagnosis decision based on the displayed data.

Also, sample analyzers can include one or more power source, processor, display, user interface, wireless signal transmitter, wireless signal receiver, housing, or any combination thereof operatively coupled to one another. Control units of sample analyzers can have any of the features of control units of the other devices described herein. Also, power sources and other elements, e.g., displays, housings, etc., of sample analyzers can have any of the characteristics of power sources or the other devices, e.g., displays, housings, etc., described herein.

Figure 16:
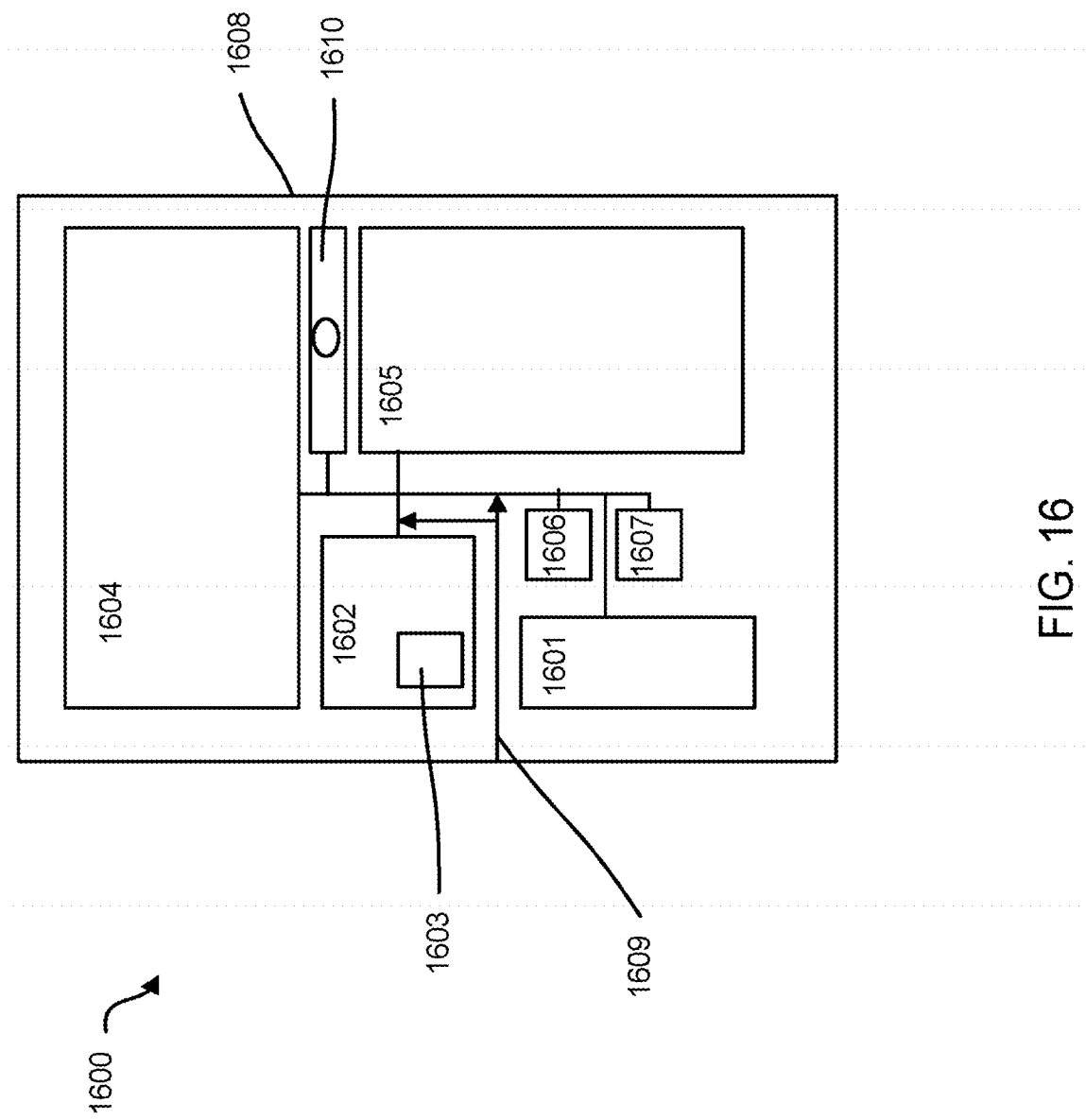
FIG. 16 provides a view of a device according to embodiments of the present disclosure.

A schematic embodiment of a sample analyzer is provided in FIG. 16. FIG. 16 shows a sample analyzer 1600 power source 1601, control unit 1602, processor 1603, display 1604, user interface 1605, wireless signal transmitter 1606, wireless signal receiver 1607, camera 1610 for obtaining modified optical property image data, and housing 1608. The components are integrated with one another by operative connections 1609.

In some versions of the subject embodiments, the sample analyzers include one or more application, which can include a set of instructions which can be stored on a computer readable medium, executable by the processor and/or transferable, e.g., downloadable, to the sample analyzer, such as into a memory of a sample analyzer. Such an application can be configured to check to ensure compatibility of sample analyzer hardware when it is transferred to the sample analyzer. If the compatibility is not ensured, the application will not allow further operation.

Also, in various aspects of the devices, a sample analyzer and/or an application thereon, can be configured such that an optical property modifying device portion, e.g., housing, must be clearly presented without skew to a camera of the analyzer. In some embodiments of the devices, a sample analyzer and/or an application thereon, can be configured such that the resolution, white balance, and/or illumination uniformity of an image must all be within specified ranges for the sample analyzer to perform an analysis. If any of such aspects are outside specific ranges, the application will not scan the cartridge and no analysis will be made.

Analysis results can be interpreted using the sample analyzer performing the image analysis. Also in some versions, amplification a discernible optical property, e.g., color, change which can be quantified by an image analysis algorithm executed by the sample analyzer. In such aspects, a sample adequacy and positive assay control must display a threshold color change and/or the negative assay control must display no color change for the result to be considered valid. Also, in some versions, each target nucleic acid is tested in separate chambers, with color change indicating presence of the nucleic acid target. If any of the control channels do not display a color change, the test is considered can be considered invalid, for example, by the sample analyzer or by a user.

Methods of the Invention

The present disclosure includes methods of determining one or more characteristics of a biological sample or an aspect thereof, such as a nucleic acid amplification sample, based on a modified property, e.g., a modified optical property, of the sample. In some versions, the methods include applying the subject systems devices thereof to perform one or more steps of a biological assay as described herein.

For example, in various embodiments, the present disclosure includes methods of delivering a preparation solution and/or sample, such as a biological assay sample. Delivering a sample can include moving, e.g., flowing, a preparation solution and/or sample, such as a prepared biological assay sample, to a particular location, such as a location outside a sample delivery device and/or a specific location intended by a user, such as an optical property modifying device or a portion thereof, such as one or more reaction chambers.

Also, in some versions, the methods include introducing a preparation solution and/or a biological sample into an optical property modifying device by flowing the solution and/or sample into one or more reaction chambers of a sample receiving cartridge of the device via one or more sample receiving openings. Such a solution and/or sample can first be introduced to an inlet operatively coupled to the one or more reaction chambers by contacting the sample with the inlet and then flowed from the inlet into the reaction chambers.

Sample Collection and Preparation

According to various aspects, the subject methods include collecting a biological sample, such as collecting a biological sample with a sample collector. Such a sample can include, for example, human saliva, urine, human mucus, blood, or a solid tissue such as buccal tissue. Such a sample can also include bacteria or spores. Collecting can include contacting, e.g., rubbing and/or scraping, the sample collector against one or more surfaces of a subject and/or surfaces of a biological sample of a subject, such as a liquid, e.g., saliva and/or blood and/or mucus, sample extracted from the subject. Such contacting can be performed, for example for 10 seconds or less, 20 seconds or less, 30 seconds or less, or 1 minute or less. As such, in some versions, collecting includes extracting one or more biological samples from the subject. In some versions, collecting the biological sample can include instructing a subject to produce a biological sample, such as by spitting onto and/or into a sample collector. Collecting the biological sample can also include retaining a biological sample or a portion thereof, e.g., one or more cells, on the sample collector while, for example transferring the sample collector to an assay device. In some instances, a sample collector is a swab and collecting the biological sample includes swabbing the inside of a subject's mouth and/or nose and/or throat to obtain the biological sample on the collector. In some versions, sample collectors are nasopharyngeal, mid turbinate and/or nasal swabs. Also, in some aspects, the samples are nasal, nasopharyngeal and/or mid turbinate samples. After a biological sample is collected, the methods, in some versions, include processing the biological sample so that it is a prepared biological sample as described herein.

In some embodiments, the methods include inserting a sample collector into a sample receiving module of a sample preparation device. Inserting can include moving one or more portions of the sample collector, e.g., the sample collection portion and/or the handle, into, such as fully into, a sample receiving module via an opening in the module. The inserting can include rubbing one or more portions of the sample collector against an interior wall of the sample receiving module. In some versions, the methods include retaining the one or more portions of the sample collector, e.g., the sample collection portion and/or the handle, within, such as fully within, the sample receiving module after insertion. In some embodiments, the methods include removing the one or more portions of the sample collector, e.g., the sample collection portion and/or the handle, from the sample receiving module after insertion. Also, in some aspects, a sample receiving module includes a seal, e.g., a breakable and/or frangible seal, such as a foil seal, over an opening and wherein inserting the sample collector into a sample receiving module of a sample preparation device includes breaking the seal, such as breaking the seal by exerting force on it with the sample collector, and inserting at least a portion of the sample collector through the opening.

In some instances, the methods include inserting a biological sample, e.g., a biological sample including a nucleic acid, into a nucleic acid preparation solution of a sample receiving module of a sample preparation device. In some versions, such an insertion produces a prepared nucleic acid amplification sample. In some aspects, the methods include inserting the sample collector by exposing the biological sample to a preparation solution within the sample receiving module to produce a prepared biological assay sample. Such exposure can include immersing the biological sample and/or sample collector entirely within the preparation solution. Also, producing the prepared biological sample can include exposing the preparation solution to one or more aspects of the biological sample, wherein such exposure results in a change in the biological sample, e.g., cell lysing, such that the modified biological sample can be further processed and/or analyzed.

A prepared biological assay sample is a biological assay sample which has been processed by exposing the sample to a preparation solution, as described above. Such exposure can prepare the sample for further analysis and can include lysing cells of the sample with a lysing agent of the preparation solution and/or extracting nucleic acids therefrom. Such extracted nucleic acids can be released into a resulting prepared sample solution. In some embodiments, the methods include a step of extracting genomic deoxyribonucleic acid (DNA) from a biological sample. In some versions, the preparation solution is a nucleic acid amplification preparation solution and exposure to the solution prepares nucleic acids of the sample for amplification, e.g., isothermal amplification. After such exposure, the sample is a prepared nucleic acid amplification sample.

The subject methods can include pressurizing the sample receiving module. For example, in various aspects, the methods include operatively coupling a cap of the sample preparation device to the sample receiving module and thereby pressurizing the sample receiving module. Operatively coupling the cap of the sample preparation device to the sample receiving module can include adhesively, snapedly, and/or screwably, fastening the cap to the sample receiving module. Such coupling can also be removable and as such, reversible and repeatable a plurality of times. Such operative coupling can also in include sealing the sample receiving module or apportion thereof, e.g., a fluid container, with the cap. Operatively coupling the cap and the sample receiving module can include screwing the cap to the module by rotating the cap with respect to the module while screwable threads of the two elements are engaged. Operatively coupling the cap and the sample receiving module, in some embodiments includes inserting the sample receiving module or a portion thereof, e.g., an end, into a cap. Operatively coupling the cap and the sample receiving module, in some embodiments includes inserting the cap, or a portion thereof, e.g., a pressurizing component and/or an end, into, such as fully into, the sample receiving module or a portion thereof, e.g., a fluid container.

In some aspects of the methods, the sample receiving module includes a first attachment element and/or the cap includes a second attachment element. In such embodiments, operatively coupling a cap of the sample preparation device to the sample receiving module includes mateably connecting the first and second attachment elements, such as screwing the first attachment element, e.g., a thread, into the second attachment element, e.g., a groove, by rotating the cap with respect to the sample receiving module while the attachment elements are engaged.

Operatively coupling the cap of the sample preparation device to the sample receiving module also includes pressurizing the sample receiving module or a portion thereof, e.g., a fluid container. The pressurizing includes exerting force on one or more fluid, e.g., a liquid and/or gas, within the sample receiving module, such as air and/or preparation solution with a pressurizing component. As the pressurizing component extends further into the sample receiving module, the pressure increases because the pressurizing component exerts more force on the one or more fluid. The methods also include retaining the pressurizing component in a particular position within the sample receiving module, wherein, in such a configuration, the pressure in the module remains constant while the sample receiving module remains sealed.

In some instances, the methods include pressurizing the sample receiving module to a pressure ranging from 50 Pa to 50000 Pa, such as 500 Pa to 50000 Pa, such as 1000 Pa to 50000 Pa, such as 5000 Pa to 50000 Pa, such as 10000 Pa to 30000 Pa, such as 15000 Pa to 25000 Pa, each inclusive. Where desired, the pressurizing component pressurizes the sample receiving module to a pressure of 1000000 Pa or less, such as 50000 Pa or less, such as 30000 Pa or less, such as 10000 Pa or less, such as 5000 Pa or less, such as 1000 Pa or less, such as 500 Pa or less, such as 50 Pa or less. In some versions, the pressurizing component pressurizes the sample receiving module to a pressure of 1000000 Pa or more, 50000 Pa or more, 30000 Pa or more, 10000 Pa or more, or 5000 Pa or more, 1000 Pa or more, 500 Pa or more, or 50 Pa or more. As used herein, the term pressure can refer to peak pressure.

Figure 38:
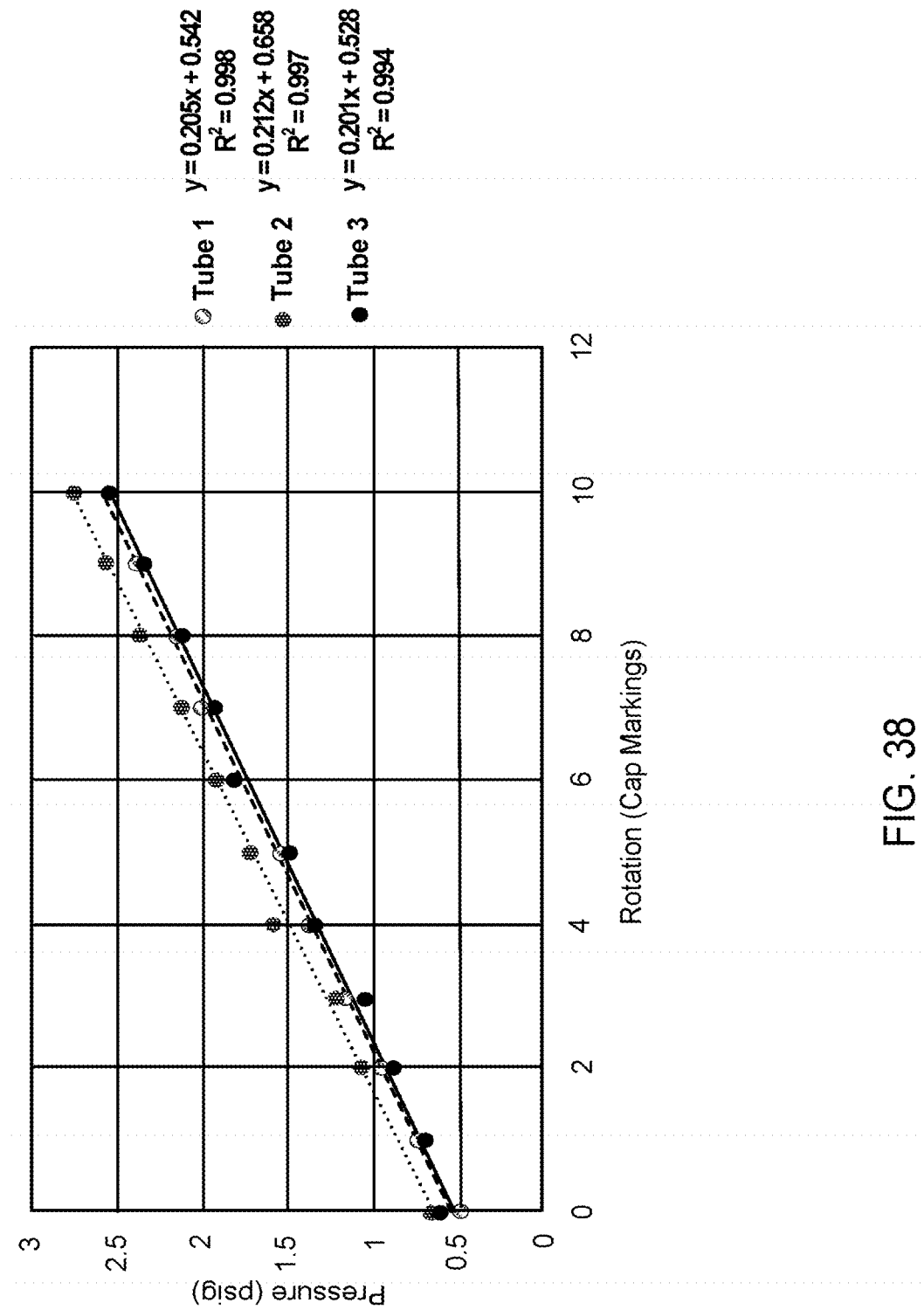
FIG. 38 provides pressure generated in a sample preparation device upon pressurization by the application and rotation of a cap, e.g., screw cap, to the top of the device according to embodiments of the subject disclosure.

One example of pressurization according to the subject embodiments is illustrated in FIG. 38. Specifically, FIG. 38 provides a graph illustrating pressure generated in a sample preparation device upon pressurization by the application and rotation of a cap, e.g., screw cap, to the top of the device according to embodiments of the subject disclosure. As is shown, pressure is linearly related to displacement, and therefore rotation, of the cap.

Where appropriate, the methods include storing reagents with long shelf-life at room temperature. Such storage can include storing stable reagents, e.g., preparation solutions and/or staging reagents, in liquid form and/or unstable reagents, e.g., preparation solutions and/or staging reagents, in dry, e.g., lyophilized, form. Storage according to the subject methods can be performed for a length of time of 1 day or less, such as 1 month or less, such as 6 months or less, such as 1 year or less and/or one year or more. The methods also can include sample loading into, for example a sample analyzing device.

In various aspects, a solution, e.g., a lysis solution, is heated. Such heating can be achieved using a heat source such as an exothermic reaction. Furthermore, in some embodiments, the methods include adding to contents of a sample receiving module one or more heating reagents which, when mixed, cause an exothermal reaction. Such a reaction can, for example, heat a sample for lysis.

Exothermal reactions can generate heat and/or gas Exothermal reactions can include the hydration of a mixture composed of encapsulated and/or non-encapsulated oxides such as calcium oxide and/or magnesium oxide and dehydrated and/or hydrated zeolite, or any combinations thereof. Such a process can be coupled with control of pH of the mixture through compounds such as Citric acid, or combination exothermic mixes, such as Cao and Mg—Fe. Modulation can include timed/controlled release from encapsulated reactants and can include particles with tailored size distribution and different burn characteristics. Phase change materials (PCM) can be used to control the heat stability of the reaction. PCMs include, for example, organics (paraffins, non paraffins and fatty acids) and inorganics (salt hydrates).

Also, in some versions, the methods include adding one or more gas-producing regents, e.g., liquid reagents, that, when mixed, generate a gas and further pressurize a subject device or a portion thereof, e.g., a sample receiving module. Such reagents may be the same or different reagents than those applied in an exothermic reaction. The gas produced by such reagents may be applied in propelling at least a portion of the prepared biological assay sample out of the sample receiving module. In some forms, a chemical reaction is used to produce gases that can increase pressure, e.g., pressure which can be applied for driving out a liquid, inside the module. The methods, in some embodiments, include generating fluid driving pressure and/or dispensing a prepared sample and/or reagent and sample mix into an analyzing device with the pressure. Also, according to various embodiments, a user can pressurize a sample receiving module on-demand before, during and/or after reagents, e.g., preparation solutions and/or staging reagents, are exposed to a biological sample.

An embodiment of the subject methods is illustrated, for example, by FIG. 1 and FIG. 15. In various embodiments, a device according to the methods includes a sample receiving module 101 including a fluid container 102 for receiving one or more portions of a sample collector therein, e.g., entirely therein, a preparation solution 104, and a first attachment element 103. Such a device 100 can also include a cap 105 operatively, e.g., removably, coupleable to the sample receiving module 101 and including a pressurizing component 106, and a second attachment element 107 operatively coupleable with the first attachment element 103. As noted above, the methods include operatively coupling the cap 105 and the sample receiving module 101. Such a process can be performed by causing a device to go from a conformation as shown in FIG. 1 or FIG. 2 to a conformation as shown in FIG. 15. Accordingly, the methods can include inserting a pressurizing component 106 into, e.g., entirely into, the sample receiving module 101. The methods can also include expelling fluid from sample receiving module 101 when the first attachment element 103 is operatively coupled to the second attachment element 107 by, for example, actuating a valve 108 of the device.

Additionally, and as is illustrated, for example, by FIG. 2, the methods include actuating an inner body 214 within an outer body 209 when a cap 205 is operatively coupled to a sample receiving module 201. Operatively coupling the cap includes exerting force on the inner body 214 with the cap 205 or a portion thereof, such as a pressurizing component 206, so that the inner body 214 moves. Such actuating can also include breaking a breakable seal 213 with the one or more piercing member 216 and placing the first chamber 210 in fluidic communication with the second chamber 215. Also, in some versions, the outer body 209 includes a staging reagent 217 and the methods include placing the staging reagent 217 in fluidic communication with the second chamber 215. In some aspects, the staging reagent 217 includes one or more lyophilized agents, such as one or more lyophilized cell lysing reagent, and placing the staging reagent 217 in fluidic communication includes hydrating the reagent with the preparation solution 204 and/or exposing the staging reagent 217 to the biological sample.

In various instances, the methods include operatively coupling a sample preparation device with an optical property modifying device, e.g., a nucleic acid amplification sample optical property modifying device. Operatively coupling the devices can include fluidically and/or mateably connecting a valve of a sample preparation device with a valve and/or a receptacle of a nucleic acid amplification sample optical property modifying device. In some versions, the methods include contacting and engaging an outlet and/or valve of a preparation device with that of an optical property modifying device and then rotating either or both valve, such as rotating either or both valve 45° or less, such as 90° or less such as 180° or less, or 180° or more and thereby provide fluidic communication between the two devices. Also, in some aspects, operatively coupling the devices can include inserting a portion, e.g., a connector, such as a valve, of a sample preparation device into an optical property modifying device. In some aspects, operatively coupling the devices can include inserting a portion, e.g., a connector, such as a valve, of an optical property modifying device into a sample preparation device.

Some embodiments of the subject methods also include depressurizing the sample receiving module by transmitting a portion of the prepared nucleic acid amplification sample out of the sample receiving module, such as out of the module and into one or more reaction chambers of the optical property modifying device. In some versions, the chambers include an optical property modifying reagent and an amplification composition, and transmitting a portion of the prepared sample into the one or more reaction chambers of the optical property modifying device generates a reaction mixture, e.g., a nucleic acid reaction mixture. As described further below, a reaction mixture is a mixture which can be employed in one or more reactions as designated herein. A reaction mixture can also include, for example, an amount of a biological sample, e.g., a prepared biological sample, and an amplification composition, e.g., a nucleic acid amplification composition, and/or one or more optical property modifying reagent, or any combination thereof. A nucleic acid reaction mixture is a reaction mixture which includes an amount of a nucleic acid amplification composition.

According to some aspects, embodiments of the subject methods include delivering a sample, e.g., a prepared biological assay sample, by depressurizing the sample receiving module by flowing and/or discharging at least a portion of the contents of the sample receiving module, such as a prepared biological assay sample, preparation solution, unprepared biological sample and/or air, out of the sample receiving module. Depressurizing includes providing fluidic communication, such as via a valve, e.g., a reversibly actuable valve, between a fluidic container of a sample receiving module and an environment, such as a sample analysis device, outside the sample receiving module. Such depressurization can include actuating the valve from a sealed conformation to an unsealed conformation and thereby providing such fluidic communication via an opening, e.g., a depressurization opening, therethrough. In various embodiments, an opening such as a depressurization opening does not allow passage of a gas, such as air, therethrough. In such embodiments, air is not passed through the opening while, for example, a liquid is passed through the opening, the plunger actuates toward the opening and/or the plunger is not actuated.

Where desired, a device according to the subject embodiments includes a breakable and/or frangible seal, such as a foil seal, for sealing a valve, e.g., a reversibly actuable valve. In such embodiments, depressurizing the sample receiving module includes breaking the seal so that a fluid can flow from a first side of the seal to a second side of the seal opposite the first. Breaking the seal can include exerting force on it with fluid within the pressurized container by opening the valve. Also, in some versions, the subject devices can include a filter for filtering fluid discharging from the sample receiving module. A filter can be configured to filter a sample fluid prior to discharging the sample fluid through the valve. As used herein the phrase "sample fluid" refers to fluid comprising sample that optionally can include any one or more reagents mixed with the sample within the sample preparation device. In such embodiments, the methods include filtering by flowing one or more fluid, e.g., a prepared biological assay sample and/or air, through the filter. Flowing can be achieved by passing the fluid through the material of the filter, such as through one or more entire surface, e.g., a top and/or bottom surface of the material. The filtering can be performed on the fluid, e.g., sample, discharging from a depressurizing sample receiving module through, for example, a valve.

In some versions of the methods, the sample receiving module includes an outer body forming a first chamber, and a fluid container of a sample receiving module includes a breakable seal and an inner body forming a second chamber which can be sealed at an end by the breakable seal, wherein the inner body is actuable within the outer body. In such embodiments, operatively coupling a cap of the sample preparation device to the sample receiving module includes actuating, such as by sliding, the inner body within the outer body to break the seal and place the first and second chambers in fluidic communication. Operatively coupling, such as by screwing, a cap of the sample preparation device to the sample receiving module can include exerting force on the inner body with the cap or a portion thereof, e.g., the pressurizing component, by contacting the two components. Actuating the inner body within the outer body includes moving the inner body in a linear direction toward a valve of the sample receiving module and/or away from the cap. In some versions, the outer body includes a piercing member and actuating the body includes piercing the seal on the inner body with the piercing member. Also, in various aspects, an outer body includes a staging reagent, e.g., a lyophilized staging reagent, and placing the first and second chambers in fluidic communication includes mixing the preparation solution and/or biological sample and the staging reagent and/or hydrating the staging reagent.

Also included in the subject methods are methods for preparing a biological assay sample including operatively coupling a cap and a sample receiving module of a biological assay sample preparation device, wherein the cap includes a seal and a plunger including a piercing member, e.g., a needle and/or sharpened cylindrical protrusion. In such methods, operatively coupling can include inserting, e.g., fully inserting, a portion of a cap, e.g., an insertion portion and/or an end, into a sample receiving module or a portion, e.g., chamber thereof. Such insertion can form a sealed fluidic connection between chambers of each element. Also, an insertion portion can be cylindrical and can extend at and end from and have a smaller diameter than other portions of the cap. An insertion portion can be at a first end of a cap opposite a second end, wherein the second end includes a plunger.

The methods also, in some embodiments include advancing the plunger to pierce the seal with the piercing member and thereby placing a first chamber in fluidic communication with a second chamber and preparing a biological assay sample. Such advancing can include moving, such as by sliding, the plunger in a linear direction, such as a direction toward a sample receiving module or a portion thereof, e.g., a valve, and/or a direction along an axis of symmetry of the plunger and/or the cap and/or the sample receiving module. The plunger can include a first end and a second end opposite the first end and including the piercing member, and wherein advancing the plunger includes exerting force on a first end of the plunger in a direction toward the second end. Advancing the plunger can be performed manually by, for example, contacting and exerting force directly on an end of the plunger, as can be performed with the device embodiment shown for example, in FIGS. 3A and 3B and 4. Advancing the plunger can also be performed by, screwing the cap to the sample receiving module, such as by twisting the two components with respect to one another while their respective attachment elements are engaged, as can be performed with the device embodiment shown for example, in FIGS. 5A and 5B.

In some versions, the plunger includes a body portion, e.g., a cylindrical body portion, which is received entirely within other portions of the cap when the plunger is advanced, and a contacting portion at an end of the body portion and which can be contacted by a user directly to advance the plunger. Also, as is shown, for example in FIGS. 5A and 5B, in some versions, the plunger is retained entirely within other portions of the cap while it is advanced.

Where desired, a first chamber, e.g., first chamber of a cap, includes a preparation solution, and a second chamber, e.g., second chamber of a sample receiving module, includes a staging reagent. In such embodiments, the methods can include placing the first chamber in fluidic communication with the second chamber and mixing the preparation solution and the staging reagent. Also, in some embodiments of the methods, delivering the prepared biological assay sample includes actuating, such as by rotating 45° or less, or 90° or less, a reversibly actuable valve of the sample preparation device and flowing at least a portion of the prepared biological assay out of the sample receiving module through the valve, e.g., through an opening in the valve.

Also, and as is representatively shown, for example, by FIGS. 6A-6C, the methods include using a device 600 composed of a sample receiving module 601 including a fluid container 602 for receiving one or more portions of a sample collector 611 therein, e.g., entirely therein, and a first attachment element 603. The methods include operatively coupling a cap 605 and the sample receiving module 601, as is shown in FIG. 6B. The sample receiving module 601 in turn includes a preparation solution, e.g., a lysis buffer 606, and a second attachment element 607 operatively coupleable with the first attachment element 603 when the components are operatively coupled.

In some aspects, the methods include operatively coupling the sample receiving module 601 and the cap 605, by screwing the sample receiving module 601 and the cap 605, and thereby piercing a seal 604 with a piercing member 608 and placing a first chamber 609 in fluidic communication with a second chamber 610. As such, operatively coupling the sample receiving module 601 and the cap 605, such as by screwing the sample receiving module 601 and the cap 605 together, includes exposing a preparation solution 606 to a sample on a sample collector 611 and thereby producing a prepared, e.g., lysed, sample 612.

Once the prepared, e.g., lysed, sample 612 is made, the methods include operatively coupling the sample receiving module 601 to a pressurizing module 615. Operatively coupling can be performed by attaching, such as by screwing, an attachment element 613 of a sample receiving module 601 and a second attachment element 614 of a pressurizing module 615. The pressurizing module 615 also includes a buffer, e.g., a dilution buffer 616. Operatively coupling the sample receiving module 601 and the pressurizing module 615, as is shown in FIG. 6C, can include placing the prepared sample 612 in fluidic communication with the dilution buffer 616 so that the prepared sample 612 is diluted and pressurizes the sample receiving module. Such an action can also pierce a seal 617 with a piercing member 618. Thereafter, the methods can include delivering the diluted prepared sample out of the device 600 for further analysis using the pressure within the device to push the diluted prepared sample out of the device 600.

As is shown representatively, for example, by FIGS. 7A-7D, the methods include using a device 700 including a sample receiving module 701 including a fluid container 702 for receiving one or more portions of a sample collector 711 therein, e.g., entirely therein, and a first attachment element 703. Such a device 700 can also include a cap 705 and the methods can include operatively coupling the cap 705 to the sample receiving module 701. The cap 705 also can include a preparation solution, e.g., a lysis buffer 706, and a second attachment element 707 operatively coupleable with the first attachment element 703. Operatively coupling the cap 705 and the sample receiving module 701 also includes pressurizing the sample receiving module 701. The sample receiving module 701 can also include a buffer, e.g., a dilution buffer 718 in a buffer container 719 therein.

In the embodiment provided, operatively coupling the sample receiving module 701 and the cap 705, as is shown in FIG. 7B, such as by screwing the sample receiving module 701 and the cap 705, includes piercing a seal 704 with a piercing member 708 and placing a first chamber 709 in fluidic communication with a second chamber 710. As such, operatively coupling the sample receiving module 701 and the cap 705, such as by screwing the sample receiving module 701 and the cap 705 together, includes exposing preparation solution 706 to a sample on a sample collector 711 and thereby producing a prepared, e.g., lysed, sample 712.

After the prepared, e.g., lysed, sample 712 is made, the methods include operatively coupling the sample receiving module 701 to, such as by lowering onto, a cartridge 715. Such operative coupling can include actuating a fluidic communication element 717 and/or opening a valve 716, e.g., poppet valve, of the fluidic communication element 717. The methods also include actuating the fluidic communication element 717 toward the cap 705 by exerting force on it with the cartridge 715. Opening the valve 716 in turn includes releasing the prepared sample 712 into the dilution buffer 718 in the buffer container 719 and producing a prepared diluted sample 720. Operatively coupling the sample receiving module 701 and the cartridge 715, as is shown in FIG. 7D, includes delivering the prepared diluted sample 720 out of the sample receiving module 703 and into the cartridge.

Furthermore, and as is illustrated representatively, for example, by FIGS. 8A-8D, the methods include using a device 800 including a sample receiving module 801 including a fluid container 802 for receiving one or more portions of a sample collector 811 therein, e.g., entirely therein. Such a device 800 can also include a cap 805 and the methods can include operatively coupling the cap 805 to the sample receiving module 801. The cap can also include a preparation solution, e.g., a lysis buffer 806.

Operatively coupling the cap 805 and the sample receiving module 801 may not pressurize the sample receiving module 801 but may include placing the lysis buffer 806 in fluidic communication with a sample on the sample collector 811 and thereby producing a prepared, e.g., lysed, sample 812.

The device 800 also includes a pressurizing chamber 816 operatively coupled to the sample receiving module 801 and including a valve 817, e.g., a one-way valve, to provide fluidic communication therebetween. The methods include actuating a plunger 818 to create positive and/or negative pressure within a pressurization chamber 816. The pressurizing chamber 816 also includes a buffer, e.g., a dilution buffer 821. The pressurizing chamber 816 also includes an expulsion valve 819 and the methods include expelling a diluted prepared sample 820 therefrom by actuating the plunger 818.

According to the subject methods, when the cap 805 is operatively coupled to the sample receiving module 801 to produce a prepared sample 812, the methods include actuating the plunger 818 in a first direction, as is shown in FIG. 8C, and propelling the prepared sample 812 from the sample receiving module 801 into the pressurizing chamber 816 via valve 817 and thereby producing a diluted prepared sample 820. The plunger 818 can then be actuated in a second direction opposite the first, as is shown in FIG. 8D, to thereby propel the diluted prepared sample 820 out of the pressurizing chamber 816 via expulsion valve 819.

As is shown representatively, for example, by FIGS. 8A-8D, the methods include using a device 900 which includes a sample receiving module 901 including a fluid container 902 for receiving one or more portions of a sample collector 911 therein, e.g., entirely therein. Such a device 900 can also include a cap 905 operatively, e.g., removably, coupleable to the sample receiving module 901 and including a preparation solution, e.g., a lysis buffer 906. As such, the methods can include operatively coupling the cap 905 and the sample receiving module 901.

Operatively coupling the cap 905 and the sample receiving module 901 may not pressurize the sample receiving module 901 but may place the lysis buffer 906 in fluidic communication with a sample on the sample collector 911 and thereby produce a prepared, e.g., lysed, sample 912. The sample receiving module 901, cap 905 and other provided components can have any of the characteristics or combination of characteristics of sample receiving modules, caps and/or other corresponding components described herein.

In some embodiments, the device 900 also includes a pressurizing chamber 916 and the methods include operatively coupling the pressurizing chamber 916 to the sample receiving module 901. The pressurizing chamber 916 also includes a plunger 918, e.g., a manually actuable plunger, which and the methods include actuating the plunger to create positive and/or negative pressure within the pressurizing chamber 916.

The device 900 is configured such that when the cap 905 is operatively coupled to the sample receiving module 901 to produce a prepared sample 912, the plunger 918 can be actuated in a first direction according to the subject methods, as is shown in FIG. 9C, to propel the prepared sample 912 from the sample receiving module 901 and into the pressurizing chamber 916 via vent 917 and thereby produce a diluted prepared sample 920. Actuating the plunger 918 in such as direction can include unsealing a vent 917. The methods also include actuating the plunger 918 in a second direction opposite the first, as is shown in FIG. 9D, and propelling the diluted prepared sample 920 out of the pressurizing chamber 916 via the valve 919. Actuating the plunger 918 in such as direction can include sealing the vent 917 and preventing further fluid communication therethrough.

As is illustrated representatively, for example, by FIGS. 10, 11 and 12, the methods include using a device, e.g., device 1000, 1100, and/or 1200, which includes a sample receiving module 1001 including a fluid container 1002 for receiving one or more portions of a sample collector 1011 therein, e.g., entirely therein. As such, the methods include inserting such a sample collector therein. Such a device 1000 can also include a cap 1005 operatively, e.g., removably, coupleable to the sample receiving module 1001 and the methods include operatively coupling the cap 1005 and the sample receiving module 1001. In some versions, operatively coupling the cap 1005 and the sample receiving module 1001 includes placing a preparation solution, e.g., a lysis buffer, in fluidic communication with a sample on the sample collector 1011 and thereby producing a prepared, e.g., lysed, sample.

The pressurizing chamber 1016 also includes a plunger 1018, e.g., a manually actuable plunger, and the methods include pushing and/or pulling the plunger in a linear direction, e.g., along a central axis of symmetry of a pressurizing chamber and/or sample receiving module, and thereby creating positive and/or negative pressure within the pressurization chamber 1016 and/or sample receiving module 1001. The sample receiving module 1001 also includes an expulsion valve 1019 and the methods include expelling a diluted prepared sample therefrom upon actuation of the plunger 1018.

The subject methods include actuating the plunger 1018 in a first direction, to propel a buffer from channel 1017 into the sample receiving module 1001 and thereby produce a diluted prepared sample therein and pressurize the sample receiving module. According to the methods, the diluted prepared sample can then be propelled by the pressure out of the sample receiving module 1001 via expulsion valve 1019.

Also, in some versions of the methods, the methods include operatively coupling by screwing the cap 1005 to the sample receiving module 1001. The methods also can include screwing, such as by twisting, the plunger 1018 to actuate it into the pressurizing chamber 1016 to pressurize the pressurizing chamber 1016 and/or the sample receiving module 1001.

As is provided representatively, for example by A-D in FIG. 13, the methods include using a device 1300. Such methods can include storing the device 1300 in a stored configuration, such as that shown in A of FIG. 13. The methods also can include inserting, such as fully inserting, a sample collector as indicated by the arrow into a device 1300 in a sample collector receiving configuration as shown in B of FIG. 13. A device 1300 can also include a cap 1305 and the methods can include operatively, e.g., removably, coupling the cap 1305 to the sample receiving module 1301 and thereby pressurizing the sample receiving module 1301, as is shown in C of FIG. 13.

Furthermore, operatively coupling the sample receiving module 1301 and the cap 1305, as is shown in C of FIG. 13, can include exposing a preparation solution to a sample on a sample collector and thereby producing a prepared, e.g., lysed, sample. Once the prepared, e.g., lysed, sample is made, the methods include operatively coupling, such as fluidically coupling, such as by actuating, such as by rotating, the sample receiving module 1301 about an axis of a coupling component 1317, wherein the operative coupling is via a vent 1316, to a preparation module 1315 of the device 1300.

Operatively coupling the sample receiving module 1301 and the preparation module 1315, as is shown in D of FIG. 13, can include placing the prepared sample in fluidic communication with a dilution buffer so that the prepared sample is diluted in the preparation module 1315. Thereafter, the methods can include moving the diluted prepared sample out of the device 1300 for further analysis using the pressure within the device to push the diluted prepared sample out of the device 1300.

As is shown representatively, for example by A-F in FIG. 14, the methods include using a device 1400 including a sample receiving module 1401 including a fluid container 1402 for receiving one or more portions of a sample collector therein, e.g., entirely therein. Such a device 1400 can also include a cap 1405 and the methods include operatively, e.g., removably, coupling the cap 1405 to the sample receiving module 1401, as is shown in C of FIG. 14. Such a cap 1405 can also include a preparation solution, e.g., a lysis buffer 1406, a seal 1421, and a plunger 1422 including a piercing member 1423. The methods include actuating the plunger 1422 by pushing the plunger 1422 to pierce the seal 1421 with the piercing member 1423, providing fluidic communication between the lysis buffer 1406 and a sample collector in the sample receiving module 1401, and pressurizing the sample receiving module 1401.

After the prepared, e.g., lysed, sample is made, the methods can include flowing the prepared sample to a sample incubation chamber 1424 via an actuating valve 1425 which can include a bimetal valve actuator. Therein, the sample can be incubated according to the subject methods and the incubated sample measured to produce an assay result. The assay result can be displayed to a user via a display 1426 of the device 1400.

Detection

According to some embodiments of the subject methods, the methods include transmitting a biological sample into one or more reaction chambers of a sample receiving cartridge of an optical property modifying device. Transmitting a sample can include moving, e.g., flowing, a sample, to a particular location, such as one or more reaction chambers. Transmitting can include flowing the sample through a sample inlet and/or one or more conduits operatively connecting each of the one or more reaction chambers. Such flowing can include biasing, e.g., pumping, the sample to move through the inlet and/or conduits. The flowing can also include flowing the sample into an opening in the sample inlet through a receptacle opening in the housing of a device.

In various aspects, transmitting a biological sample into one or more reaction chambers includes operatively coupling an optical property modifying device with a sample preparation device and flowing a prepared biological sample from the sample preparation device into the optical property modifying device. As noted above, operatively coupling such devices can include coupling reciprocating connectors, e.g., fluidic connectors, e.g., luer connectors, of each device. In some versions of the methods, the methods include applying the subject devices for removing bubbles from microfluidic systems.

As provided in the subject disclosure, one or more one or more reaction chambers of a device can include one or more modifying reagent, e.g., an optical property modifying reagent. As such, transmitting a biological sample into one or more reaction chambers can include mixing a biological sample with the one or more optical property modifying reagent and thereby generating a reaction mixture including the biological sample and optical property modifying reagent. A reaction mixture can also include, for example, an amount of buffer, water, and/or other compositions such as a biological sample, e.g., a prepared biological sample, an amplification composition, e.g., a nucleic acid amplification composition, and/or one or more optical property modifying reagent, or any combination thereof.

In some aspects, flowing the sample into the one or more reaction includes flowing a gas through a selective venting element of the device and/or contacting the sample with one or more modifying reagent in a reaction chamber. Such a selective venting element can form a wall of each of the one or more reaction chambers, and the one or more reaction chambers can each include a modifying reagent.

The methods, in some embodiments, include contacting the sample liquid with the selective venting element and thereby reducing the permeability of the selective venting element to the fluid, such as by making the selective venting element impermeable to fluid. As such, in some embodiments, the methods include contacting the sample liquid with the selective venting element and thereby advancing the selective venting element from a first conformation to a second conformation, as described herein. In some versions, the methods include flowing an amount, e.g., a small amount, of a liquid, e.g., biological sample, water and/or buffer, into a selective venting elements, or a portion thereof, e.g., a sealing surface, by contacting the element with the liquid. The presence of the liquid within the element seals pores of the element and/or expands the element so that further liquid and/or gas cannot pass into or through the element. Accordingly, the methods include sealing the selective venting element and preventing further passage of liquid or gas, such as by evaporation, into or through the element.

Variations of the methods also include heating a reaction mixture with a heating element of a device. In some versions such heating includes transferring thermal energy to one or more reaction chambers via an adhesive layer. Heating the reaction mixture in turn can generate a reaction product, e.g., a reaction product including amplified nucleic acids and a plurality of protons. More specifically, in some aspects, the heating accelerates a nucleic acid amplification reaction including a nucleic acid and an amplification composition. Such a reaction generates an amplified nucleic acid and a plurality of protons. As such, the methods can include reacting a sample with a modifying reagent and generating a reaction product.

In some instances, a reaction product can include, for example, one or more compositions, e.g., aspects of a biological sample, e.g., amplified nucleic acids and/or protons, which, when reacted with an optical property modifying reagent, result in a modification of one or more optical property. As such, in various embodiments, the methods include reacting protons with an optical property modifying reagent. Such a reaction sufficiently modifies an optical property of the optical property modifying reagent to allow detection of the modified optical property by an un-assisted human eye. In some versions, performing an optical property modification includes changing the pH of reaction chamber contents by performing a reaction. An optical property modifying reagent can produce a modification based on the location and extent of such a pH change.

In some versions, the methods include determining one or more characteristics of the sample based on the modified optical property. According to various embodiments, the methods include detecting a characteristic of the reaction product, wherein such detection can be performed by an un-assisted human eye. An un-assisted human eye refers to a human eye that is not enhanced by one or more devices which enhance or modify visual ability. Such devices might include a camera, optical magnifier, microscope, or optimized, e.g., filtered, e.g., polarized, glasses or contacts, etc. As such, detecting a characteristic of the reaction product can include visually inspecting the one or more reaction chambers to detect a modified optical property. Also, in some aspects, detecting a characteristic of the reaction product includes detecting presence or absence of a nucleic acid amplification.

In various aspects, determining one or more characteristics of the sample includes obtaining modified optical property image data with a sample analyzer. In some aspects, obtaining such image data includes taking one or more photo of a device component such as a sample receiving cartridge or portion thereof, e.g., reaction chamber. Also, in some aspects, determining one or more characteristics of the sample includes comparing the modified optical property image data with modified optical property image data stored in a database. Such a comparison can be performed automatically with a processor. The methods also can include storing the modified optical property image data, such as one or more photos and/or videos, in a database.

Also, in some versions, determining one or more characteristics of a sample includes performing optical property image analysis on image data, such as by comparing the image data with data stored in a library of image data and/or associated characteristics, to produce a biological assay result with the sample analyzer.

Also, according to various embodiments, determining one or more characteristics of a sample includes manually, e.g., visually, comparing an optical property change or lack thereof to one or more optical property references, e.g., colors, displayed on a card readout. The methods can also include providing and/or producing a card readout, e.g., a card readout on a portable hand-held printable medium, such as paper and/or plastic. The methods can include displaying one or more features, e.g., references colors and/or associated information, of a sample having the modified optical property on the card and identifying one or more characteristics of the sample based on the one or more displayed features.

In some aspects of the methods, a device includes a sensor and the methods include detecting the presence or absence of the sample in one or more reaction chambers with the sensor. Also, where a device includes a heating element, the methods can include heating a sample in the one or more reaction chambers when a sensor detects sample in the one or more reaction chambers. Heating a sample can be performed in any of the amounts which a heating element is configured to do so, as is described herein. Also, in some versions, the devices include a light and the methods include emitting light with the light source when the sensor detects the sample in the one or more reaction chambers.

In some embodiments, the methods include reacting a sample with the modifying reagent by contacting the sample with the nucleic acid amplification composition in the one or more reaction chambers under conditions that result in amplification of the nucleic acid, if present in the sample. As such, the methods can include performing an amplification of a nucleic acid.

In various embodiments, the methods also can include modifying an optical property in a biological sample assay. Such a modification can be performed on a biological sample, or an aspect associated therewith, such as a reaction mixture or a reaction product. Where desired, a modification of an optical property can be performed with an optical property modifying device, as such devices are described herein.

As provided in the subject disclosure, modifying an optical property refers to changing one or more optically-recognizable characteristics of an aspect, e.g., a sample, such as a characteristic resulting from wavelength and/or frequency of radiation, e.g., light, emitted from an aspect, such as color, fluorescence, phosphorescence, etc. For example, in some versions, the optical property is color and modifying the optical property includes changing the color. In some aspects, such an optical property modification, e.g., color change, is detectable by an un-assisted human eye under, for example ambient light, and the subject methods include making such detection with an un-assisted human eye. Modifying an optical property can also include changing the transmittance and/or opacity of a substance and can include causing the substance to change substantially from transparent to opaque or from opaque to transparent. As such, the methods can include detecting such a change with an un-assisted human eye.

In some aspects, the subject methods include exposing a reagent or substance as disclosed herein and/or a device or portion thereof, e.g., a sample receiving cartridge, to external, e.g., ambient, light to thereby measure the change in optical property. Such external light can include a camera flash or fluorescent excitation light. Exposure to external light can provide a change in conditions such that the optical property can be measured.

In some aspects, a heating element is operatively coupled to a substrate, e.g., a circuit board, such as a printed circuit board, of a device. As noted herein, a substrate can also include and/or be operatively coupled to one or more sensors and/or a control unit and/or a power source, and/or one or more light source. As such, in some versions, transmitting a biological sample into one or more reaction chambers includes detecting a sample, e.g., a liquid, in one or more reaction chambers with one or more sensors. The sensors can be, for example, electrochemical sensors. The sensors can be configured to send and/or receive electrical energy to and/or from one or more reaction chambers via, in some versions, an adhesive layer and/or one or more electrical contacts. Such sensors can be configured to detect the presence and/or absence of liquid in one or more reaction chambers. Also, in some variations wherein a substrate is operatively coupled to a light source, transmitting a biological sample into one or more reaction chambers can include activating the light source to emit light and/or deactivating the light source to stop emitting light. In some versions of the subject devices, the sensors, control unit and/or heating element are operatively connected such that when liquid enters a reaction chamber, the sensor senses the liquid and the heating element begins heating the reaction chamber automatically, such as without a particular user action required.

According to embodiments of the subject methods wherein a substrate includes a control unit, modifying an optical property of the biological sample can include performing an optical property, e.g., colorimetric, analysis of a sample in the one or more reaction chambers with the control unit and/or a sample analyzer. Such an analysis can be performed on a reaction product after reacting it with the optical property modifying reagent. Performing an optical property, e.g., colorimetric, analysis can include determining, based on an input, e.g., an input from one or more sensors, whether a change in an optical property, e.g., color, of one or more contents of a reaction chamber, has occurred. Based on the determination, performing the analysis can include generating an output, such as an output to a user via a display, wherein the output reflects to the user whether a modification has occurred. Performing an optical property, e.g., colorimetric, analysis can also be performed by a user without employing a control unit, such as by using an analyzing device or by making a determination based on a visual inspection. Furthermore, performing an optical property, e.g., colorimetric, analysis can also include obtaining image data, e.g., photo and/or video, of an optical property modification or lack thereof with, for example, a sample analyzer, e.g., a camera, such as a camera on a mobile phone, and evaluating the data visually or with a sample analyzer, such as a mobile phone.

In various aspects, the subject methods include transferring electrical energy from one or more elements of a substrate, e.g., a control unit and/or a sensor, to one or more reaction chambers via an adhesive layer. The methods can also include transferring electrical energy from one or more reaction chambers to one or more elements of a substrate, e.g., a control unit and/or a sensor, via an adhesive layer. In some aspects, performing an optical property modification analysis requires such electrical energy to be transmitted.

According to aspects of the methods, the sample receiving cartridge is transparent, and performing an optical property, e.g., colorimetric, analysis includes detecting, visualizing, one or more characteristics of light, e.g., color or opacity, transmitted through the sample receiving cartridge. In some aspects of the methods, an optical property modifying device also includes an adhesive layer, an opaque and/or white adhesive layer, operatively connected to the sample receiving cartridge. In such aspects, the methods can include performing an optical property analysis, such as by visually inspecting the chambers to detect a modified optical property, of the reaction product after reacting it with an optical property modifying reagent.

Embodiments of the subject devices can also be manufactured according to the subject methods by operatively coupling a sample receiving cartridge and/or a substrate with the adhesive layer. Such coupling can be performed by placing an adhesive layer against a sample receiving cartridge and/or a substrate and attaching, such as by adhesively binding and/or melting the components to one another. Specifically, in some embodiments, the methods include contacting an adhesive layer directly with a substrate, e.g., a printed circuit board, and binding, e.g., adhesively binding, or laminating the two together. In some aspects, an adhesive layer has a first side and a second side opposite the first side. As such, manufacturing a device by operatively coupling a sample receiving cartridge and substrate can include adhesively attaching the sample receiving cartridge to the first side and the substrate to the second side. Such manufacturing can be performed manually or automatically, such as with an electronic manufacturing device, such as a manufacturing device which can be programmed to perform one or more manufacturing steps.

According to some versions, the reaction chambers each include an amplification composition, e.g., a nucleic acid amplification composition. As noted above, one or more one or more reaction chambers of a device can each include an amplification composition, e.g., a nucleic acid amplification composition. As such, transmitting a biological sample into one or more reaction chambers can include mixing a biological sample with the one or more amplification composition. Such mixing can include causing a chemical reaction between the two.

In various instances, heating a reaction mixture with a heating element includes accelerating a nucleic acid amplification reaction between, for example, nucleic acids of a biological sample and one or more aspects of an amplification composition, e.g., a nucleic acid amplification composition. As such, in various aspects, the reaction generates one or more amplified nucleic acid. Such a reaction can also generate a reaction product. Such a reaction product can be or include a plurality of protons and/or one or more amplified nucleic acid.

According to some aspects, the subject methods also can include reacting the reaction product, or an aspect thereof, such as one or more protons and/or one or more amplified nucleic acid, with an optical property modifying reagent. Such reacting can be performed, for example, by placing the reaction product, or an aspect thereof, such as one or more protons and/or one or more amplified nucleic acid, in contact with an optical property modifying reagent, such as by mixing them in one or more container, e.g., one or more reaction chambers. Reacting the reaction product, or an aspect thereof, with an optical property modifying reagent can include chemically modifying the reaction product and/or the optical property modifying reagent, such as by bonding the one or more protons to the optical property modifying reagent, so that one or the other displays one or more different optical property, such as a color and/or opacity.

In addition, reacting the reaction product, or an aspect thereof, such as one or more protons and/or one or more amplified nucleic acid, with an optical property modifying reagent, in various embodiments, sufficiently modifies an optical property, e.g., color and/or opacity, of the optical property modifying reagent to allow detection of the modified optical property by an un-assisted human eye.

An embodiment of the subject methods can be illustrated in association with the device 1800 as shown in FIGS. 18 and 19. Accordingly, in some aspects, the methods include introducing a biological sample into an optical property modifying device 1800 by flowing the sample into one or more reaction chambers 1802 of a sample receiving cartridge of the device via an inlet 1810 an/or one or more sample receiving openings 1812. In some aspects, flowing the sample into the one or more reaction chambers 1802 includes flowing a gas, such as air, through a selective venting element 1807 of the device, wherein the selective venting element forms a wall of each of the one or more reaction chambers 1802, and wherein the one or more reaction chambers each include a modifying reagent 1901. The methods can also include contacting the sample liquid with the selective venting element 1807 and thereby making the selective venting element 1807 impermeable to fluid.

Once a selective venting element is made impermeable to fluid, the methods include preventing further flow of fluid though a device. As such, after such flow is stopped, diffusion is the only method for transporting any contaminants in and/or out of the reaction chamber. Therefore if the inlet and/or conduits have a sufficient length, the contaminant diffusion time is substantially longer than the reaction and/or readout time and a result is not affected by contaminants.

In addition, in some versions of the methods, a device is manufactured by encapsulating within a housing a selective venting element, sample receiving cartridge, adhesive layer, and/or substrate, or any combination thereof, by contacting them together in a single concerted step. In some variations, the methods do not include manufacturing a device for example, by performing a first step of patterning a substrate layer, such as a glass, silicon and/or polymer layer, and/or binding a patterned, e.g., binding it chemically and/or physically, to a non-patterned layer, e.g., a sealing layer, and a second subsequent step of integrating the bound and/or sealed layer into a housing or cassette that provides additional functionality to employ the fluidic device. Also, in various embodiments, the methods of manufacturing the subject devices include substantially preserving the functionality, e.g., chemical functionality, of reaction chamber contents, such as optical property modifying reagents and/or amplification compositions, while the contents are contained in the reaction chambers during manufacturing. This is achieved as the manufacturing process does not expose reagents to extreme temperature or chemical environments. Also, in some versions of the methods, the methods include manufacturing a device by operatively coupling an adhesive layer and a substrate while reaction chamber contents, such as optical property modifying reagents and/or amplification compositions, are retained within the reaction chambers. In some versions, operatively coupling an adhesive layer and a substrate does not include heating the adhesive layer, substrate, or environment surrounding either. In some versions, the methods include a step of inserting the optical property modifying reagent into each the one or more reaction chambers and storing the optical property modifying reagent therein while retaining functionality of the optical property modifying reagent.

The methods also include using a sample analyzer to analyze one or more optical property modification or lack thereof. According to some versions, a user downloads the sample analyzer application, which can be a computer program, to the sample analyzer. A QR code on the outside of the sample analyzer or packaging thereof can provide a direct link to download the application or the application can be found by a user in a database of applications for mobile devices.

According to the subject methods, the user can then execute the application using the sample analyzer by making one or more inputs therein. The application in turn can instruct the user to scan the code, e.g., QR code, on the device package. An initial screen then appears on the display of the sample analyzer providing information on the analysis, necessary materials and test environment, and/or precautions. A menu will also appear on the screen which the users can navigate according to the subject methods to find information, e.g., contact information, should they have questions about device use or need assistance in use. One a user has read the information, a user can initiate a sample analysis by making such an indication by providing an input to the sample analyzer.

The application then provides information which instructs the user through the process of collecting a sample as described herein and/or setting up the optical property modifying device and/or sample analyzer for performing an assay. Each step of the information can include pictures, diagrams and/or videos displayed on a display of the sample analyzer as appropriate. The devices can also include a guide on a printed medium providing the same instructions.

Information which instructs the user through the process of performing an assay as provided by the application can include a first instruction wherein a user removes the sample preparation module and optical property modifying device from their respective packages e.g., foil pouches.

In a second step, the application instructs the user to remove a swab from its sterile packaging and collects the sample. In a professional setting, this can be done by the patient or by a clinician. In the case of a self-collected patient sample, the patient can place the swab into a protective vial for transport to a healthcare provider.

In a third step, the application can instruct the user to remove a foil seal on the top of the sample preparation device and insert a swab; swirl the swab around for 10-20 seconds; and/or snap the swab at a molded breakpoint and then caps the device. Such an action initiates the lysis process.

In a fourth step, the application can instruct the user to place the sample preparation device onto the optical property modifying device. The optical property modifying device can detect this event and begin flashing a green LED indicating that sample preparation is underway. The user can then be instructed to wait until they hear a beep and the LED turns steady green. Such a process can take 10 minutes or less, such as 5 minutes or less, such as 1 minute or less.

In a fifth step, the application can instruct the user to rotate the sample preparation device, e.g., rotate clockwise, such as rotate 90 degrees. Such an action can cause sample lysate to enter the optical property modifying device and/or cause the heater on the device to activate. Again, the LED flashes green indicating that detection is underway. The user is then instructed to wait until they hear a beep and the LED turns steady green again. Such a process can take 5 minutes or less, 10 minutes or less, 20 minutes or less, 30 minutes or less, or 1 hour or less.

In a fifth step, the application can instruct the user to align the optical property modifying device with a sample analyzer or a portion thereof, e.g., an on-screen guide, and obtain an image. Onboard image processing executes an algorithm and thereby determines which markers are positive and negative based on color and/or displays the results and treatment options, if necessary, to the user. In at-home settings, results can be displayed only after review by a physician.

In various embodiments, the optical property modifying device and/or sample analyzer can be employed at a healthcare facility by, for example a healthcare professional, to perform tests and provide results to a patient in a short time-frame, such as 3 hours or less, such as 2 hours or less, such as 1 hour or less, such as 30 minutes or less. In such a circumstance, the subject devices can be employed as one protocol in a visit by the patient to a healthcare facility.

In some aspects, a sample analyzer can convey information, e.g., data and/or prescription instructions, between a user and a healthcare professional, e.g., a doctor, nurse, physician's assistant, pharmacist, etc., and/or a remote central processing unit. For example, a prescription for medication can be sent to the sample analyzer by a healthcare professional and employed by the user of the sample analyzer to obtain medication or other treatment. Such a prescription can be based, for example, on one or more analysis results provided by the sample analyzer. In another embodiment, a prescription for medication can be sent to the sample analyzer by a remote central processing unit automatically based on one or more analysis results provided to it by the sample analyzer. Whether such a prescription is sent can be based on instructions executed by the remote central processing unit, wherein the instructions are set by a healthcare professional.

In some versions, assays performed by the subject devices can be combined with, such as performed simultaneously with, one or more drug treatments, such as drug treatments designated by healthcare professionals. In such combinations, the assays performed by the subject devices can be employed to evaluate the effectiveness of the one or more drug treatments and/or employed to evaluate when and/or how the drug treatments should be modified.

In some aspects, applying the optical property modifying device and/or sample analyzer can include performing geolocalization of produced data and/or results. As such, in some versions, results from a plurality of subject devices can be assimilated, compared and/or analyzed based on geographic location. In such embodiments, the produced data and/or results include location information indicating the geographic location where the results were obtained. Performing geolocalization of produced data and/or results can be performed automatically by a processor, such as a processor of an analyzing device or manually by a person and can produce a geolocalization result which includes information about a plurality of device results, such as device results compared with another's type and/or location. A geolocalization result can in turn be applied according to the subject methods to predict and/or prevent disease spread in a particular location.

The subject methods can also include performing anonymous data collection, such as data collection of disease spread, based on data and/or results produced by the optical property modifying device and/or sample analyzer. Such data collection can be performed automatically by a processor, such as a processor of an analyzing device or manually by a person. For example, one or a plurality of subject devices can be configured to communicate anonymous information regarding one or more disease to a central processing unit which, in turn, analyzes the information and produces a result analyzing and/or predicting one or more aspects of disease spread.

The amplification reaction amplifies nucleotides from a nucleic acid template. In some embodiments, the amplification reaction is an isothermal amplification reaction, such as a strand displacement reaction. In a further embodiment, a strand displacement reaction is provided by a polymerase with strand displacement activity under reaction conditions such that strand displacement is possible. Examples of strand displacement reactions include strand displacement amplification (SDA), multiple displacement amplification (MDA), rolling circle amplification (RCA) or loop mediated isothermal amplification (LAMP). In other embodiments, the amplification reaction includes other non-isothermal amplification reactions such as polymerase chain reaction (PCR).

In certain embodiments, the amplification reaction performed is LAMP. In a LAMP reaction, a double- or single-stranded nucleic acid, e.g., DNA and/or RNA, template in dynamic equilibrium at an elevated temperature is amplified using two or three pairs of primers. The primers are designed based on the DNA and/or RNA template, using primer design software such as LAMP Designer (Premier Biosoft, Palo Alto, CA). In the first step of the LAMP reaction, the F2 region of the FIP (Forward Inner Primer) anneals to the single stranded DNA at the respective complementary (F2c) position. Next, a polymerase with strand displacement activity incorporates dNTPs along the template from the 3' end of F2. The incorporation of nucleotides releases protons, reducing the pH of the reaction mix. Then, the F3 forward primer anneals to the F3c region upstream of the F2 region and on the template. The F3 forward primer begins amplifying the template strand, which releases further protons and displaces the FIP-incorporated strand that was synthesized previously. This single strand contains an F1 sequence (within the target sequence) along with its complementary F1c sequence (within the FIP). This forms a stem-loop as F1c anneals to F1 at the 5' end. At the same time, the BIP (Backward Inner Primer) anneals to the other end of the strand and nucleotides extend from B2, releasing more protons. The backward primer B3 then binds to the B3c region, downstream of the B2 region, displaces the BIP-amplified strands and promotes extension to create the double strand. This displaced strand now contains a B1 sequence (within the target sequence) along with its complementary B1c sequence (within the BIP), forming another stem loop in the 3' end. The structure now has two stem-loop structures at each end from which continuous displacement and extension occur to amplify the template. The LAMP reaction can be amplified by adding further Forward and Backward Loop primers to produce more amplicons with stem loop structures.

The LAMP procedure can take place at a fixed temperature, minimizing the need for any expensive thermocycling equipments. Typically, isothermal methods require a set temperature, which is determined by the selected reagents. For example, enzymes function best between 60-65° C. in LAMP methods.

Colorimetric detection of the nucleic acid amplification reaction product can be performed in real-time throughout the amplification reaction, or after the performance of the amplification reaction. Detection of the colorimetric change of the reaction mix can be associated with a digital indication of a presence or absence of the amplification reaction product. In other words, a visual observation of the color change of the reaction mix can provide information regarding whether the amplification reaction product is present or absent. In certain embodiments, detection of a colorimetric change of the reaction mix indicates that the exponential or plateau phase of the amplification reaction has been obtained.

In some embodiments, detection of the amplification reaction product is accelerated relative to an amplification reaction that uses a reaction mix without a halochromic agent. In further embodiments, the colorimetric change of the reaction mix is detected in less than 60 minutes from a starting time of the amplification reaction. Accelerated detection of the amplification reaction product is obtained because the halochromic agent (a weak acid or base) in the reaction mix absorbs protons generated during the amplification reaction, and recombination of the free protons acts to accelerate the detection of the amplification reaction. The reaction can be designed so that minimal amplification is required to generate a pH transition sufficient for the halochromic agent to change color. Conventional amplification techniques that use fluorescent intercalating dyes, molecular beacons, hybridization probes, dye-based detection, UV-Vis, or other detection methods require a certain threshold amount of amplification to occur before an amplification signal is detectable. However, the methods of the present invention require a relatively smaller threshold amount of amplification before a color change of the halochromic agent is detectable, and therefore the detection of an amplification reaction product is accelerated relative to conventional amplification methods.

In some embodiments, the amplification reaction product is detected visually by observation of a color change of the reaction mix. In a further embodiment, the human eye is used for the visual detection. In another embodiment, a camera, a computer, or some other optical device is used for the visual detection or for imaging the reaction mix. Imaging programs include Photoshop (Adobe, San Jose CA), ImageJ (National Institutes of Health, Bethesda MD), and MATLAB (MathWorks, Natick MA). In another embodiment, the amplification reaction product is detected by measuring fluorescence of the reaction mix, using fluorescence spectroscopy methods. In another embodiment, the amplification reaction product is detected by measuring absorbance of the reaction mix, using absorption spectroscopy methods. In a further embodiment, the endpoint or overall change in absorbance or fluorescence of the reaction mix is measured at a given wavelength or set of wavelengths.

FIG. 34 provides nucleic acid amplification reaction times across six different reaction chambers in an optical property modifying device according to embodiments of the subject disclosure. Columns represent reaction chamber positions and rows represent different devices. An integrated heating and fluidic cartridge provides uniform heating, allowing uniform multiplexed reaction conditions. As such, in this embodiment, the optical property modifying device includes an integrated heating element. The assay associated with the data presented in FIG. 34 is a LAMP control assay similar to the lambda DNA assay described herein.

In addition, FIG. 35 provides color changes, as measured using the CIE94 Delta-E scale, resulting from nucleic acid amplification reactions across six different reaction chambers in an optical property modifying device according to embodiments of the subject disclosure. As provided in FIG. 35, columns represent reaction chamber positions and rows represent different devices. An integrated heating and fluidic cartridge provides uniform heating, allowing uniform multiplexed reaction conditions. As such, in this embodiment, the optical property modifying device includes an integrated heating element. The applied device also includes an adhesive layer. The adhesive layer interposed between the fluidic channels and heater substrate provides thermal conduction as well as a uniform white background for reading color. The assay associated with the data presented in FIG. 35 is a LAMP control assay similar to the lambda DNA assay described herein. This device architecture represents a low-cost solution for visually reading multiplexed nucleic acid amplification assays.

Figure 36:
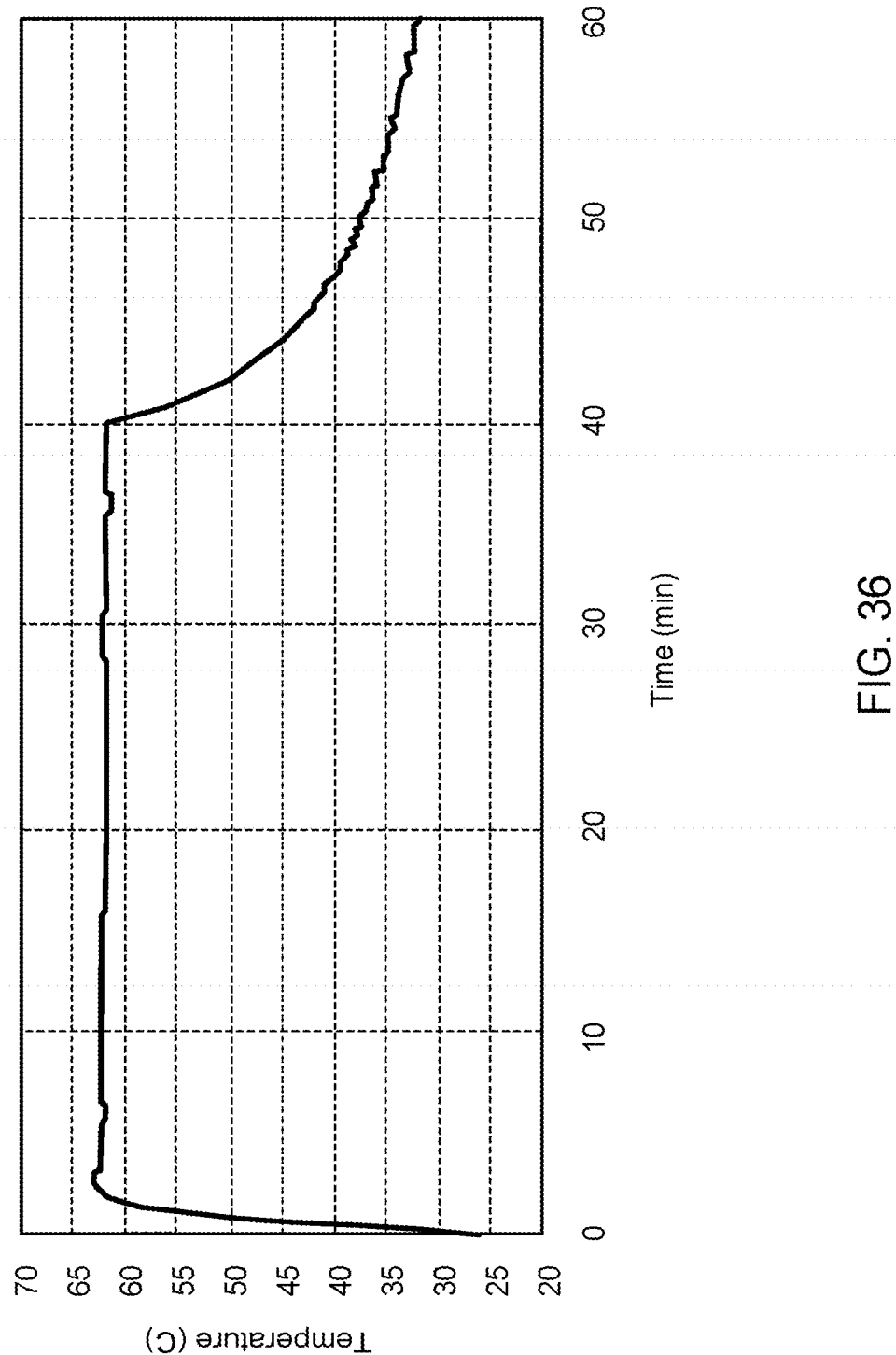
FIG. 36 provides a temperature profile of a reaction chamber, e.g., fluidic reservoir, operatively coupled to a heating element in the described manner according to embodiments of the subject disclosure.
Figure 37:
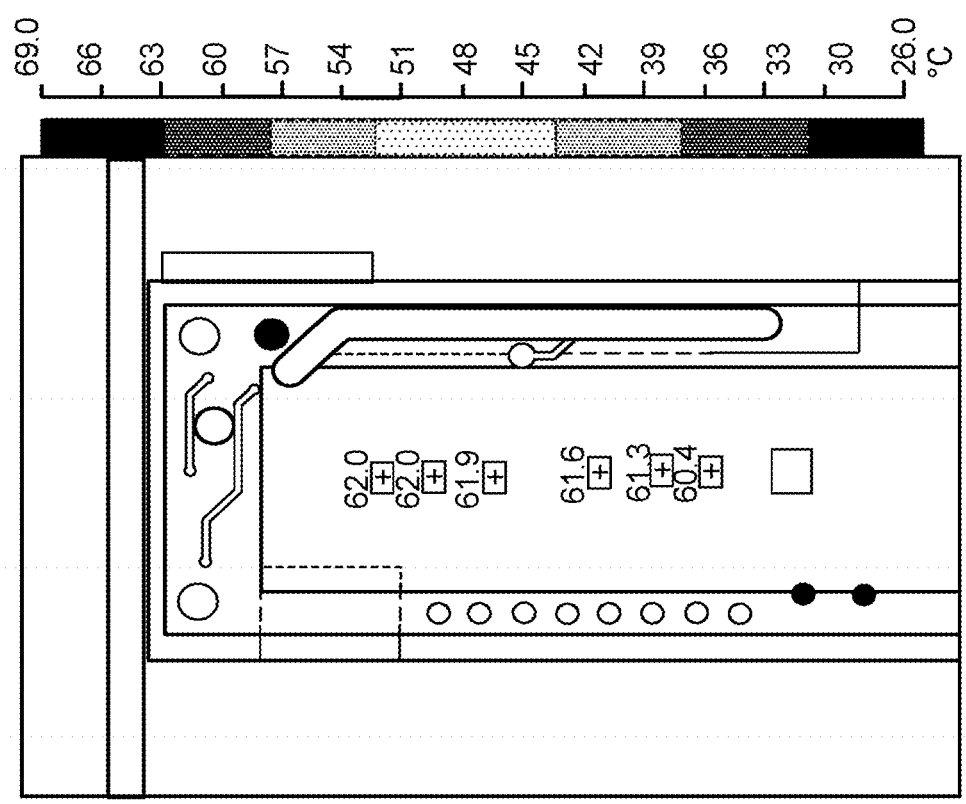
FIG. 37 provides temperature uniformity across six heating locations on a heating element, e.g., an electronic heater board, for operatively coupling with a multiplexed nucleic acid amplification assay according to embodiments of the subject disclosure.

Furthermore, FIG. 36 provides a temperature profile of a reaction chamber, e.g., fluidic reservoir, operatively coupled and/or adjacent to a heating element, e.g., an electronic heater, in the described manner. In addition, FIG. 37 provides a depiction of temperature uniformity across six heating locations on a heating element, e.g., an electronic heater board, for operatively coupling with a multiplexed nucleic acid amplification assay. In such an embodiment, the assay includes an optical property modifying device including reaction chambers according to embodiments of the subject disclosure.

Compositions

Disclosed herein are compositions and methods for accelerated and efficient colorimetric detection of nucleic acid amplification reaction products. In an embodiment, a colorimetric assay is used to visually detect the presence of an amplified nucleic acid product, which eliminates the need for expensive and sophisticated instrumentation.

In some embodiments, the colorimetric detection of amplification products is achieved by amplifying a target nucleic acid template molecule to obtain the amplification reaction product. The amplification reaction includes a reaction mix. In an embodiment, the reaction mix includes a nucleic acid template molecule, one or more enzymes for catalyzing the amplification reaction, and one or more halochromic agents for colorimetric detection. In a further embodiment, the reaction mix also includes a buffer having a buffering capacity equivalent to Tris buffer at a concentration between 1 mM-19 mM in a solution having a starting pH of 8.0. In further embodiments, the reaction mix also includes a plurality of nucleic acid primers, deoxynucleotide triphosphates (dNTPs), suitable salts for the enzyme, and other non-buffered chemicals that enable nucleic acid amplification.

During the amplification reaction, one proton is released for each dNTP that is incorporated into a nucleic acid template molecule. Thus, the pH of the reaction mix decreases throughout the amplification reaction. In an embodiment, if the target nucleic acid is present, the amplification reaction changes the starting pH of the reaction mix to cause a detectable colorimetric change of the halochromic agent, thereby indicating the presence of the target nucleic acid, and if the target nucleic acid is not present, the amplification reaction does not generate a sufficient number of protons to change the starting pH of the reaction mix sufficient to cause a detectable colorimetric change of the halochromic agent, thereby indicating that the amplification reaction product has not been produced. In an embodiment, the halochromic agent (or pH indicator) in the reaction mix has a transition pH range for a colorimetric change of the halochromic agent that is narrower than an expected pH change between (1) a starting pH of the reaction mix before the amplification reaction is performed, and (2) an ending pH of the reaction mix after the amplification reaction has been performed.

In an embodiment, the halochromic agent is a colorimetric agent or a fluorescent agent. Suitable halochromic agents include phenol red, bromocresol purple, bromothymol blue, neutral red, naphtholphthalein, cresol red, cresolphthalein, phenolphthalein, methyl red, and thymolphthalein, among others. A wide range of concentrations of these halochromic agents can be used in the reaction mix. Different halochromic agents have different transition pH ranges. In some embodiments, the halochromic agent has a transition pH range between pH 5-10, between pH 6-9, or between pH 6.5-8.8. In another embodiment, the halochromic agent is at a concentration between 25-100 µM in the reaction mix. In another embodiment, the halochromic agent is at a concentration between 50-260 µM. In some embodiments, a combination of two or more halochromic agents is used in the reaction mix, which increases the normalized color contrast change of the reaction mix by being of complementary colors at the beginning and similar colors at the end of the amplification reaction. In a further embodiment, the combination of halochromic agents comprises phenol red and bromothymol blue. In a further embodiment, the combination of halochromic agents comprises cresol red and bromothymol blue.

In one example, Phenol red is a halochromic agent that has a transition pH range from around 6.4-8.0. At the upper limit of the transition pH range, phenol red is red, and at the lower limit of the transition pH range, phenol red is yellow. A reaction mix containing phenol red will change color from red to yellow throughout the amplification reaction, as long as the starting pH of the reaction mix is around or above 8.0, and the ending pH of the reaction mix is within the transition pH range or around or below 6.4.

In some embodiments, the starting pH of the reaction mix is set by adding an acid or a base to the reaction mix until the desired starting pH is reached. The ending pH of the reaction mix is determined by performing a sample amplification reaction and measuring the ending pH (for example, with a micro-pH electrode). In an embodiment, the halochromic agent for an amplification reaction is selected so that the transition pH range lies in between the starting pH and ending pH. In a further embodiment, the halochromic agent is selected so that the transition pH range is nearer to the starting pH than the ending pH. The halochromic agent can also be selected based on the particular enzyme used for catalyzing the amplification reaction. Near the ending pH, the enzyme in the reaction mix terminates polymerization of the amplification reaction as the pH decreases to unfavorable H$^+$ concentrations. In an embodiment, additional hydronium ions or hydronium ion equivalents are added to the reaction mix via the sample. For example, between $4.8 \times 10^{-9}$ and $4.8 \times 10^{-18}$ additional hydronium ion equivalents per 10 µl reaction mix can be tolerated for the amplification reaction to proceed. In a further embodiment, between $4.8 \times 10^{-10}$ and $4.8 \times 10^{-18}$, $4.8 \times 10^{-12}$ and $4.8 \times 10^{-18}$, or $4.8 \times 10^{-15}$ and $4.8 \times 10^{-18}$ can be tolerated.

Generally, the enzyme will catalyze amplification reactions within a pH range that encompasses or is close to the transition pH range of the selected halochromic agent. Various enzymes can be used for the reaction, and different enzymes catalyze amplification reactions at different pH ranges. For example, Bst polymerase is believed to catalyze amplification reactions within the pH range of 6.6-9.0. The preferred starting pH for Bst polymerase is greater than 7, more preferably greater than 8.2, and more preferably at 8.8. Other examples of a preferred starting pH for Bst polymerase are found in U.S. Pat. No. 5,830,714, filed Apr. 17, 1996, hereby incorporated by reference in its entirety. In an embodiment, phenol red is coupled with Bst polymerase in a reaction mix, since the pH range at which Bst polymerase is active (6.6-9.0) encompasses the transition pH range of phenol red (6.4-8.0). In another embodiment, methyl red is coupled with U exo-Klenow fragment (polymerase for Helicase Dependent Amplification, HDA) in a reaction mix, since a starting pH at which U exo-Klenow fragment is active (around 7.5) is higher than the transition pH range of methyl red (4.8-6.2).

Other than Bst or Bst 2.0 polymerase, other enzymes capable of being used for catalyzing the amplification reaction include the polymerase from *Thermus aquaticus* (TAQ), DNA polymerases I-IV, Kapa Polymerase, RNA polymerases I-V, T7 RNA Polymerase, a reverse transcriptase, any DNA polymerase or RNA polymerase, a helicase, a recombinase, a ligase, a restriction endonuclease, and a single-strand binding protein. In some embodiments, an isothermal amplification reaction uses an enzyme that is a strand displacement polymerase, such as phi29-DNA-Polymerase, Klenow DNA-Polymerase, Vent DNA Polymerase, Deep Vent DNA Polymerase, Bst DNA Polymerase, 90 Nm™ DNA Polymerase, U exo-Klenow fragment, or mutants and variants thereof. In some embodiments, suitable salts for the enzyme are also added to the reaction mix. In certain embodiments, the starting pH of the reaction mix is set based on an optimal pH for the specific enzyme used for catalyzing the amplification reaction. In an embodiment, the pH of the entire DNA sample is between pH 3 and pH 11.

In other embodiments, a fluorescent halochromic agent is used to detect protons released during amplification. The halochromic agent can change optical properties (such as amplitude and emitted wavelength) as the pH of the reaction mix changes during the amplification reaction. Fluorescent halochromic agents include fluorescein, pyranine, and pHrodo dye (Life Technologies, Carlsbad CA).

The base and/or acid added to the reaction mix maintains the starting pH of the reaction mix around or above an upper limit of the transition pH range of the halochromic agent. For example, an acid such as hydrochloric acid (HCl) or sulfuric acid ($H_2SO_4$), or a base such as sodium hydroxide (NaOH) or potassium hydroxide (KOH), can be added to the reaction mix. In some embodiments, the acid or base sets the starting pH of the reaction mix between pH 6-10, between pH 7-8, or between pH 8-8.6. In an embodiment, the reaction mix is capable of offsetting the starting pH of the reaction mix by less than 0.1 pH units. In another embodiment, the reaction mix has a starting pH lower than 2 pH units above the upper limit of the transition pH range of the halochromic agent. In further embodiments, the reaction mix has a starting pH lower than 1 pH unit, 0.5 pH units, or 0.1 pH units above the upper limit of the transition pH range of the halochromic agent. In a further embodiment, noise from non-specific amplification is minimized by setting the pH transition range sufficiently separated from the starting pH of the reaction mix, so that any color change is only achieved by a specific and sustained amplification.

In an embodiment, the reaction mix does not require any additional buffering agent for the amplification reaction, since a buffering agent could prevent large changes in pH from occurring during the amplification reaction. In another embodiment, the reaction mix contains a minimal amount of buffering agent, such that the buffering capacity of the reaction mixture is less than the expected change in pH during amplification. In some embodiments, the buffer is at a concentration between 1 mM and 3 mM. In a further embodiment, the buffer is at a concentration of 1 mM. In certain embodiments, the buffer used is Tris buffer (formulated to pH 8.8), HEPES (pH 7-9), or TAPS (pH 7-9). In another embodiment, the buffer used is a buffer having a buffering capacity equivalent to a Tris buffer at a concentration between 1 mM-19 mM in a solution having a starting pH of 8.0. This broad range of suitable buffer concentrations allows the reaction mix to resist unwanted starting pH changes during reaction setup, unlike reaction setups with minimal (<1 mM) Tris buffer equivalents (see U.S. Ser. No. 13/799,995, filed Mar. 13, 2013). These unwanted changes in pH come about due to hydronium or hydroxide ion equivalents added to the reaction via the sample reagents. As colorimetric detection and enzyme kinetics depend on the starting pH, the presence of buffer capacity in the reaction mix high enough to avoid starting pH change, but low enough to allow color change upon amplification, become important. In a further embodiment, the pH of the reaction mix is between pH 7.5-8.8. Table 1 shows various buffers having buffering capacities equivalent to a Tris buffer at a concentration between 1 mM-19 mM in a solution having a starting pH of 8.0. The buffer capacity ($\beta$) is defined as the equivalents of acid or base needed to change the pH of 1 Liter of buffer by 1 pH unit. This can be calculated as: $\beta=2.3*C*(K_a*[H_3O^+]/(K_a+[H_3O^+])^2)$; where C is the buffer concentration, $K_a$ is the dissociation constant for the buffer and $[H_3O]$ is the hydronium ion concentration of the buffer (which is calculated from the reaction starting pH). The buffer capacity of 1 mM-19 mM Tris (in a solution having a starting pH of 8.0) was found to range from 0.000575 to 0.010873. The starting pH of the buffer was considered to be in the range of 7.5-8.8 to be compatible with the reaction biochemistry (polymerase function, nucleic acid melting, etc.). In other embodiments, the buffer has a buffering capacity equivalent to a Tris buffer at a concentration between 1.5 mM-19 mM, 2 mM-19 mM, 3 mM-19 mM, 4 mM-19 mM, 5 mM-19 mM, 6 mM-19 mM, 7 mM-19 mM, or otherwise, in a solution having a starting pH of 8.0. In other embodiments, the buffer has a buffering capacity equivalent to a Tris buffer at a concentration between 1.92 mM-36.29 mM, 3 mM-36.29 mM, 4 mM-36.29 mM, 5 mM-36.29 mM, or otherwise, in a solution having a starting pH of 8.8. In other embodiments, the buffer has a buffering capacity equivalent to a Tris buffer at a concentration between 1.48 mM-27.92 mM, 2 mM-27.92 mM, 3 mM-27.92 mM, 4 mM-27.92 mM, 5 mM-27.92 mM, or otherwise, in a solution having a starting pH of 7.5.

TABLE 1

Buffer Capacity Table

| Buffer | Full Chemical Name | pKa at 25° C. | Starting Reaction pH | Min Conc (mM) | Max Conc (mM) |
|---|---|---|---|---|---|
| Tris | tris(hydroxymethyl) methylamine | 8.06 | 8.8 | 1.92 | 36.29 |
|  |  |  | 8.0 | 1.00 | 19.00 |
|  |  |  | 7.5 | 1.48 | 27.92 |
| TAPS | N-Tris(hydroxymethyl) methyl-3-aminopropanesulfonic acid | 8.43 | 8.8 | 1.19 | 22.55 |
|  |  |  | 8.0 | 1.27 | 23.94 |
|  |  |  | 7.5 | 2.66 | 50.25 |
| Bicine | N,N-bis(2-hydroxyethyl) glycine | 8.35 | 8.8 | 1.29 | 24.46 |
|  |  |  | 8.0 | 1.17 | 22.15 |
|  |  |  | 7.5 | 2.31 | 43.59 |
| Tricine | N-tris(hydroxymethyl) methylglycine | 8.15 | 8.8 | 1.67 | 31.63 |
|  |  |  | 8.0 | 1.03 | 19.48 |
|  |  |  | 7.5 | 1.67 | 31.63 |
| TAPSO | 3-[N-Tris (hydroxymethyl) methylamino]-2-hydroxypropanesulfonic acid | 7.635 | 8.8 | 4.17 | 78.90 |
|  |  |  | 8.0 | 1.19 | 22.45 |
|  |  |  | 7.5 | 1.02 | 19.37 |
| HEPES | 4-(2-hydroxyethyl)-1-piperazineethanesulfonic acid | 7.48 | 8.8 | 5.74 | 108.45 |
|  |  |  | 8.0 | 1.40 | 26.54 |
|  |  |  | 7.5 | 1.00 | 18.92 |

TABLE 1-continued

Buffer Capacity Table

| Buffer | Full Chemical Name | pKa at 25° C. | Starting Reaction pH | Min Conc (mM) | Max Conc (mM) |
|---|---|---|---|---|---|
| TES | N-tris(hydroxymethyl)methyl-2-aminoethanesulfonic acid | 7.4 | 8.8 | 6.79 | 128.39 |
| | | | 8.0 | 1.56 | 29.46 |
| | | | 7.5 | 1.01 | 19.16 |
| MOPS | 3-(N-morpholino)propanesulfonic acid | 7.2 | 8.8 | 10.46 | 197.77 |
| | | | 8.0 | 2.12 | 40.03 |
| | | | 7.5 | 1.12 | 21.26 |
| PIPES | 1,4-piperazinediethanesulfonic acid acid | 6.76 | 8.8 | 27.91 | 500.00 |
| | | | 8.0 | 4.86 | 91.88 |
| | | | 7.5 | 1.92 | 36.29 |
| SSC | Saline Sodium Citrate | 7.0 | 8.8 | 16.28 | 300.00 |
| | | | 8.0 | 3.03 | 57.20 |
| | | | 7.5 | 1.37 | 25.90 |

In an embodiment, a magnesium compound is added to the reaction mix, because magnesium promotes nucleotide incorporation into the template and influences the activity of the polymerase. In a further embodiment, the concentration of a magnesium compound (such as magnesium sulfate) in the reaction mix is at least 0.5 mM, at least 1 mM, at least 2 mM, or at least 4 mM. In an embodiment, the concentration of added magnesium ion is dependent on the concentration of dNTPs, nucleic acid template, and primers. In an embodiment, the ratio of dNTPs to magnesium sulphate in the reaction mix is less than 1:2, less than 1:3, less than 1:4 or less than 1:5.

In some embodiments, monovalent cations are added to the reaction mix. Monovalent cations include potassium, ammonium, and quaternary ammonium, among others. Monovalent cations can affect the melting characteristics of the nucleic acid template and improve the efficiency of the enzyme. In an embodiment, potassium is in the reaction mix at a concentration of less than 50 mM, or less than 15 mM. In another embodiment, quaternary ammonium salts are in the reaction mix at a concentration of greater than 2 mM, greater than 5 mM, or greater than 8 mM. In another embodiment, an ammonium compound (such as ammonium chloride) is in the reaction mix at a concentration of less than 15 mM, or less than 10 mM. Ammonium ($NH_4^+$) has some buffering capability, thus the final concentration of ammonium compounds in the reaction mix should be minimized while maintaining optimal amplification yield.

In an embodiment, the concentrations of other reagents of the reaction mix are kept at amounts as generally used in amplification reactions. See Notomi T et. al. Nucleic Acids Res. 2000 Jun. 15; 28(12): E63; Nature Protocols 2008, Loop-mediated isothermal amplification (LAMP) of gene sequences and simple visual detection of products, 2008 3(5): pg 880, hereby incorporated by reference in its entirety. In an embodiment, the Bst or Bst 2.0 enzyme is used, and the amount of enzyme is at least 0.8 Unit per microliter of combined fluid. In this embodiment, Betaine is also present in the reaction mix at a concentration between 0-1.5 M or 0.8M-1 M, and the total concentration of primers is between 3.6 µM and 6.2 µM. In some embodiments, any of the following reagents is present in the reaction mix: Tris buffer (pH 8.8) at 20 mM, KCl at 10 mM, $MgSO_4$ at 8 mM, $(NH_4)_2SO_4$ at 10 mM, TWEEN® 20 at 0.1%, Betaine at 0.8 M, dNTPs at 1.4 mM each, MnCl2 at 0.5 mM, FIP at 1.6 µM, F3 at 0.2 µM, B3 at 0.2 µM, primers at a total concentration of 5.2 µM (2*(1.6+0.8+0.2), and Bst/Bst 2.0 at 8 U per 10 µL.

The above reagent concentrations have been found to provide good amplification yield and low buffering capacity so that a halochromic pH sensor can be used to detect protons released during the amplification reaction. In some embodiments, the concentrations of reaction mix reagents depend on the enzyme selection. In further embodiments, guidance regarding appropriate reagent concentrations is available from the enzyme manufacturers. In an embodiment, the ratio of the sample volume to the reaction mix volume is such that the sample is diluted between 5% and 40% when the reaction mix is added.

In some embodiments, amplification reaction reagents are stored separately before being added to a reaction mix, since some reagents have specific required conditions for stability. For example, the enzyme can be stored long term in a moderately buffered solution separate from the other reagents to ensure stability of the enzyme. Upon mixing with the remaining reagents in the reaction mix, the buffering agent becomes sufficiently diluted so as not to significantly mask a pH change. In addition, primers for specific genes of interest can be provided in a separate solution or in a lyophilized form.

In some embodiments, the amplification reaction is performed within a microtube. In other embodiments, the amplification reaction is performed within a fluidic or microfluidic structure. In some embodiments, the fluidic or microfluidic structure is a well, chamber, or channel that receives the reagents and the nucleic acid sample separately, and then mixes the components together. In another embodiment, the fluidic or microfluidic structure is a well, chamber, or channel that receives the pre-mixed reaction mix. In a further embodiment, the fluidic or microfluidic structure possesses a long optical path for colorimetric observation, or a fluorescent/absorbance excitation source and detector. In another embodiment, the fluidic or microfluidic structure receives the reagents in a lyophilized form, and subsequently receives the nucleic acid sample and hydration solution. In an embodiment, a chamber fluidic or microfluidic structure has a channel depth ranging between 50 µm-400 µm or greater. In a further embodiment, colorimetric observation is accomplished for channel depths (path length) of 50 µm, 50 µm-400 µm, or 50 µm or greater.

Some embodiments include a kit for colorimetric detection of an amplification product. The kit can include one or more halochromic agents, one or more enzymes for catalyzing an amplification reaction, and instructions for contacting a sample with a reaction mix including the buffer and the enzyme and the halochromic agent under conditions that an amplification reaction occurs and produces an amplification reaction product if the sample contains a target nucleic acid template molecule, the reaction mix having a starting pH, and if the target nucleic acid template molecule is present, the amplification reaction changes the starting pH of the reaction mix to cause a detectable colorimetric change of the halochromic agent, thereby indicating the presence of the target nucleic acid, and if the target nucleic acid template molecule is not present, the amplification reaction does not generate a sufficient number of protons to change the starting pH of the reaction mix sufficient to cause a detectable colorimetric change of the halochromic agent, thereby indicating that the amplification reaction product has not been produced. In another embodiment, the instructions are for contacting a nucleic acid template molecule with the halochromic agent and enzyme in a reaction mix, under conditions that result in (1) an amplification reaction that amplifies the nucleic acid template molecule to produce an amplification reaction product, and (2) generation of a sufficient number of protons so that an ending pH of the reaction mix is sufficiently low to produce a detectable colorimetric change of the halochromic agent, thereby indicating that the amplification reaction product has been produced. In further embodiments, the kit also includes an acid or base, dNTPs, primers, and monovalent cations. In a further embodiment, the kit includes the following reagents at the following concentrations:

Bst or Bst 2.0 polymerase, at least 0.8 Unit per microliter;
Betaine at 0.8 M;
Primers at 3.6 µM total;
    FIP and BIP primers at 1.6 µM
    F3 and B3 at 0.2 µM
Magnesium sulfate at 8 mM;
Ammonium sulfate at 10 mM;
Potassium chloride at 10 mM;
Sodium hydroxide to set the starting pH of the reaction mix;
TWEEN® 20 at 0.1%;
dNTP's at 1.4 mM each;
Phenol red at 50 µM.

In a further embodiment, the kit includes LoopF and LoopB primers at 0.8 µM each.

Kits

The embodiments disclosed herein also include kits including the subject devices and which can be used according to the subject methods. The subject kits can include two or more, e.g., a plurality, three or less, four or less, five or less, ten or less, or fifteen or less, or fifteen or more, sample preparation devices or components thereof, and/or optical property modifying devices or components thereof, according to any of the embodiments described herein, or any combinations thereof.

The kits can include one or more compositions and/or reagents, such as any of those described herein, e.g., optical property modifying reagents, amplification compositions, preparation solutions and/or buffers, which can be stored in the kits in containers separate from the devices. In addition, the kits can include any device or other element which can facilitate the operation of any aspect of the kits. For example, a kit can include one or more devices for preparing a sample and/or analyzing one or more characteristics of a sample, e.g., a prepared sample. Kits can also include packaging, e.g., packaging for shipping the devices without breaking.

In certain embodiments, the kits which are disclosed herein include instructions, such as instructions for using devices. The instructions for using devices are, in some aspects, recorded on a suitable recording medium. For example, the instructions can be printed on a substrate, such as paper or plastic, etc. As such, the instructions can be present in the kits as a package insert, in the labeling of the container of the kit or components thereof (i.e., associated with the packaging or subpackaging etc.). In other embodiments, the instructions are present as an electronic storage data file present on a suitable computer readable storage medium, e.g., Portable Flash drive, CD-ROM, diskette, on the cloud, etc. The instructions can be storable and/or reproducible within one or more programs, such as computer applications. The instructions can take any form, including complete instructions for how to use the devices or as a website address with which instructions posted on the world wide web can be accessed.

Utility

Systems and methods as disclosed herein are directed to performing biological assays by effectively evaluating one or more characteristics of biological samples such as, by modifying optical properties of biological samples or aspects thereof.

Many diagnostic systems have been assembled using a paradigm of one disposable and one reusable part. In such embodiments, the disposable part handles the specific patient sample while the reusable part drives the testing and result extraction. However, inclusion of a reusable reader system makes operation complex, costly and can require facilities and/or specific expertise for effective implementation. By not including such a reusable reader, the subject systems are simpler, cheaper and easier to operate than systems implementing such protocols. In other words, the subject systems eliminate the required use of complex optics and/or electrical readouts by applying a simple color changing reaction. The subject systems provide effective and timely information registration, transmission and response. In addition, the subject systems also can apply specific target amplification without a need for thermal cycling.

Also, systems which are entirely composed of simple to use disposables, e.g., lateral flow strips, are often limited to low performing tests and do not include mechanisms for transmitting, registering and/or reacting to the output diagnostic data. However, the subject systems and the devices thereof are fully disposable. The systems can also be applied at the point of care with optimal performance and accuracy and can be interfaced with an information system, such as that of a sample analyzer, for transmitting, registering and responding to a diagnostic output immediately.

Also, the subject disclosure is directed in part to biological sample preparation devices and methods for preparing and delivering biological assay samples. Reagent storage, release and/or other manipulation has been performed by storing reagents in vials that are opened manually by an operator and manipulated using pipettes to, for example, aliquot, mix and/or incubate the reagents. Attempts at resolving challenges associated with reagent storage and/or manipulation such as complexity, large time requirement, and inconvenience have included, for example, applying blister packs and dry reagent storage to utilizing fluidic networks driven by active pressure sources such syringe pumps, compressors, peristaltic pumps and pressurized canisters. Many of the attempts have included applying separate structures on a device and utilizing active components. Such previous attempts have involved a high degree of complexity and cost which in turn has provided limited reliability and usability.

The disclosed subject matter addresses these issues with the described user-powered integrated sample preparation device that provides reagent storage/release and fluid propulsion. As such, the subject embodiments integrate and thus simplify steps including, for example, aliquoting, mixing, measuring and/or incubating using the described self-contained automatic fluidic device. Accordingly, the subject methods and devices are cheaper, less complex and/or more accurate than other such devices or methods. Thus, the subject devices and methods can be applied, for example, to provide efficient on-demand reagent storage and/or release by using effective fluid manipulation, including propulsion, of a sample and/or reagents.

In addition, the optical property modifying devices and related methods described herein provide, for example, effective sample aliquoting protocols. Aliquoting a sample is a procedure applied in biochemical analyses for multiple tests or downstream processing. When miniaturizing and automating biochemical protocols into microfluidic systems, once challenge is how a sample can be accurately aliquoted into multiple sites. One way to do this is to route the sample through bifurcating channels and into multiple reaction chambers. However, according to such a protocol, before reactions can take place in the chambers, the aliquots have to be isolated so that there is no cross talk between the reactions. Such isolation can be achieved using input and/or output valves positioned between each chamber. The valves, for example, allow for an aliquot to enter a chamber and simultaneously evacuate any fluid present in the chamber. Additionally, the valves seal the chamber off from any cross talk. Although using multiple valves works to some extent, such a protocol imposes requirements to actively control the opening and closing of the valves, which in return requires energy and infrastructure to implement, and thus complicating the system design. Also some valve structures work best when primed and as such, require the microfluidic system to be filled with an initial priming liquid. Such a priming step in turn complicates the system workflow. As such, according to versions of the subject methods, the methods do not include priming.

In contrast, the subject devices and methods sufficiently provide automatic fluid flow control by passive aliquoting through one or more portions of a device such that an assay can be performed. For example, one or more fluids, e.g., air and/or biological sample, can be moved and/or prevented from moving through one or more portions of a device with little or no specific user interaction. Passive sealing of the device or portions thereof eliminates the need for active control and minimizes the complexity of the full device and the user steps required to run the device. As such, the subject disclosure provides simple and easy to use assay devices.

Furthermore, the subject devices and methods do not require valves or complicated valve control protocols. As such, the subject disclosure provides a simple and robust implementation of an on-chip aliquoting function with no moving parts. According to the subject embodiments, aliquot volumes and numbers are controlled by channel and chamber geometries.

Furthermore, the system can operate with imprecise loading mechanisms while maintaining very precise aliquot numbers and volumes. In other words, there is no need control the loading pressure, or sample volumes beyond a simple threshold. As such, the aliquoting precision is obtained by the chamber manufacturing precision.

Additionally, the self-sealing characteristic of the system that allows for gas and liquids to pass through until the pores of a selective venting element are sealed can be effectively applied for the prevention of evaporation. As such, for certain samples which need to be incubated at elevated temperatures for the reactions to occur, evaporation though the self-sealing pores is minimized. The subject devices and methods also minimize dead volume as compared to a mechanical valve that requires contact surface area. They also allow for the filling of multiple chambers without channel resistance matching. Furthermore, the devices and methods disclosed herein also protect from washing out any reagents or dry material in the reaction chamber during reaction loading.

Also, the devices and methods, in some versions modify an optical property to allow detection of the modified optical property by an un-assisted human eye. As such, the content of the subject disclosure eliminates a need for complex evaluation techniques or equipment to read or interpret a signal generated by a biological assay. Because a user can recognize a modified optical property with a user's eye, performing an assay with the subject methods can reduce time and expense compared to performing such an assay using other equipment or methods. The subject devices can also be finely tuned to provide efficient energy conduction, e.g., heat or electrical energy, into a fluidic network and/or specific variations in optical properties such as adhesive color. Also, previous biological assays have also involved a high degree of complexity in analysis, e.g., have required the use of one or more computer, which in turn has provided limited reliability and usability. Accordingly, the subject methods and devices are cheaper, less complex and/or more accurate than other such devices or methods.

In addition, methods of assembling the subject devices have included patterning a substrate layer, e.g., a layer of glass, silicon or polymer, and then bonding it to a non-patterned sealing layer using chemical or physical bonds. Once the fluidic device was assembled, e.g., assembled by being bonded and sealed, then is has been integrated into a housing or cassette that provides additional functionality required to utilize the fluidic system. However, many microfluidic device bonding techniques have had the potential to damage any fragile pre-loaded reagents. By employing the device conformation disclosed herein, such difficulties are avoided since the adhesive layer can be employed for simultaneously sealing the microfluidic system and integrating into the final assembly while preserving reagent functionality, such as functionality of reagents pre-loaded into reaction chambers. As such, the subject methods and devices simplify the operation of such devices, as well as the manufacturing of such devices while improving effectiveness in generating an assay result.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pennsylvania: Mack Publishing Company, 1990); Carey and Sundberg *Advanced Organic Chemistry* $3^{rd}$ Ed. (Plenum Press) Vols A and B (1992).

Figure 20:
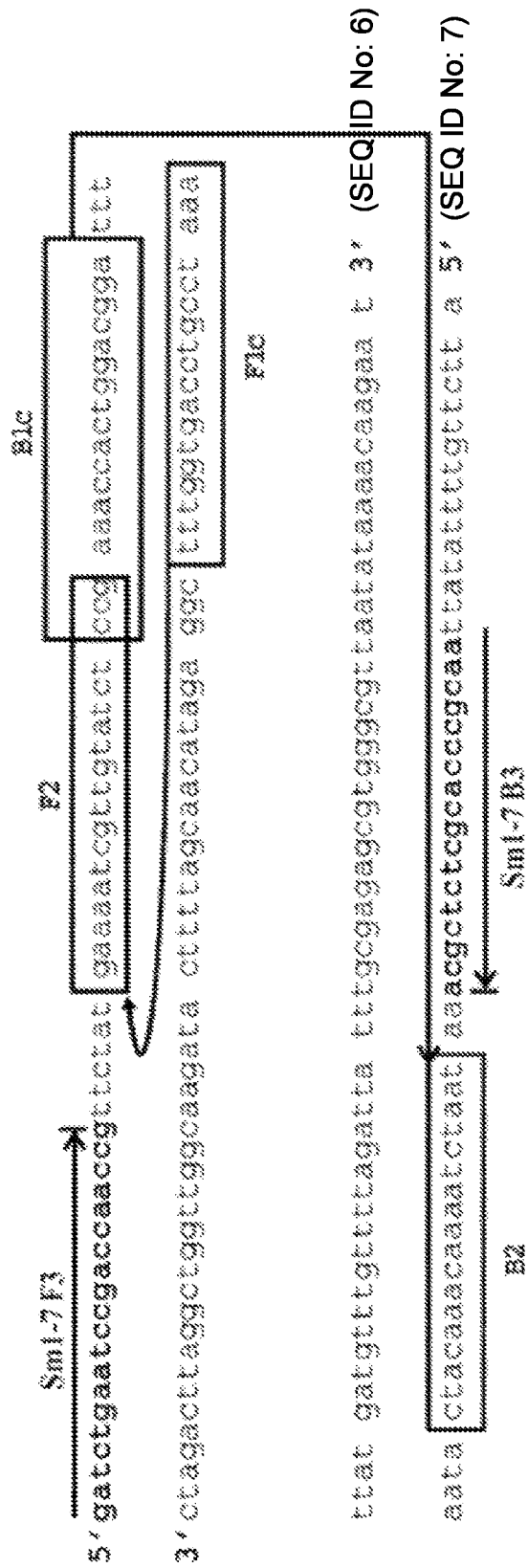
FIG. 20 shows the DNA sequence of a template nucleic acid molecule target region from *Schistosoma mansoni* (SEQ ID NOS: 6 and 7), according to an embodiment.

Example 1: Colorimetric Detection of a Nucleic Acid Amplification Reaction Product In an assay for colorimetric detection of a nucleic acid amplification reaction product, the following reagents were mixed together to produce a 2× reagent mix:
 Magnesium Sulphate (Sigma Aldrich) at 16 mM
 Ammonium Sulphate (Sigma Aldrich) at 20 mM
 Potassium Chloride (Sigma Aldrich) at 20 mM
 Sodium hydroxide (Sigma Aldrich) at a concentration that sets the starting pH of the reagent mix to 8.8 pH The reagent mix was adjusted to an initial pH of 8.8 to enable efficient initial polymerization. The reagent mix was autoclaved for 1 hour for sterilization. The following ingredients were then added (in a sterile form) to the reagent mix to generate the reaction mix:

TWEEN®-20 (Sigma Aldrich) at 0.1% (v/v)
dNTPs (NEB) at 1.4 mM each
Phenol Red (Sigma Aldrich) at 50 µM
Bst polymerase (NEB) at 0.8 Unit per microliter (the enzyme storage buffer contributing 1 mM Tris buffer, 5 mM KCl, 0.01 mM EDTA, 0.1 mM DTT, 0.01% TRITON X-100™ (v/v) and 5% Glycerol ((w/v) to the reaction mix)
Betaine (Sigma Aldrich) at 0.8 M Primers and a nucleic acid template were added to the reaction mix. The primers were designed for LAMP and included two pairs of primers (solubilized in 1×Tris EDTA buffer) at a total concentration of 3.6 µM as described above. Primer F3 has the sequence: GATCTGAATCCGAC-CAACCG (SEQ ID NO: 1); primer B3 has the sequence: AACGCCCACGCTCTCGCA (SEQ ID NO: 2); the primer FIP has the sequence: AAATCCGTCCAGTGGTTTTTTT-GAAAATCGTTGTATCTCCG (SEQ ID NO: 3); and the primer BIP has the sequence: CCGAAACCACTGGACG-GATTTTTATTTTTAATCTAAAACAAACATC (SEQ ID NO: 4). The nucleic acid template molecule was purified from *Schistosoma mansoni*. FIG. 20 shows the SM1-7 target region of the nucleic acid template molecule (see Hamburger et al, Detection of *Schistosoma mansoni* and *Schistosoma haematobium* DNA by Loop-Mediated Isothermal Amplification: Identification of infected Snails from Early Prepatency, *Am J Trop Med Hyg*, 2010). The positive test reactions contained template DNA, and the negative control reactions contained water. The reaction mixes had a starting pH in the range of 7.5-8.5. The reaction mixes were heated in micro-tubes to 63° C. on a thermocycler to allow template amplification. After a predetermined reaction period of 45 minutes, during which sufficient template amplification occurred, the resultant color of the reaction mix was visually observed.

Figure 21:
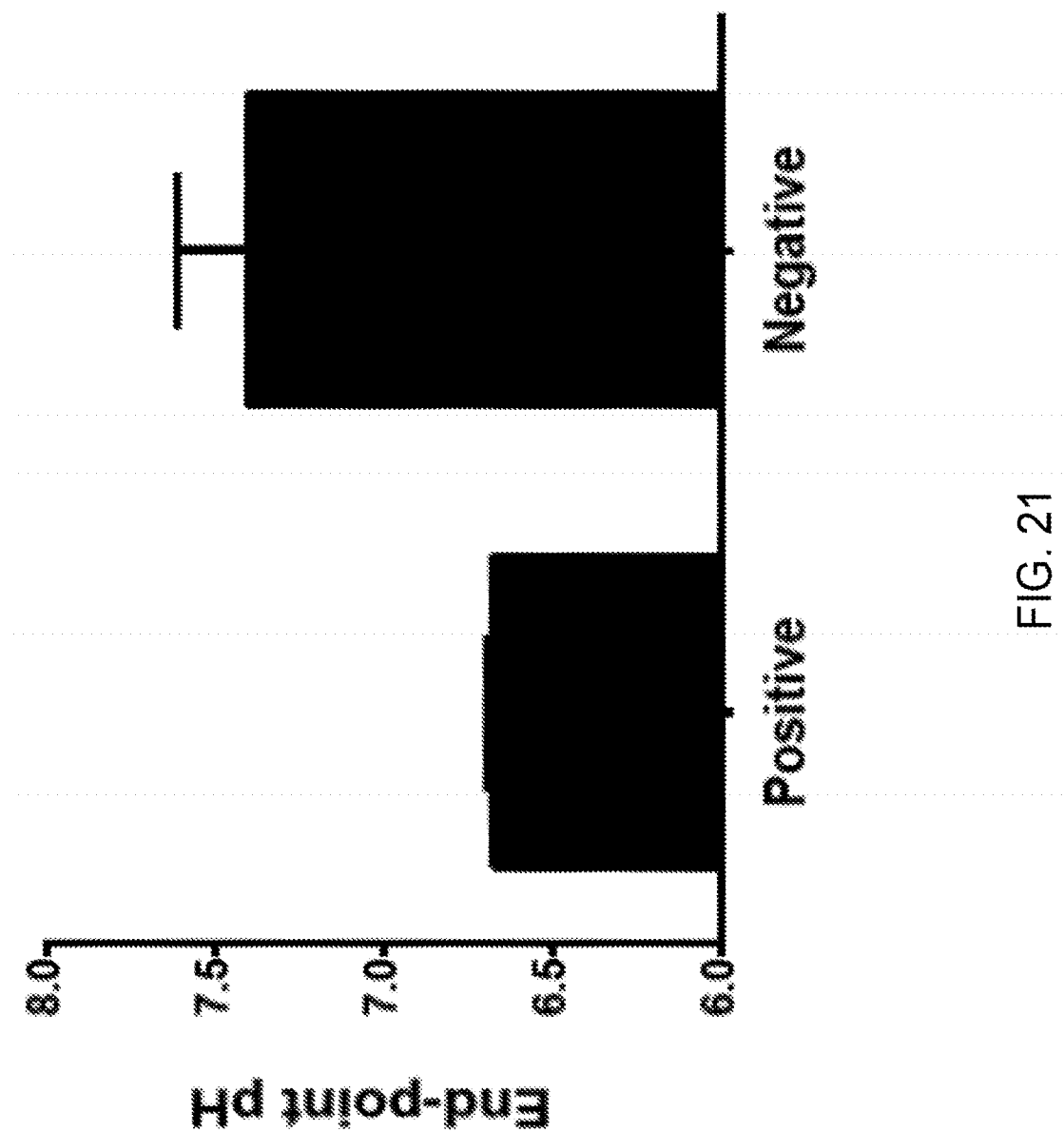
FIG. 21 is a graph indicating pH measurements for positive and negative isothermal amplification reactions, according to an embodiment.
Figure 22:
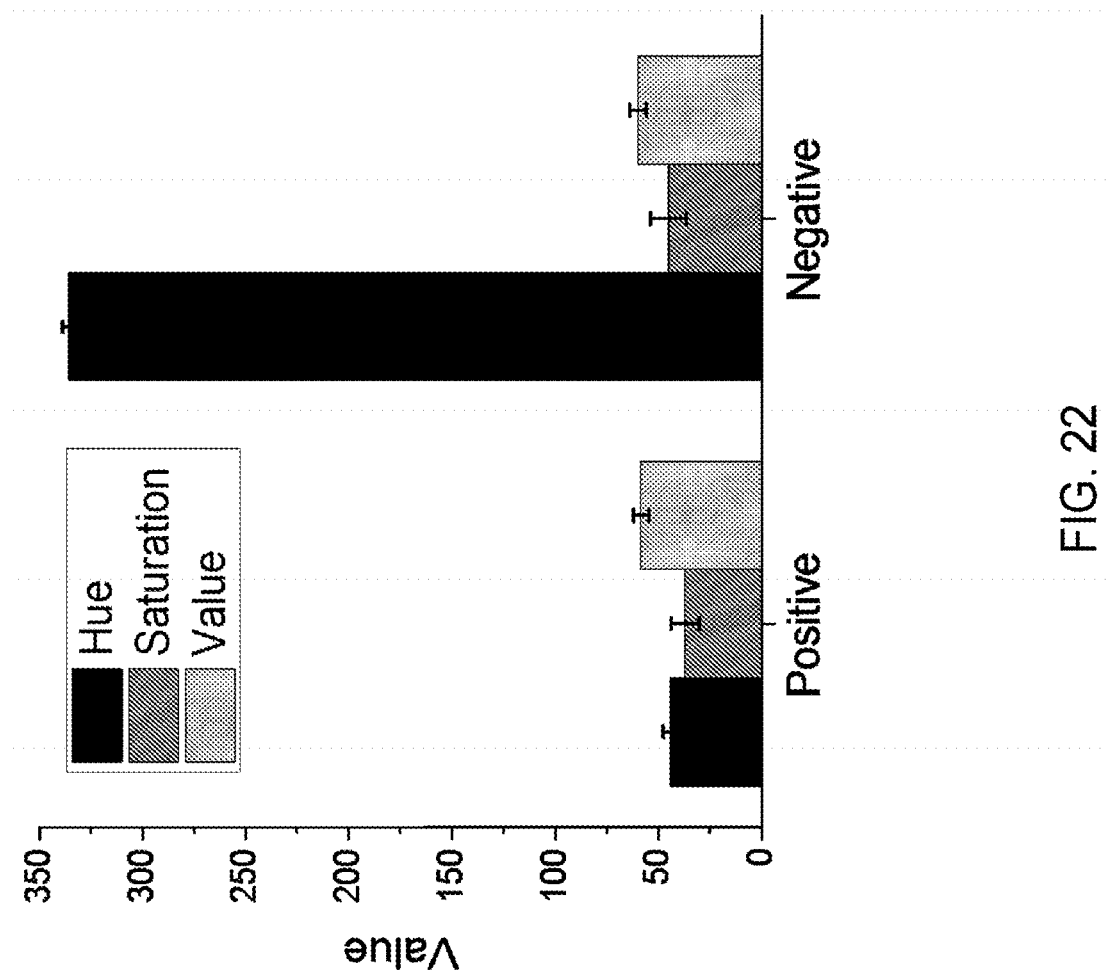
FIG. 22 is a graph showing the detection of color (hue) of positive and negative isothermal amplification reactions at the reaction endpoints, according to an embodiment.
Figure 23:
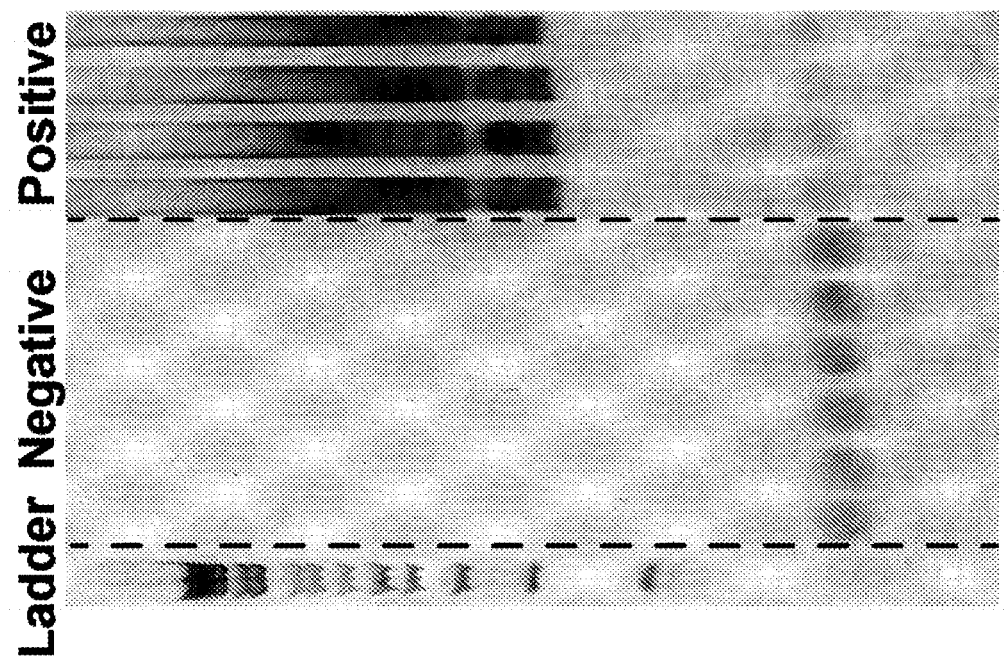
FIG. 23 shows the results of a gel electrophoresis assay of positive and negative isothermal amplification reaction products, according to an embodiment.

During the amplification process, the pH of the reaction mix was reduced from 7.5-8.5 to around 6.6 in a repeatable fashion. FIG. 21 is a graph showing the pH measurements for repeated positive (test) and negative (negative control) amplification reactions. The halochromic agent used was Phenol red, which has a transition pH range of 6.8-8.2. Phenol red changes color over this transition pH range from red to yellow (when the pH is lowered from the upper pH limit to the lower pH limit). In the assay, the reaction mix changed color from red (at pH 8.0) to yellow (at pH 6.6) in response to the pH change during nucleic acid amplification. FIG. 22 is a graph showing the difference in contrast value using HSV (hue, saturation, value) of images of the reaction mixes of a positive and negative amplification reaction at the reaction endpoints. The color change is quantitatively demonstrated in the hue variable. To confirm that the color change was due to target DNA amplification, endpoint reactions were analyzed using gel electrophoresis to verify the presence of amplicons (FIG. 23).

Using this method, amplification of a DNA template can be easily observed, either at the reaction end-point or in real-time throughout the reaction, by visually observing the color change in the reaction mix, or by measuring the absorbance or fluorescence of the reaction mix. This mechanism generates much larger contrast in comparison to other colorimetric detection techniques and can be imaged without the need of expensive optical instrumentation.

Example 2: Detection of LAMP Amplification Using a Visual Halochromic Agent

LAMP reactions were performed with a reaction mix comprising of: 10 mM $(NH4)_2SO4$, 15 mM KCl, 0.1 mM EDTA, 0.1 mM DTT, 0.01% TRITON X-100™ (v/v), 5% Glycerol, 8 mM $MgSO_4$, 1.4 mM each dNTPs, 0.1% v/v TWEEN®-20, 0.8 M Betaine. Three primer pairs, specific to different targets, were added to a final concentration of 1.6 µM each for FIP/BIP, 0.2 µM each for F3/B3, 0.4 µM each for LoopB/F. The final reaction volume is 10 µL and was held at 63° C. for different incubation times.

Figure 24:
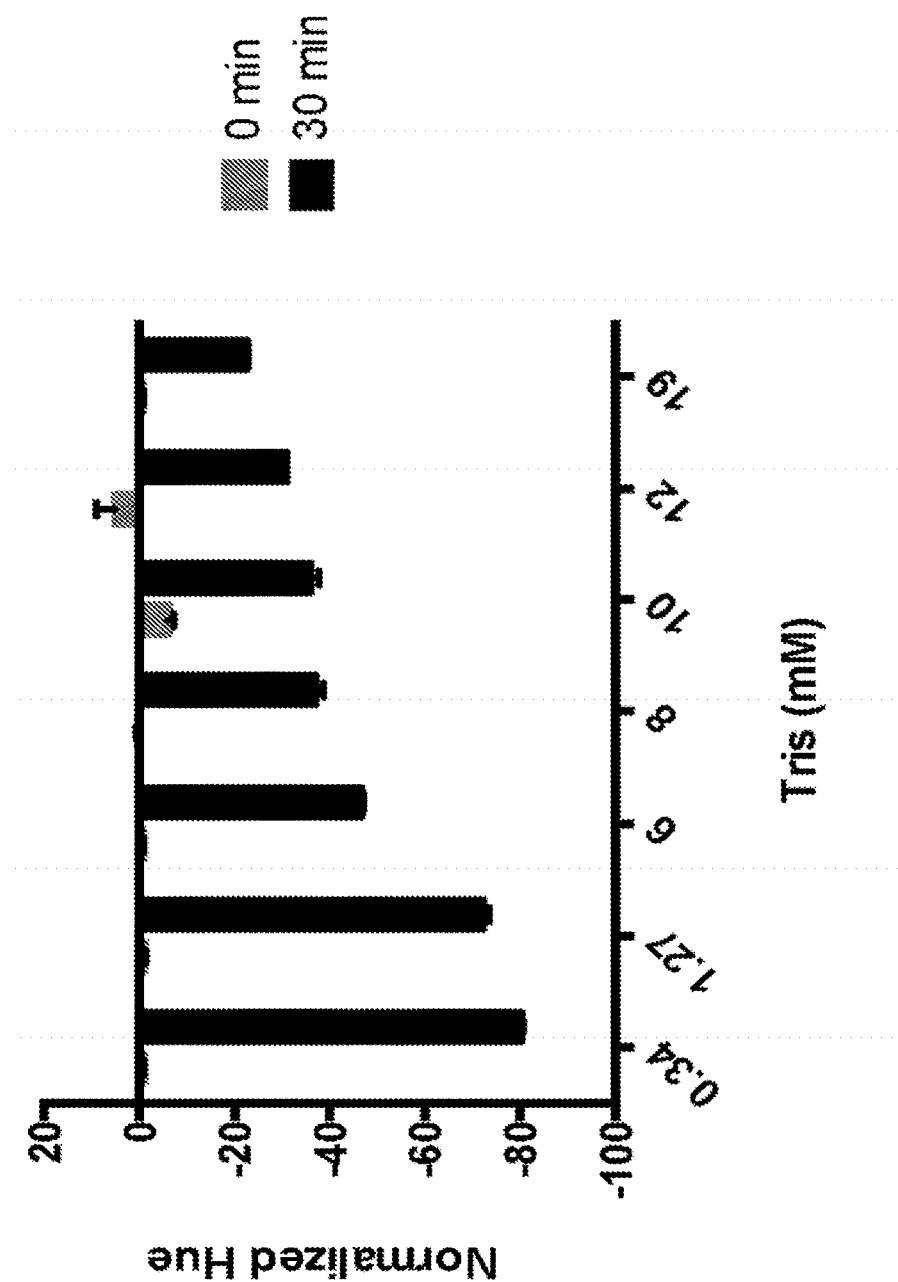
FIG. 24 shows the normalized hue values for amplification reactions using various Tris buffer concentrations, according to an embodiment.

In FIG. 24, the final Tris buffer concentration of the reaction mix was varied from 0.34 mM to 19 mM (by varying amount of Tris buffer formulated to pH 8.8). Reactions were performed with primers for lambda phage DNA, 5 ng of lambda DNA (New England Biolabs), 0.8 U/µl Bst 2.0 DNA polymerase (New England Biolabs) and 0.2 mM Neutral Red (Sigma Aldrich). The reaction tubes were then imaged and the Normalized Hue value was calculated for the color of the reaction mix. The Normalized Hue value was defined as the difference in Hue values between a positive and a no-template negative reaction. A color change, indicated by a change in the Normalized Hue value above the visualization threshold (dotted line), was observed for buffer concentrations as high as 19 mM Tris. This indicates that reaction mix with buffer capacities equivalent to >1 mM and <19 mM Tris allow enough pH change for visual color change detection.

Figure 25:
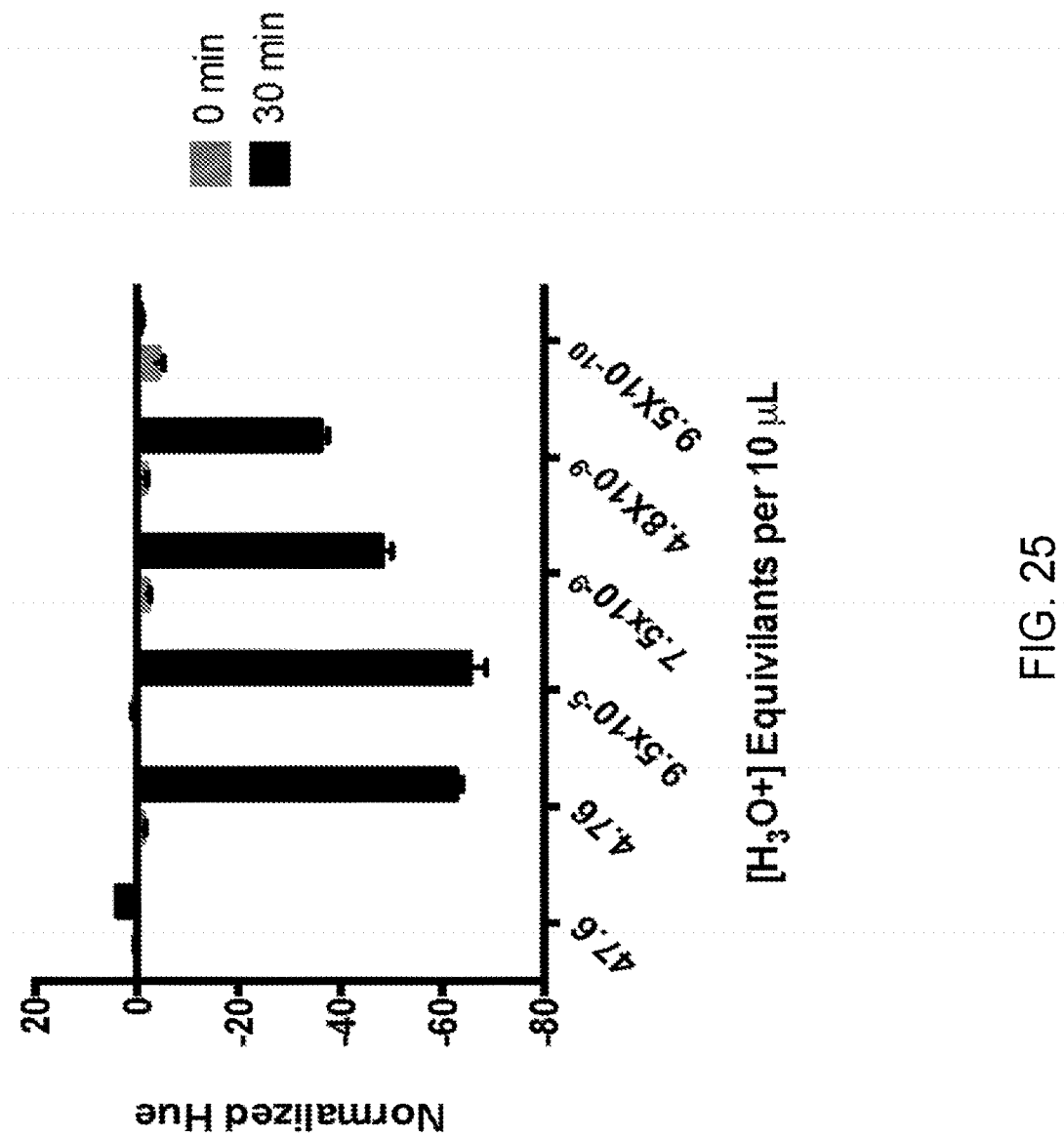
FIG. 25 shows the normalized hue values for amplification reactions using varying amounts of additional hydronium ion equivalents, according to an embodiment.

In FIG. 25, the tolerance of this visual detection method to excess hydronium ions added to the reaction mix was evaluated. This tolerance is important to allow the use of a wide variety of DNA samples which can add a range of hydronium or hydroxide ion equivalents to the reaction. Reactions were performed with 2 mM final Tris buffer concentration, 5 ng lambda DNA target, 0.8 U/µL Bst DNA polymerase and 0.2 mM Neutral Red halochromic agent. The change in Normalized Hue value indicates that this visual detection chemistry works with $4.8 \times 10^{-9}$ till $4.8 \times 10^{-18}$ additional hydronium ion equivalent per 10 µL reaction.

Figure 26A:
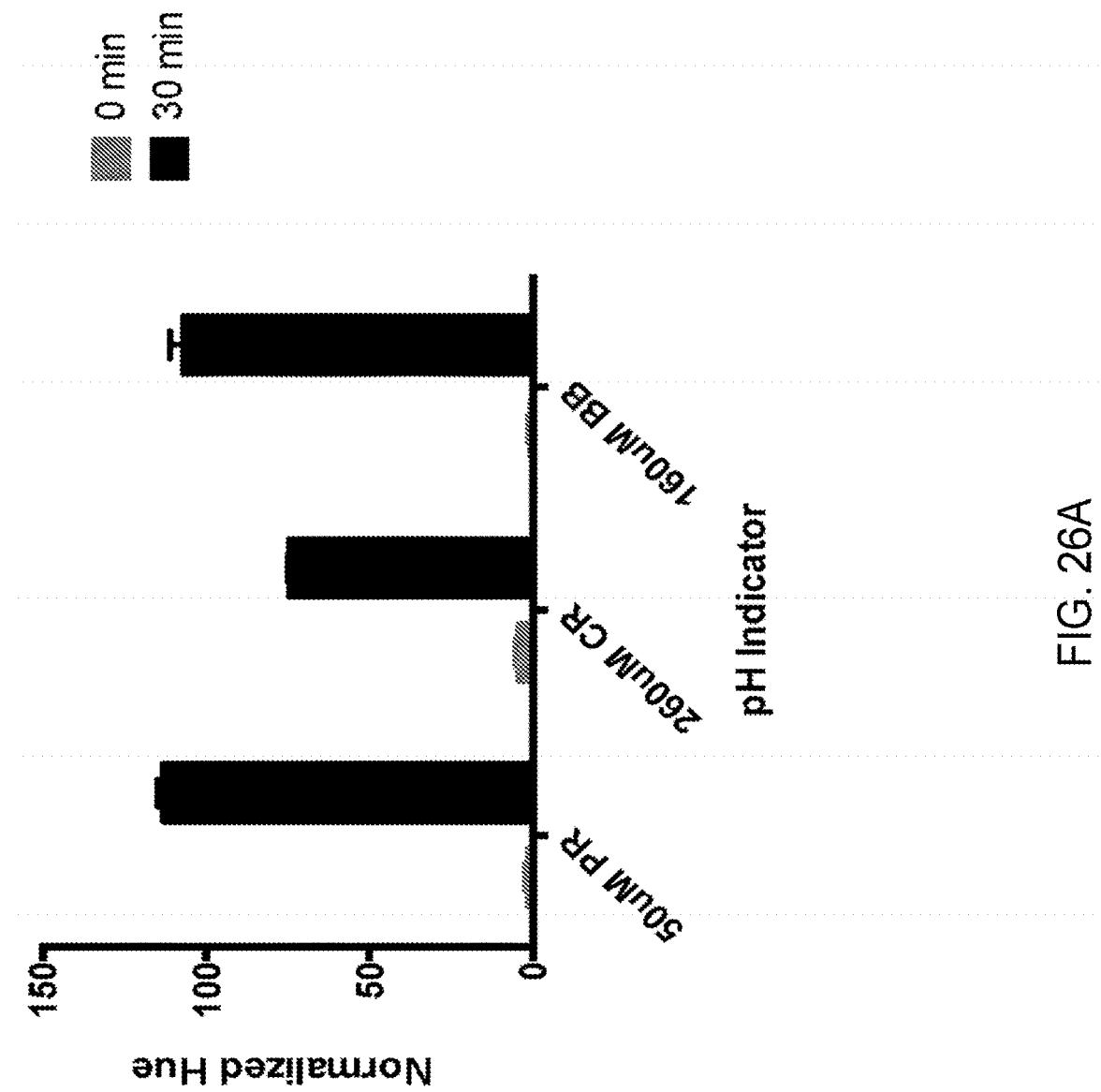
FIGS. 26A, 26B, 26C, and 26D show the normalized hue values for amplification reactions using various halochromic agent concentrations, according to an embodiment.
Figure 26B:
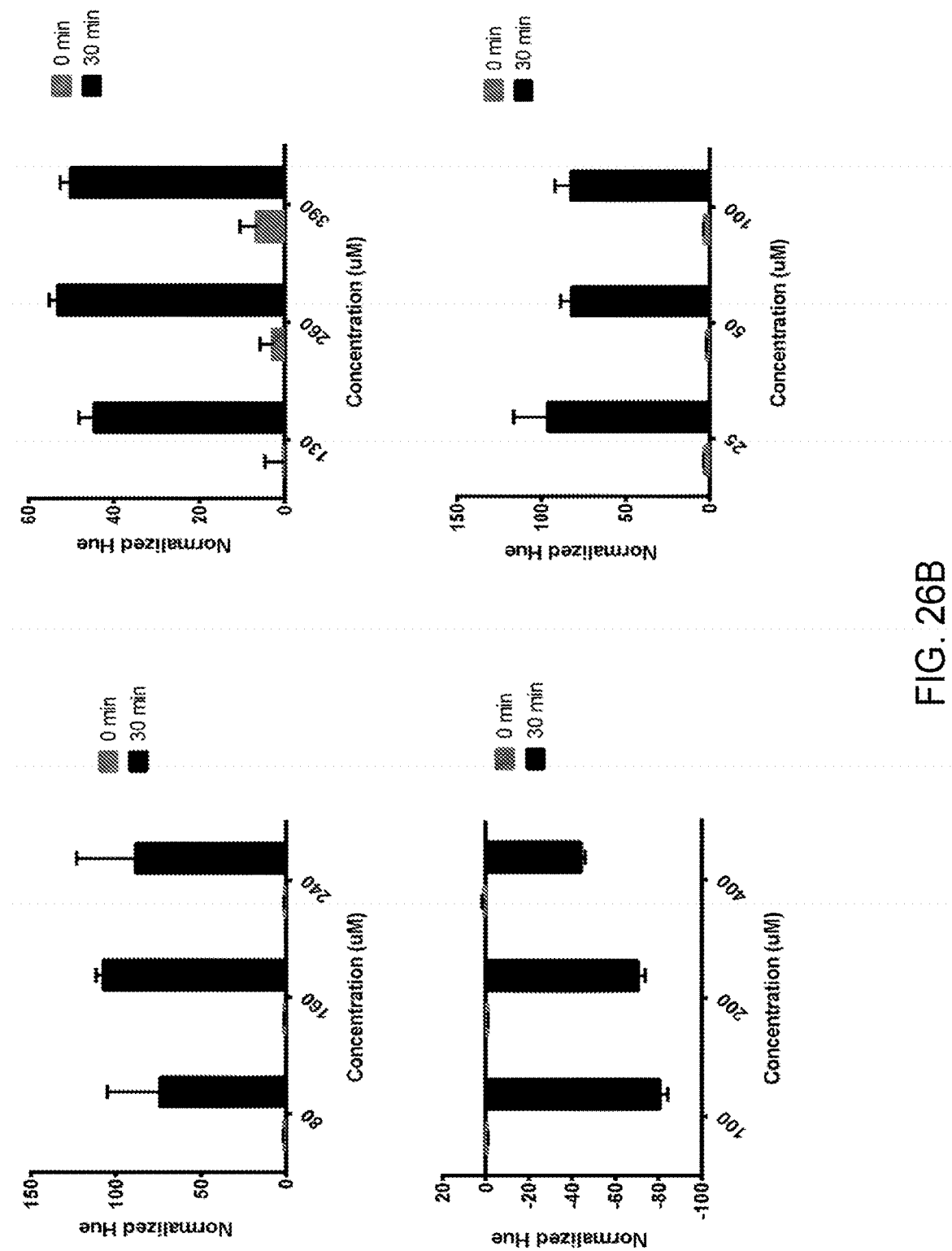
Figure 26C:
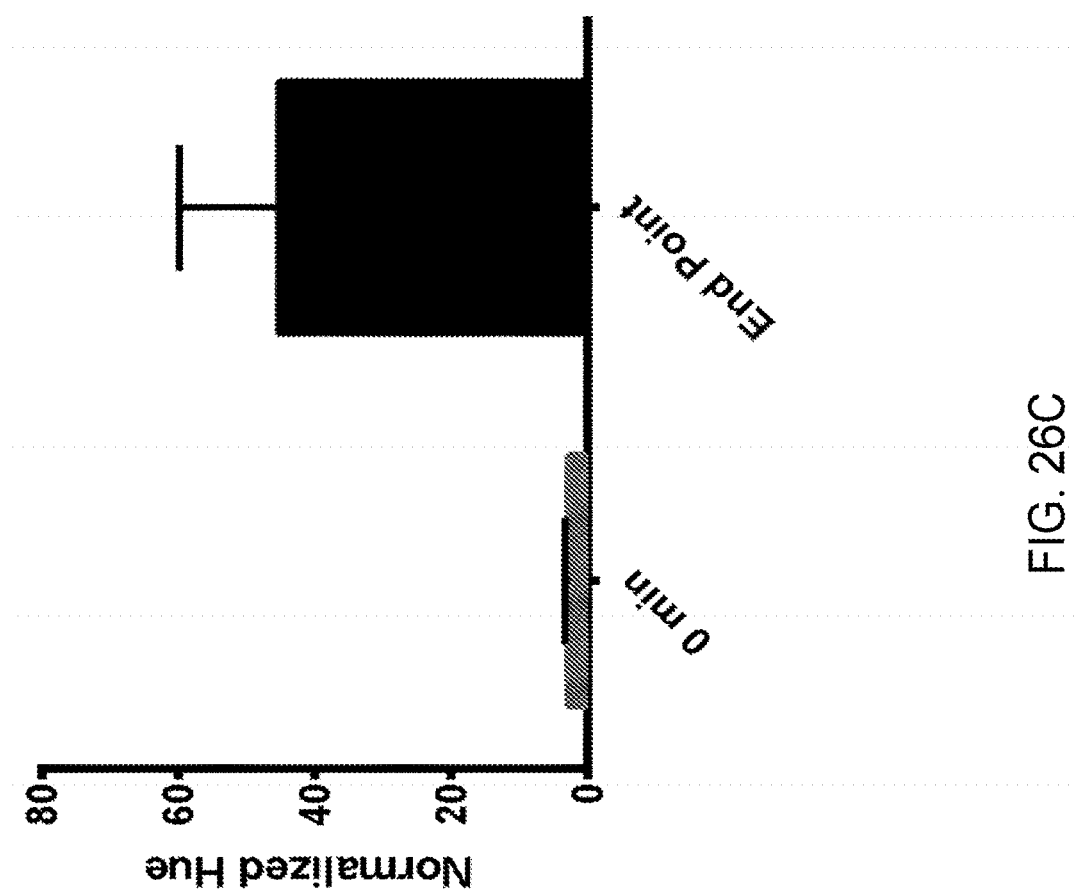
Figure 26D:
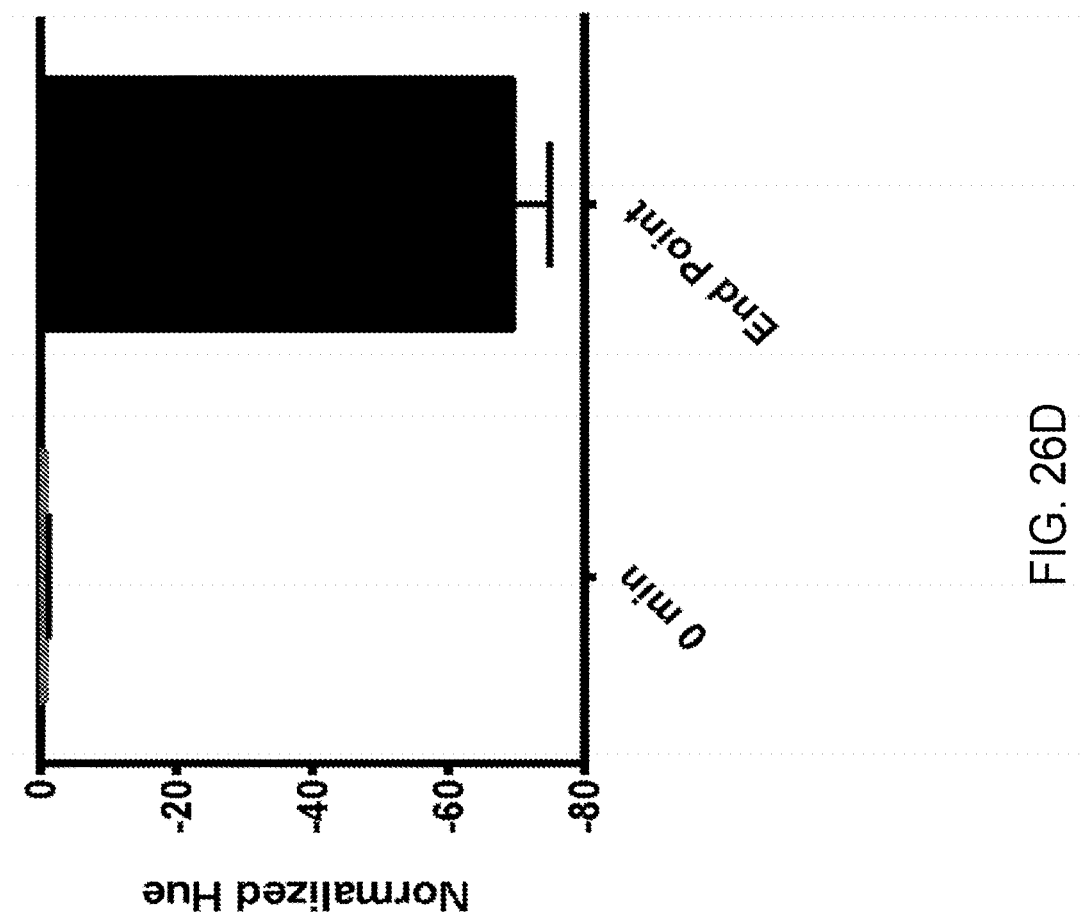

In FIGS. 26A-26D, the compatibility of different pH indicators and amplification targets with visual detection of LAMP amplification was evaluated. The reactions were performed with final Tris buffer concentration in the range of 1.2-1.3 mM and 0.8 U/µL Bst DNA polymerase. Three different indicator were tested with 5 ng lambda DNA target: 50 µM Phenol Red, 260 µM Cresol Red and 160 µM Bromothymol Blue (FIG. 26A). High contrast change in the normalized hue value was observed for all indicators tested.

Concentration sweeps were also performed for these indicators Bromothymol Blue (FIG. 26B top left), Cresol Red (FIG. 26B top right), Neutral Red (FIG. 26B bottom left) and Phenol Red (FIG. 26B bottom right) with Lambda target, which demonstrated the wide range of concentrations that are compatible with the chemistry. LAMP assays using 130 ng *Schistosoma mansoni* gDNA with 50 µM Phenol Red (FIG. 7C) and Human GAPDH mRNA with 0.2 mM Neutral Red (FIG. 26D) were also tested visual detection of these targets was demonstrated at end-point.

Figure 27:
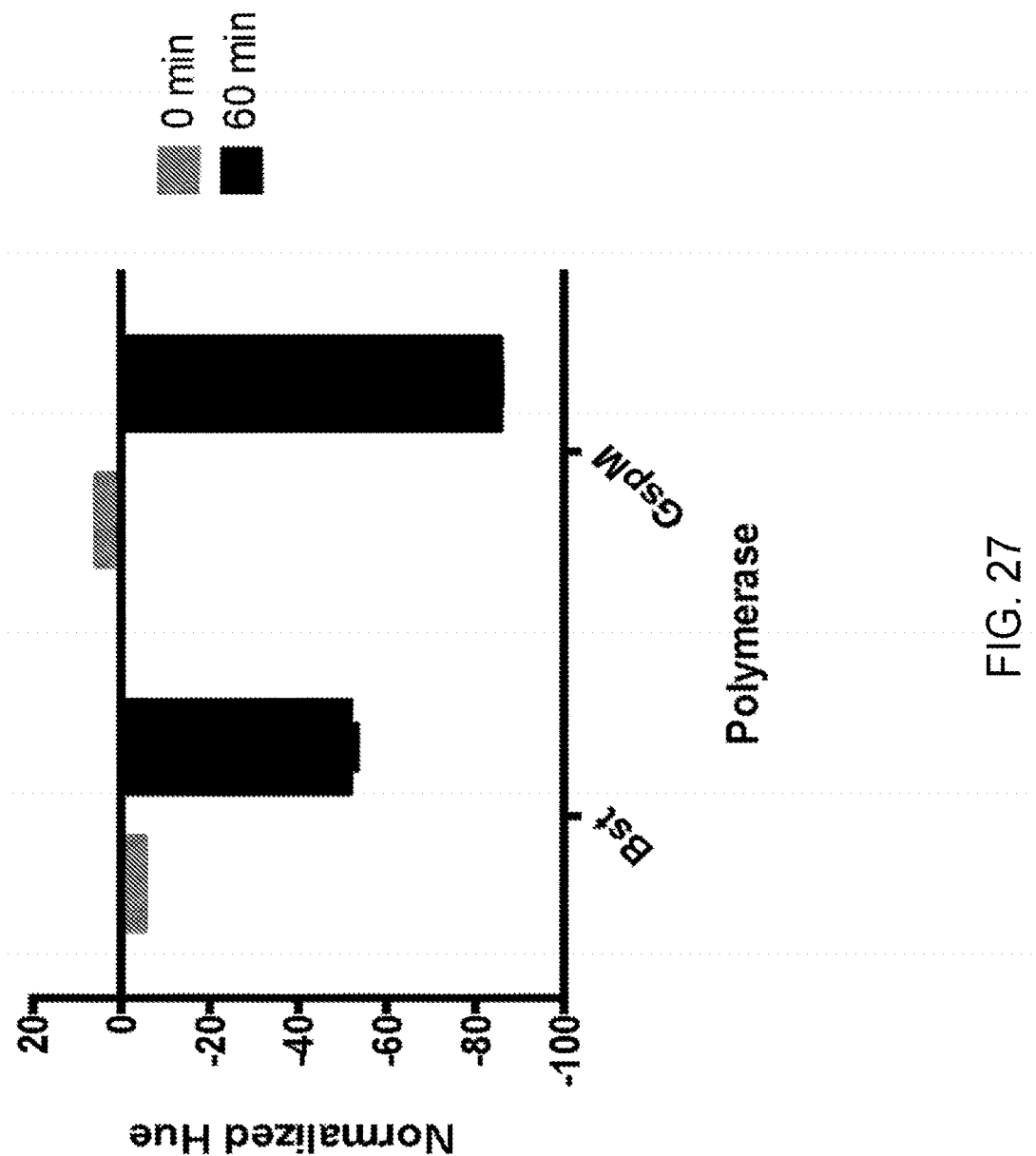
FIG. 27 shows the compatibility of different polymerases with visual detection of LAMP amplification, according to an embodiment.

In FIG. 27, the compatibility of different polymerases with visual detection of LAMP amplification was evaluated. The reactions were performed with 1.3 mM final Tris buffer concentration, 5 ng lambda DNA target and 0.2 mM Neutral Red. 0.8 U/µl of two different polymerases, Bst 2.0 and Gspm 2.0 (OptiGene), were used. High contrast color change was observed for both polymerases after 60 minutes of incubation (FIG. 27).

TABLE 2

| Sequences Used | |
|---|---|
| Lambda FIP | SEQ ID NO: 5 |
| Lambda BIP | SEQ ID NO: 23 |
| Lambda F3 | SEQ ID NO: 24 |
| Lambda B3 | SEQ ID NO: 8 |
| Lambda Loop F | SEQ ID NO: 9 |
| Lambda Loop B | SEQ ID NO: 10 |
| Schistosoma F3 | SEQ ID NO: 1 |
| Schistosoma B3 | SEQ ID NO: 2 |
| Schistosoma FIP | SEQ ID NO: 3 |
| Schistosoma BIP | SEQ ID NO: 4 |
| GAPDH F3 | SEQ ID NO: 11 |
| GAPDH B3 | SEQ ID NO: 12 |
| GAPDH FIP | SEQ ID NO: 13 |
| GAPDH BIP | SEQ ID NO: 14 |
| GAPDH Loop F | SEQ ID NO: 15 |
| GAPDH Loop B | SEQ ID NO: 16 |

Figure 28A:
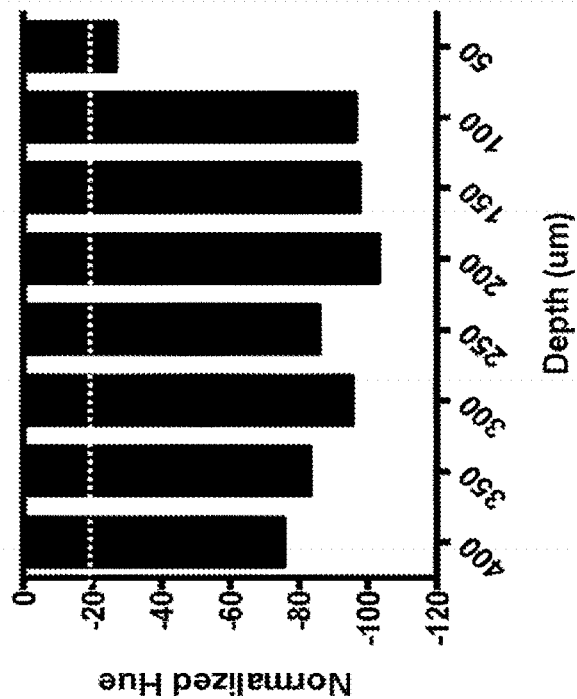
FIGS. 28A and 28B show the normalized hue values for amplification reactions using varying channel depths, according to an embodiment.
Figure 28B:
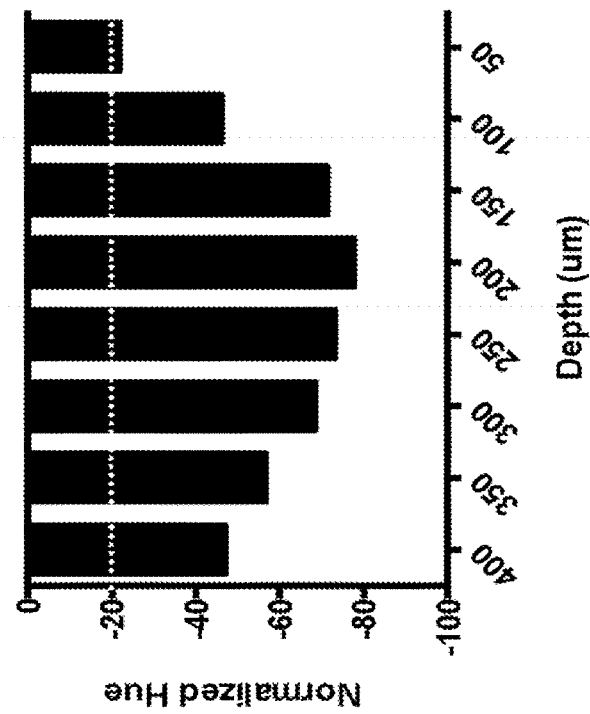

Example 3: Visual Detection of LAMP Amplification in Sub-Millimeter Path Lengths LAMP reactions were performed as in Example 1 with 1.3 mM final Tris buffer concentration (buffer formulated to pH 8.8), 0.8 U/µl of Bst 2.0 DNA Polymerase, 5 ng lambda DNA template and 0.2 mM Neutral Red or 160 µM Bromothymol Blue. Both the positive and the no-template negative reactions were added after amplification to flow chambers with varying channel depths (FIG. 28A for Neutral Red and FIG. 28B for Bromothymol Blue). These flow chambers were machined in acrylic with channel depths ranging from 50 µm to 400 µm. High contrast color difference (above the visual detection threshold; dotted line) between the positive and the negative reactions was observed for channel depths of 50 µm and above. This demonstrates that this visual detection chemistry is amenable for use in reaction chambers with sub-millimeter path lengths (depths) and above. Such reaction chambers can be used to reduce the amount of reagents used and to allow multiple reactions to take place in a certain footprint (e.g. in a microfluidic cartridge).

Figure 33:
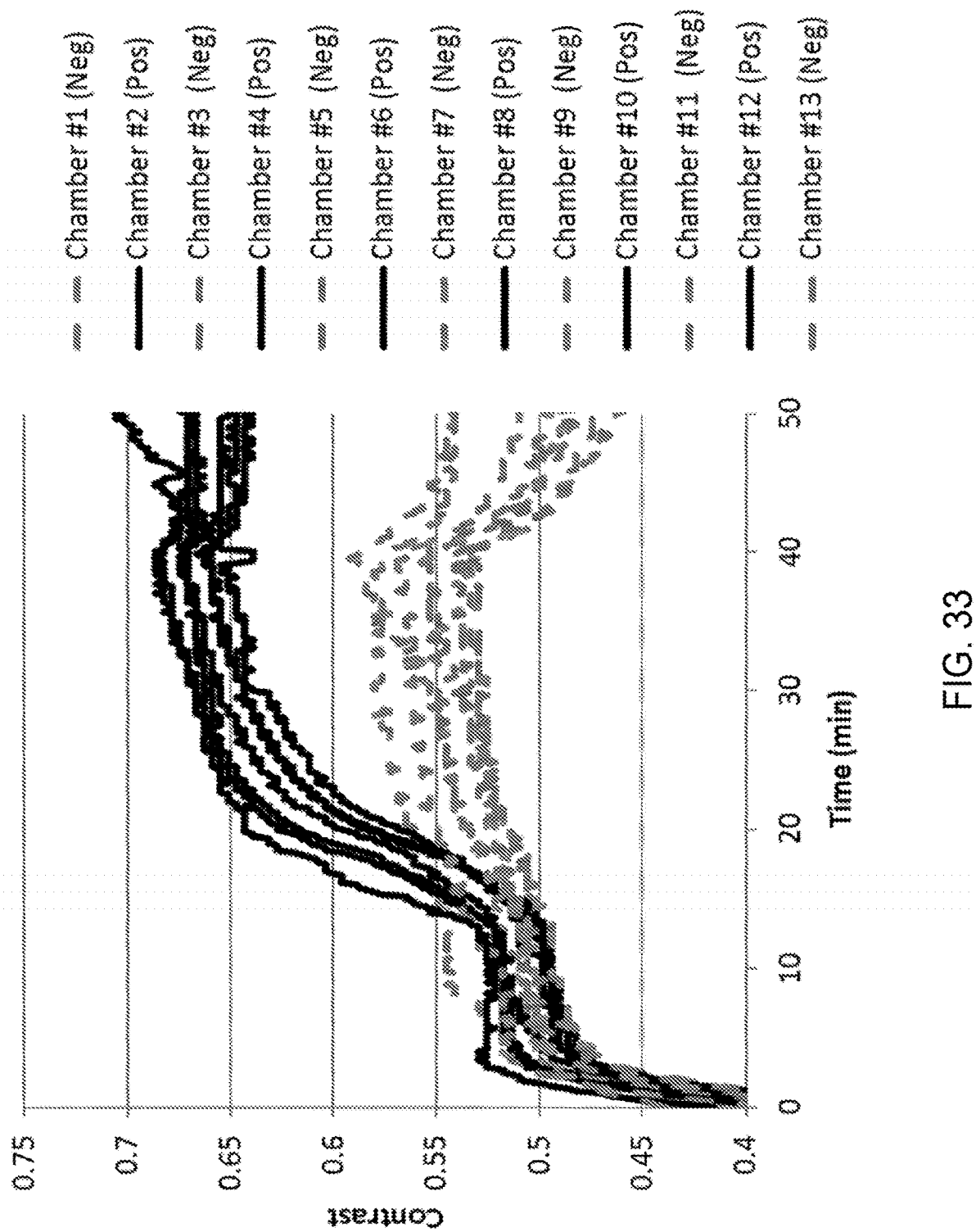
FIG. 33 provides LAMP amplification data from amplification in a device having a selective venting element.

Example 4: Detection of LAMP Amplification in Devices Having a Selective Venting Element LAMP reactions were performed as in Example 1 with 1.6 mM final Tris buffer concentration (buffer formulated to pH 8.8), 0.8 U/µl of Bst 2.0 DNA Polymerase, 5 ng lambda DNA template, and Phenol Red and Bromothymol Blue at 50 µM and 160 µM concentrations respectively. The solution was loaded into a fluidic device with reaction chambers consisting of a sample receiving input and a vent outlet. The vent outlet of each reaction chambers was sealed with a selective venting element, e.g., a self-sealing element. Alternating chambers had lambda primers dried in them. The sample receiving inputs are all connected to a bus channel connected to the device inlet. The reaction chambers were heated to 63° C. for 1 hour. The color change in the chambers was measured with a camera and the data is shown in FIG. 33.

Figure 29:
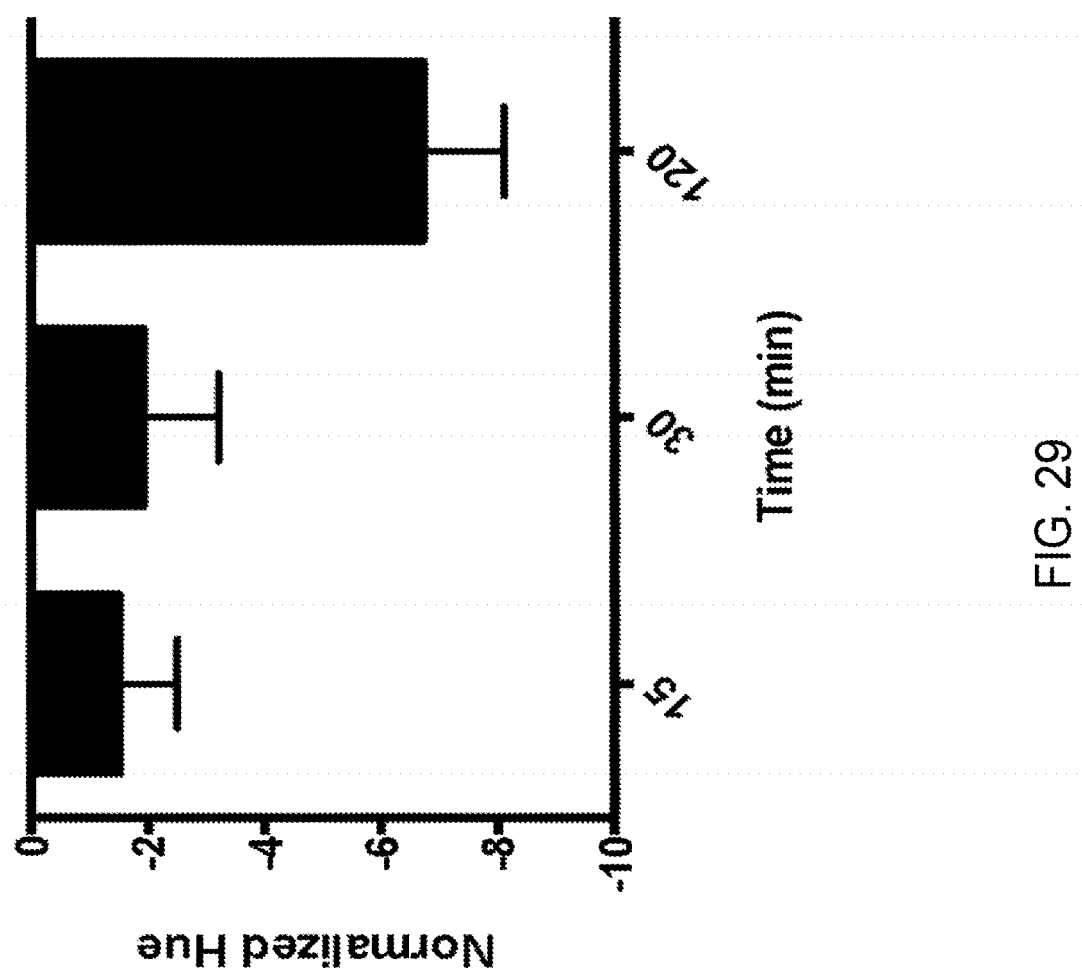
FIG. 29 shows the normalized hue values over time for SDA, according to an embodiment.

Example 5: Detection of Strand Displacement Amplification (SDA) Using a Visual Halochromic Agent SDA reactions were performed using a reaction mix comprising of: 1.3 mM final Tris buffer concentration (buffer formulated to pH 8.8), 10 mM $(NH4)_2SO4$, 50 mM KCl (adjusted to pH 8.5), 8 mM $MgSO_4$, 4.4 mM each dATP, dGTP, dTTP, 0.8 mM dCTP-αS (TriLink Biotechnologies), 0.1% v/v TWEEN®-20, 0.8 M Betaine, 0.32 U/µl Bst DNA polymerase (New England Biolabs), 0.2 U/µL BSoBI (New England Biolabs) and 0.2 mM Neutral Red halochromic agent. Primers designed for human BRCA1 (SDAf: SEQ ID NO: 17; SDAr: SEQ ID NO: 18; BF: SEQ ID NO: 19; BR: SEQ ID NO: 20) were added to the reaction at 0.5 µM final concentration each. 5 ng of HeLa gDNA was added to a final reaction volume of 25 µL and was held at 65° C. for different incubation times. A change in Normalized Hue value over time (FIG. 29) indicates that this visual detection chemistry works with SDA.

Example 6: Detection of PCR Amplification Using a Visual Halochromic Agent

Figure 30:
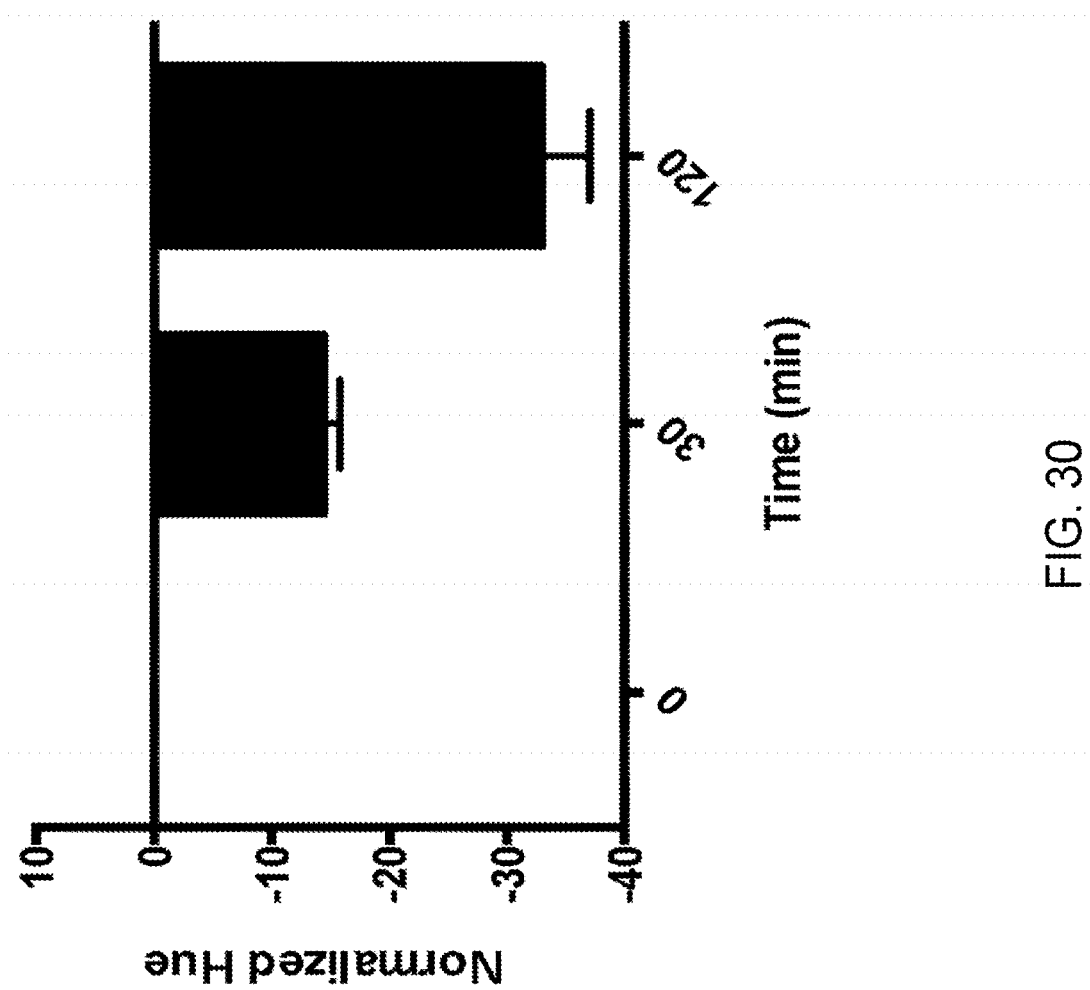
FIG. 30 shows the normalized hue values over time for PCR, according to an embodiment.

PCR reactions were performed using a reaction mix comprising of: 50 mM KCl and 2 mM $MgCl_2$ (pH adjusted 8.5), 0.5 mM each dNTP, 5 U Taq DNA polymerase (New England Biolabs) and 0.2 mM Neutral Red halochromic agent. Total carry-over Tris-HCl concentration from enzyme storage buffer and primers (Forward: SEQ ID NO: 21; Reverse: SEQ ID NO: 22) was 1.15 mM in the final reaction mix. Primers were designed for Escherichia coli 16s rRNA gene and added to the reaction at 0.5 µM final concentration each. 10 ng of E. coli gDNA was added to a final reaction volume of 25 µL and was initially held at 95° C. hold for 2 min, followed by 50 cycles of 95° C. for 10 sec, 55° C. for 30 sec, 68° C. for 30 sec. A change in Normalized Hue value over time (FIG. 30) indicates that this visual detection chemistry works with PCR.

Figure 31B:
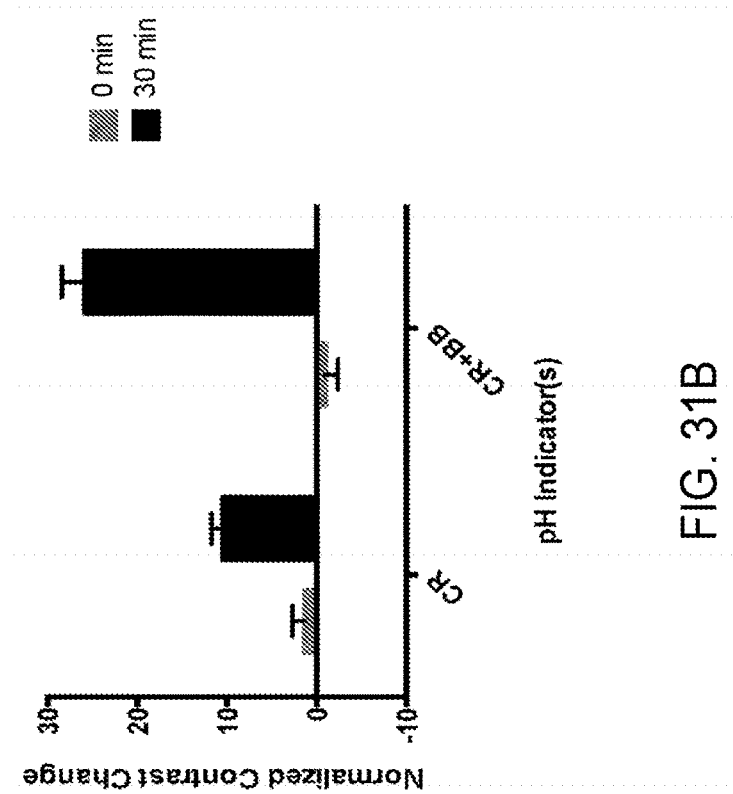
FIGS. 31A and 31B show the normalized contrast changes for amplification reactions using combinations of halochromic agents, according to an embodiment.
Figure 31A:
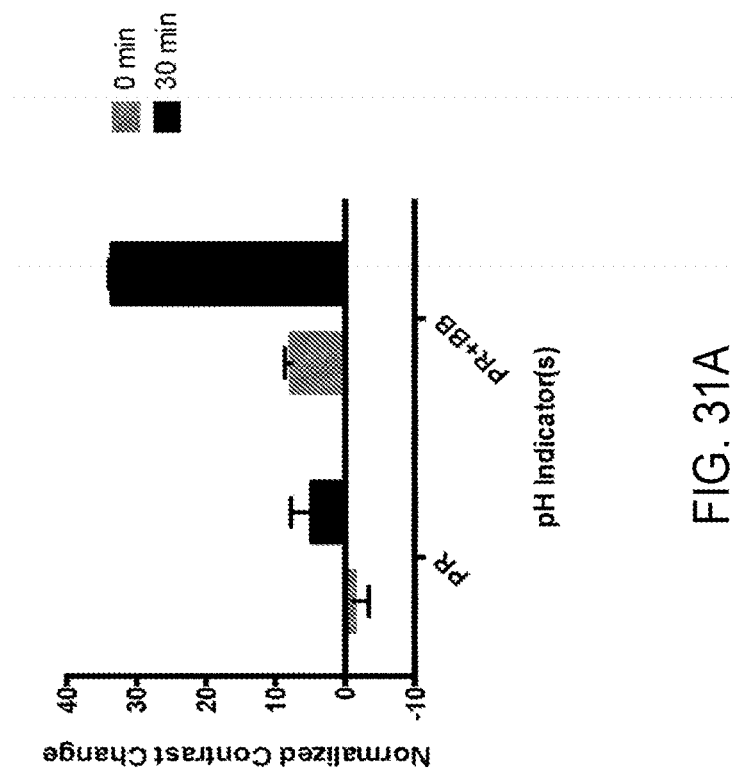
Figure 32:
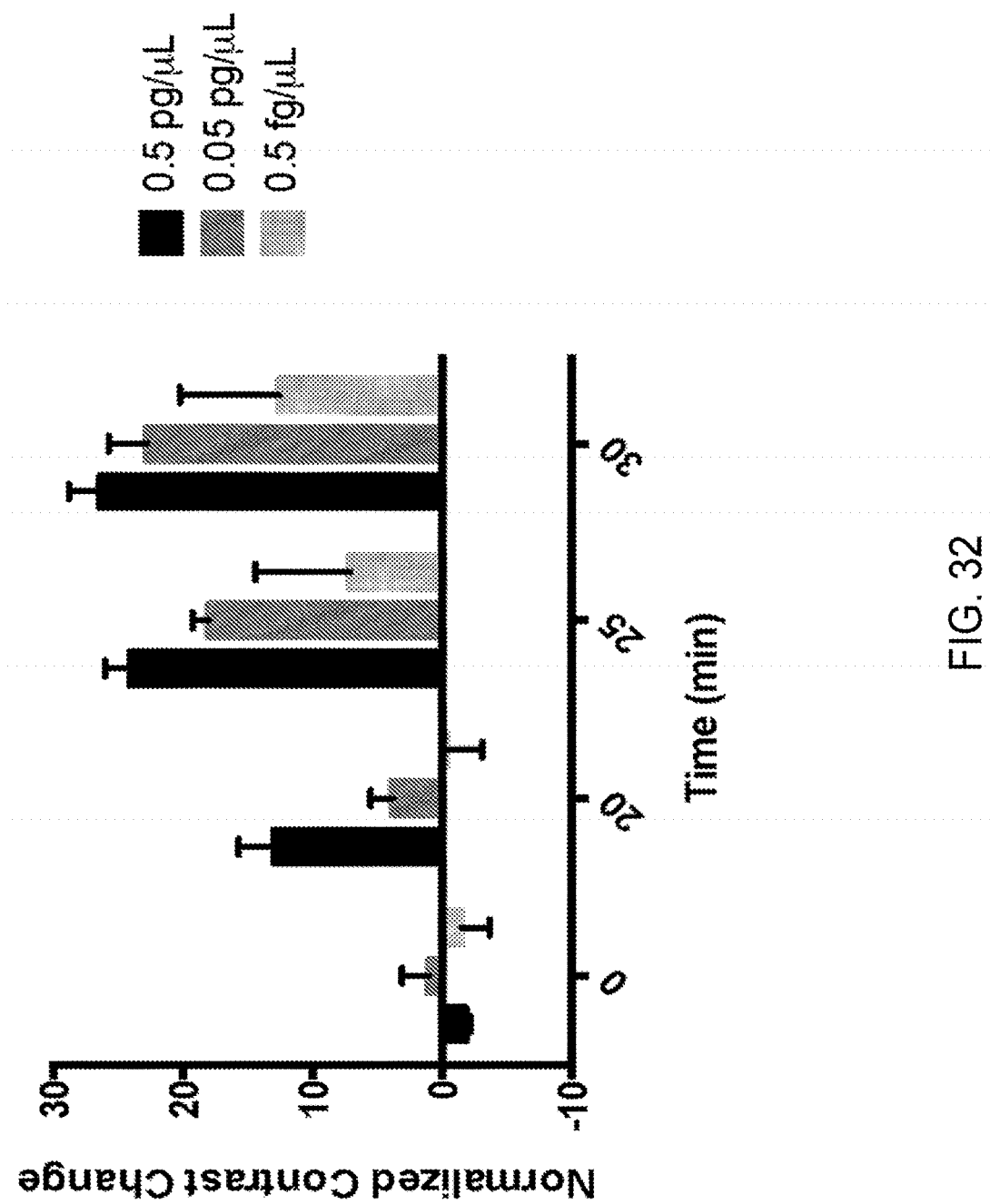
FIG. 32 shows the normalized contrast changes over time for different DNA template concentrations, according to an embodiment.

Example 7: Increase in Visual Detection Contrast with Combination of Halochromic Agents LAMP reactions were performed as in Example 1 with 1.3 mM final Tris buffer concentration (buffer formulated to pH 8.8), 0.8 U/µl of Bst 2.0 DNA Polymerase and 5 ng lambda DNA template. The color change contrast was evaluated for Phenol Red at 50 µM concentration and combination of Phenol Red and Bromothymol Blue at 50 µM and 160 µM concentrations respectively (FIG. 31A). The color change contrast was also evaluated for Cresol Red at 260 µM concentration and combination of Cresol Red and Bromothymol Blue at 260 µM and 160 µM concentrations respectively (FIG. 31B). The contrast values were calculated from the RGB values of images of the reaction mix using the formula: 0.299R+0.587G+0.114B. The normalized contrast change was defined as the difference between positive and negative reaction contrast values normalized to the background. The increase in the normalized contrast change with the use of the halochromic agent combination demonstrates the utility of such combinations.

Example 8: Real-time Color Monitoring of Amplification for Quantification Using Visual Halochromic Agents LAMP reactions were performed as in Example 1 with 1.3 mM final Tris buffer concentration (buffer formulated to pH 8.8), 0.8 U/μl of Bst 2.0 DNA Polymerase, Phenol Red and Bromothymol Blue at 50 μM and 160 μM concentrations respectively and varying lambda DNA template concentrations. Color change contrast was evaluated for lambda DNA target at 0.5 fg/μl, 0.05 pg/μl and 0.5 pg/μl final concentrations. The contrast values were calculated from the RGB values of images of the reaction mix as described in Example 5. The results (FIG. 33) indicate that the higher DNA concentrations led to a detectable change in visual contrast earlier than the lower DNA concentrations. Hence, we demonstrate the ability to distinguish between different target concentrations with the real-time color monitoring of this chemistry.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications can be made thereto without departing from the spirit or scope of the appended claims.

The invention claimed is:

1. A system for performing a biological assay, the system comprising:
   a. a sample preparation device comprising:
      i. a sample receiving module comprising a fluid container comprising a preparation solution, a first opening, and a second opening;
      ii. a cap removably couplable to the sample receiving module, wherein coupling the cap to the sample receiving module seals the first opening; and
      iii. a valve or a breakable seal operatively coupled to the sample receiving module so as to seal the second opening;
   b. an optical property modifying device operatively couplable to the sample preparation device and comprising:
      i. a sample receiving cartridge operatively coupled to the valve or the breakable seal comprising one or more reaction chambers each comprising an optical property modifying reagent;
      ii. a substrate comprising a heating element; and
      iii. a first sensor configured to detect the presence and/or absence of liquid in one or more of the reaction chambers and a control unit;
      wherein when the optical property modifying device is operatively coupled to the sample preparation device and the valve is actuated from a sealed to unsealed conformation or the breakable seal is broken, the sample receiving module transmits at least a portion of the preparation solution through the valve or the breakable seal into the one or more reaction chambers, and wherein the first sensor, the control unit, and the heating element are operatively connected such that when liquid enters a reaction chamber, the first sensor senses the liquid and the heating element begins heating the reaction chamber automatically.

2. The system of claim 1, wherein the cap further comprises a pressurizing component, wherein when the cap is operatively coupled to the sample receiving module, the pressurizing component of the cap pressurizes the sample receiving module, wherein when the optical property modifying device is operatively coupled to the sample preparation device and the valve is actuated from a sealed to unsealed conformation or the breakable seal is broken, the sample receiving module depressurizes by transmitting at least a portion of the preparation solution through the valve or the breakable seal into the one or more reaction chambers.

3. The system of claim 1, wherein the cap comprises a first chamber, a plunger, a piercing member, and a breakable seal.

4. The system of claim 3, wherein advancing the plunger pierces the breakable seal with the piercing member, thereby placing the first chamber and the fluid container in fluidic communication.

5. The system according to claim 1, wherein the preparation solution is a nucleic acid amplification preparation solution.

6. The system according to claim 1, wherein the substrate comprises a power source operatively connected to the heating element or a printed circuit board.

7. The system according to claim 1, wherein the cap comprises a receptacle configured to receive an end of the sample receiving module therein when the cap is coupled to the sample receiving module.

8. The system according to claim 1, wherein the sample preparation device and the optical property modifying device are each hand-held devices.

9. The system according to claim 1, wherein the fluid container has a volume of 50 cm$^3$ or less.

10. The system according to claim 1, further comprising a sample collector.

11. The system according to claim 1, wherein the sample receiving module is shaped as a cylinder having a diameter of 5 cm or less and having a height of 20 cm or less.

12. The system according to claim 1, wherein the fluid container has a volume ranging from 1 mL to 10 mL.

13. The system according to claim 1, wherein the optical property modifying device further comprises an adhesive layer operatively connecting the sample receiving cartridge and the substrate and thereby forming a wall of each of the one or more reaction chambers.

14. The system according to claim 1, wherein the sample receiving module is adapted to receive one or more portions of a sample collector.

15. The system according to claim 1, wherein the sample receiving module comprises a first attachment element and the cap comprises a second attachment element operatively couplable with the first attachment element.

16. The system according to claim 1, wherein the sample receiving module comprises an outer body forming a first chamber, and wherein the fluid container comprises a breakable seal and an inner body forming a second chamber, wherein the inner body is movable within the outer body.

17. A method of determining one or more characteristics of a nucleic acid amplification sample based on a modified optical property of the sample, the method comprising:
 a. collecting a biological sample;
 b. providing the system of claim 1;
 c. inserting the biological sample comprising a nucleic acid into the preparation solution of the sample receiving module of the sample preparation device to produce a prepared nucleic acid amplification sample;
 d. operatively coupling the sample preparation device with the optical property modifying device;
 e. transmitting at least a portion of the prepared nucleic acid amplification sample out of the sample receiving module and into one or more reaction chambers of the optical property modifying device, wherein the chambers comprise an optical property modifying reagent and an amplification composition, and thereby generating a nucleic acid reaction mixture;
 f. heating the reaction mixture with the heating element of the optical property modifying device, wherein the heating accelerates a nucleic acid amplification reaction comprising the nucleic acid and the amplification composition, the reaction generating an amplified nucleic acid and a plurality of protons;
 g. reacting the protons with the optical property modifying reagent, wherein the reacting sufficiently modifies an optical property of the optical property modifying reagent to allow detection of the modified optical property; and
 h. determining one or more characteristics of the sample based on the modified optical property.

* * * * *